US012686878B2

(12) United States Patent
Zhang et al.

(10) Patent No.: US 12,686,878 B2
(45) Date of Patent: Jul. 21, 2026

(54) MICROORGANISM FOR PRODUCING PANTOIC ACID, AND CONSTRUCTION METHOD THEREFOR AND APPLICATION THEREOF

(71) Applicant: TIANJIN INSTITUTE OF INDUSTRIAL BIOTECHNOLOGY, CHINESE ACADEMY OF SCIENCES, Tianjin (CN)

(72) Inventors: Xueli Zhang, Tianjin (CN); Pingping Liu, Tianjin (CN); Jinlei Tang, Tianjin (CN)

(73) Assignee: TIANJIN INSTITUTE OF INDUSTRIAL BIOTECHNOLOGY, CHINESE ACADEMY OF SCIENCES (CN)

( * ) Notice: Subject to any disclaimer, the term of this patent is extended or adjusted under 35 U.S.C. 154(b) by 452 days.

(21) Appl. No.: 18/271,665

(22) PCT Filed: Jul. 13, 2021

(86) PCT No.: PCT/CN2021/105954
§ 371 (c)(1),
(2) Date: Jul. 10, 2023

(87) PCT Pub. No.: WO2022/198846
PCT Pub. Date: Sep. 29, 2022

(65) Prior Publication Data
US 2024/0011059 A1 Jan. 11, 2024

(30) Foreign Application Priority Data
Mar. 23, 2021 (CN) ......................... 202110391896.0

(51) Int. Cl.
| | |
|---|---|
| *C12N 15/52* | (2006.01) |
| *C12N 9/02* | (2006.01) |
| *C12N 9/04* | (2006.01) |
| *C12N 9/06* | (2006.01) |
| *C12N 9/10* | (2006.01) |
| *C12N 9/12* | (2006.01) |
| *C12N 9/16* | (2006.01) |
| *C12N 9/88* | (2006.01) |
| *C12N 15/70* | (2006.01) |
| *C12P 7/42* | (2006.01) |

(52) U.S. Cl.
CPC .............. *C12P 7/42* (2013.01); *C12N 9/0006* (2013.01); *C12N 9/001* (2013.01); *C12N 9/0016* (2013.01); *C12N 9/1014* (2013.01); *C12N 9/1022* (2013.01); *C12N 9/1029* (2013.01); *C12N 9/1096* (2013.01); *C12N 9/12* (2013.01); *C12N 9/127* (2013.01); *C12N 9/16* (2013.01); *C12N 9/88* (2013.01); *C12N 15/52* (2013.01); *C12N 15/70* (2013.01); *C12Y 101/01001* (2013.01); *C12Y 101/01028* (2013.01); *C12Y 101/01086* (2013.01); *C12Y 101/01095* (2013.01); *C12Y 101/01169* (2013.01); *C12Y 103/01006* (2013.01); *C12Y 201/02001* (2013.01); *C12Y 201/02011* (2013.01); *C12Y 202/01006* (2013.01); *C12Y 203/01008* (2013.01); *C12Y 203/01054* (2013.01); *C12Y 206/01042* (2013.01); *C12Y 206/01052* (2013.01); *C12Y 206/01066* (2013.01); *C12Y 207/01015* (2013.01); *C12Y 207/02001* (2013.01); *C12Y 207/02015* (2013.01); *C12Y 301/03003* (2013.01); *C12Y 402/01009* (2013.01); *C12Y 402/03003* (2013.01); *C12Y 403/01017* (2013.01); *C12N 2800/101* (2013.01)

(58) Field of Classification Search
None
See application file for complete search history.

(56) References Cited

U.S. PATENT DOCUMENTS

| | | |
|---|---|---|
| 9,605,280 B2 | 3/2017 | Zhang et al. |
| 2002/0137149 A1 | 9/2002 | Hermann et al. |

FOREIGN PATENT DOCUMENTS

| | | |
|---|---|---|
| CN | 101298622 A | 11/2008 |
| CN | 110607268 A | 12/2019 |
| WO | 03/004672 A1 | 1/2003 |
| WO | WO 2010/018196 | 2/2010 |
| WO | WO 2022/198846 W | 9/2022 |

OTHER PUBLICATIONS

Blazeck and Alper, Biotechnology Journal, vol. 8, pp. 46-58, 2013.*
International Search Report for PCT/CN2021/105954, dated Dec. 8, 2021, 4 pages.
Liu, et al. "Cloning and Expression of Fusarium moniliforme CGMCC 0536 D-Lactonohydrolase Gene in *Escherichia coli*" (2005) Chinese Journal of Biotechnology. 21:3 (391-396) w/Eng Abst.
Zou, et al. "High-level production of D-pantothenic acid from glucose by fed-batch cultivation of *Escherichia coli*" (2020) Biotechnology and Applied Biochemistry, 9 pages.

(Continued)

*Primary Examiner* — Richard G Hutson
(74) *Attorney, Agent, or Firm* — Husch Blackwell LLP

(57) ABSTRACT

Provided are a microorganism for producing a pantoic acid, and a construction method therefor and an application thereof. The microorganism for producing the pantoic acid is obtained by knocking out genes in *Escherichia coli* and introducing exogenous genes. The obtained microorganism is *Escherichia coli* that is registered in the China General Microbiological Culture Collection Center with an accession number of CGMCC No. 21699. A pantoic acid synthesis pathway has been opened up, and accumulation of the pantoic acid can be achieved in a fermentation process.

12 Claims, No Drawings
Specification includes a Sequence Listing.

(56)            References Cited

OTHER PUBLICATIONS

Extended European Search Report for PCT/CN2021/105954, Dated Nov. 19, 2024, 8 pages.
"Metabolic engineering of *Escherichia coli* for D-pantothenic acid production", Food Chemistry 294 (2019) 267-275, Zhang et al.

* cited by examiner

SEQUENCE LISTING

<160> NUMBER OF SEQ ID NOS: 148

<210> SEQ ID NO 1
<211> LENGTH: 1716
<212> TYPE: DNA
<213> ORGANISM: Artificial Sequence
<220> FEATURE:
<223> OTHER INFORMATION: Synthetic construct

<400> SEQUENCE: 1

```
atgttgacaa aagcaacaaa agaacaaaaa tcccttgtga aaaacagagg ggcggagctt      60
gttgttgatt gcttagtgga gcaaggtgtc acacatgtat ttggcattcc aggtgcaaaa     120
attgatgcgg tatttgacgc tttacaagat aaaggacctg aaattatcgt tgcccggcac     180
gaacaaaacg cagcattcat ggcccaagca gtcggccgtt taactggaaa accgggagtc     240
gtgttagtca catcaggacc gggtgcctct aacttggcaa caggcctgct gacagcgaac     300
actgaaggag accctgtcgt tgcgcttgct ggaaacgtga tccgtgcaga tcgtttaaaa     360
cggacacatc aatctttgga taatgcggcg ctattccagc cgattacaaa atacagtgta     420
gaagttcaag atgtaaaaaa tataccggaa gctgttacaa atgcatttag gatagcgtca     480
gcagggcagg ctggggccgc ttttgtgagc tttccgcaag atgttgtgaa tgaagtcaca     540
aatacgaaaa acgtgcgtgc tgttgcagcg ccaaaactcg gtcctgcagc agatgatgca     600
atcagtgcgg ccatagcaaa aatccaaaca gcaaaacttc ctgtcgtttt ggtcggcatg     660
aaaggcggaa gaccggaagc aattaaagcg gttcgcaagc ttttgaaaaa ggttcagctt     720
ccatttgttg aaacatatca agctgccggt accctttcta gagatttaga ggatcaatat     780
tttggccgta tcggtttgtt ccgcaaccag cctggcgatt tactgctaga gcaggcagat     840
gttgttctga cgatcggcta tgacccgatt gaatatgatc cgaaattctg gaatatcaat     900
ggagaccgga caattatcca tttagacgag attatcgctg acattgatca tgcttaccag     960
cctgatcttg aattgatcgg tgacattccg tccacgatca atcatatcga acacgatgct    1020
gtgaaagtgg aatttgcaga gcgtgagcag aaaatccttt ctgatttaaa acaatatatg    1080
catgaaggtg agcaggtgcc tgcagattgg aaatcagaca gagcgcaccc tcttgaaatc    1140
gttaaagagt tgcgtaatgc agtcgatgat catgttacag taacttgcga tatcggttcg    1200
cacgccattt ggatgtcacg ttatttccgc agctacgagc cgttaacatt aatgatcagt    1260
aacggtatgc aaacactcgg cgttgcgctt ccttgggcaa tcggcgcttc attggtgaaa    1320
ccgggagaaa aagtggtttc tgtctctggt gacggcggtt tcttattctc agcaatggaa    1380
ttagagacag cagttcgact aaaagcacca attgtacaca ttgtatggaa cgacagcaca    1440
tatgacatgg ttgcattcca gcaattgaaa aaatataacc gtacatctgc ggtcgatttc    1500
ggaaatatcg atatcgtgaa atatgcggaa agcttcggag caactggctt gcgcgtagaa    1560
tcaccagacc agctggcaga tgttctgcgt caaggcatga cgctgaagg tcctgtcatc    1620 atcgatgtcc cggttgacta cagtgataac attaatttag caagtgacaa gcttccgaaa    1680
gaattcgggg aactcatgaa aacgaaagct ctctag                              1716
```

<210> SEQ ID NO 2
<211> LENGTH: 571
<212> TYPE: PRT
<213> ORGANISM: Artificial Sequence
<220> FEATURE:
<223> OTHER INFORMATION: Synthetic construct

<400> SEQUENCE: 2

-continued

```
Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
            35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
            115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
            165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
            195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
            245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
            275                 280                 285

Pro Ile Glu Tyr Asp Pro Lys Phe Trp Asn Ile Asn Gly Asp Arg Thr
    290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
            325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
            355                 360                 365

Asp Trp Lys Ser Asp Arg Ala His Pro Leu Glu Ile Val Lys Glu Leu
            370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
            405                 410                 415
```

-continued

```
Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
            435                 440                 445

Ser Gly Asp Gly Gly Phe Leu Phe Ser Ala Met Glu Leu Glu Thr Ala
            450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
            515                 520                 525

Leu Arg Gln Gly Met Asn Ala Glu Gly Pro Val Ile Ile Asp Val Pro
        530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570
```

```
<210> SEQ ID NO 3
<211> LENGTH: 88
<212> TYPE: DNA
<213> ORGANISM: Artificial Sequence
<220> FEATURE:
<223> OTHER INFORMATION: Synthetic construct

<400> SEQUENCE: 3
ttatctctgg cggtgttgac aagagataac aacgttgata taattgagcc cgtattgtta      60
gcatgtacgt ttaaaccagg aaacagct                                          88

<210> SEQ ID NO 4
<211> LENGTH: 492
<212> TYPE: DNA
<213> ORGANISM: Artificial Sequence
<220> FEATURE:
<223> OTHER INFORMATION: Synthetic construct

<400> SEQUENCE: 4
atgcgccgga tattatcagt cttactcgaa aatgaatcag acgcgttatt ccgcgtgatt      60
ggcctttttt cccagcgtgg ctacaacatt gaaagcctga ccgttgcgcc aaccgacgat     120
ccgacattat cgcgtatgac catccagacc gtgggcgatg aaaaagtact tgagcagatc     180
gaaaagcaat tacacaagct ggtcgatgtc ttgcgcgtga gtgagttggg gcagggcgcg     240
catgttgagc gggaaatcat gctggtgaaa attcaggcca gcggttacgg gcgtgacgaa     300
gtgaaacgta atacggaaat attccgtggg caaattatcg atgtcacacc ctcgctttat     360
accgttcaat tagcaggcac cagcggtaag cttgatgcat ttttagcatc gattcgcgat     420
gtggcgaaaa ttgtggaggt tgctcgctct ggtgtggtcg actttcgcg cggcgataaa     480 ataatgcgtt ga                                                         492

<210> SEQ ID NO 5
<211> LENGTH: 163
<212> TYPE: PRT
<213> ORGANISM: Artificial Sequence
<220> FEATURE:
<223> OTHER INFORMATION: Synthetic construct
```

```
<400> SEQUENCE: 5

Met Arg Arg Ile Leu Ser Val Leu Leu Glu Asn Glu Ser Asp Ala Leu
1               5                   10                  15

Phe Arg Val Ile Gly Leu Phe Ser Gln Arg Gly Tyr Asn Ile Glu Ser
            20                  25                  30

Leu Thr Val Ala Pro Thr Asp Asp Pro Thr Leu Ser Arg Met Thr Ile
        35                  40                  45

Gln Thr Val Gly Asp Glu Lys Val Leu Glu Gln Ile Glu Lys Gln Leu
    50                  55                  60

His Lys Leu Val Asp Val Leu Arg Val Ser Glu Leu Gly Gln Gly Ala
65                  70                  75                  80

His Val Glu Arg Glu Ile Met Leu Val Lys Ile Gln Ala Ser Gly Tyr
                85                  90                  95

Gly Arg Asp Glu Val Lys Arg Asn Thr Glu Ile Phe Arg Gly Gln Ile
            100                 105                 110

Ile Asp Val Thr Pro Ser Leu Tyr Thr Val Gln Leu Ala Gly Thr Ser
        115                 120                 125

Gly Lys Leu Asp Ala Phe Leu Ala Ser Ile Arg Asp Val Ala Lys Ile
    130                 135                 140

Val Glu Val Ala Arg Ser Gly Val Val Gly Leu Ser Arg Gly Asp Lys
145                 150                 155                 160

Ile Met Arg

<210> SEQ ID NO 6
<211> LENGTH: 88
<212> TYPE: DNA
<213> ORGANISM: Artificial Sequence
<220> FEATURE:
<223> OTHER INFORMATION: Synthetic construct

<400> SEQUENCE: 6
ttatctctgg cggtgttgac aagagataac aacgttgata taattgagcc tctcgcccca       60
ccaattcggt ttaaaccagg aaacagct                                          88

<210> SEQ ID NO 7
<211> LENGTH: 89
<212> TYPE: DNA
<213> ORGANISM: Artificial Sequence
<220> FEATURE:
<223> OTHER INFORMATION: Synthetic construct

<400> SEQUENCE: 7
ttatctctgg cggtgttgac aagagataac aacgttgata taattgagcc cgtattgtta       60
gcatgtacgt ttaaaccagg aggtcagca                                         89

<210> SEQ ID NO 8
<211> LENGTH: 89
<212> TYPE: DNA
<213> ORGANISM: Artificial Sequence
<220> FEATURE:
<223> OTHER INFORMATION: Synthetic construct

<400> SEQUENCE: 8
ttatctctgg cggtgttgac aagagataac aacgttgata taattgagcc cgtattgtta       60
gcatgtacgt ttaaaccagg agggttcga                                         89

<210> SEQ ID NO 9
```

<211> LENGTH: 816
<212> TYPE: DNA
<213> ORGANISM: Artificial Sequence
<220> FEATURE:
<223> OTHER INFORMATION: Synthetic construct

<400> SEQUENCE: 9

```
atgcccatgt caggcattga tgcaaagaaa atccgcaccc gtcatttccg cgaagctaaa      60
gtaaacggcc agaaagtttc ggttctcacc agctatgatg cgctttcggc gcgcattttt     120
gatgaggctg gcgtcgatat gctccttgtt ggtgattccg ctgccaacgt tgtgctgggt     180
cgcgatacca ccttgtcgat caccttggat gagatgattg tgctggccaa ggcggtgacg     240
atcgctacga agcgtgcgct tgtggtggtt gatctgccgt ttggtaccta tgaggtgagc     300
ccaaatcagg cggtggagtc cgcgatccgg gtcatgcgtg aaacgggtgc ggctgcggtg     360
aagatcgagg gtggcgtgga gatcgcgcag acgattcgac gcattgttga tgctggaatt     420
ccggttgtcg gccacatcgg gtacaccccg cagtccgagc attccttggg cggccacgtg     480
gttcagggtc gtggcgcgag ttctggaaag ctcatcgccg atgcccgcgc gttggagcag     540
gcgggtgcgt ttgcggttgt gttggagatg gttccagcag aggcagcgcg cgaggttacc     600
gaggatcttt ccatcaccac tatcggaatc ggtgccggca atggcacaga tgggcaggtt     660
ttggtgtggc aggatgcctt cggcctcaac cgcggcaaga agccacgctt cgtccgcgag     720
tacgccacct tgggcgattc cttgcacgac gccgcgcagg cctacatcgc cgatatccac     780
gcgggtacct ccccaggcga agcggagtcc ttttaa                               816
```

<210> SEQ ID NO 10
<211> LENGTH: 271
<212> TYPE: PRT
<213> ORGANISM: Artificial Sequence
<220> FEATURE:
<223> OTHER INFORMATION: Synthetic construct

<400> SEQUENCE: 10

```
Met Pro Met Ser Gly Ile Asp Ala Lys Lys Ile Arg Thr Arg His Phe
1               5                   10                  15

Arg Glu Ala Lys Val Asn Gly Gln Lys Val Ser Val Leu Thr Ser Tyr
            20                  25                  30

Asp Ala Leu Ser Ala Arg Ile Phe Asp Glu Ala Gly Val Asp Met Leu
        35                  40                  45

Leu Val Gly Asp Ser Ala Ala Asn Val Val Leu Gly Arg Asp Thr Thr
    50                  55                  60

Leu Ser Ile Thr Leu Asp Glu Met Ile Val Leu Ala Lys Ala Val Thr
65                  70                  75                  80

Ile Ala Thr Lys Arg Ala Leu Val Val Val Asp Leu Pro Phe Gly Thr
                85                  90                  95

Tyr Glu Val Ser Pro Asn Gln Ala Val Glu Ser Ala Ile Arg Val Met
            100                 105                 110

Arg Glu Thr Gly Ala Ala Ala Val Lys Ile Glu Gly Gly Val Glu Ile
        115                 120                 125

Ala Gln Thr Ile Arg Arg Ile Val Asp Ala Gly Ile Pro Val Val Gly
    130                 135                 140

His Ile Gly Tyr Thr Pro Gln Ser Glu His Ser Leu Gly Gly His Val
145                 150                 155                 160

Val Gln Gly Arg Gly Ala Ser Ser Gly Lys Leu Ile Ala Asp Ala Arg
                165                 170                 175
```

-continued

```
Ala Leu Glu Gln Ala Gly Ala Phe Ala Val Val Leu Glu Met Val Pro
            180                 185                 190

Ala Glu Ala Ala Arg Glu Val Thr Glu Asp Leu Ser Ile Thr Thr Ile
        195                 200                 205

Gly Ile Gly Ala Gly Asn Gly Thr Asp Gly Gln Val Leu Val Trp Gln
        210                 215                 220

Asp Ala Phe Gly Leu Asn Arg Gly Lys Lys Pro Arg Phe Val Arg Glu
225                 230                 235                 240

Tyr Ala Thr Leu Gly Asp Ser Leu His Asp Ala Ala Gln Ala Tyr Ile
                245                 250                 255

Ala Asp Ile His Ala Gly Thr Phe Pro Gly Glu Ala Glu Ser Phe
            260                 265                 270
```

```
<210> SEQ ID NO 11
<211> LENGTH: 930
<212> TYPE: DNA
<213> ORGANISM: Artificial Sequence
<220> FEATURE:
<223> OTHER INFORMATION: Synthetic construct

<400> SEQUENCE: 11
gtgaccacga agaaagctga ttacatttgg ttcaatgggg agatggttcg ctgggaagac      60
gcgaaggtgc atgtgatgtc gcacgcgctg cactatggca cctcggtttt tgaaggcatc     120
cgttgctacg actcgcacaa aggaccggtt gtattccgcc atcgtgagca tatgcagcgt     180
ctgcatgact ccgccaaaat ctatcgcttt ccggtttcgc agagcattga tgagctgatg     240
gaagcttgtc gtgacgtgat ccgcaaaaac aatctcacca gcgcctatat ccgtccgctg     300
atcttcgtcg gtgatgttgg catgggcgtt aacccgccag cgggatactc aaccgatgtg     360
attatcgccg ctttcccgtg gggagcgtat ctgggcgcag aagcgctgga gcaggggatc     420
gatgcgatgg tttcctcctg gaaccgcgca gcaccaaaca ccatcccaac cgcggcaaaa     480
gccggtggta actacctctc ttccctgctg gtgggtagtg aagcacgccg ccacggttat     540
caggaaggta tcgcgctgga tgtgaatggt tacatctctg aaggtgcagg cgaaaacctg     600
tttgaagtga aagacggcgt gctgttcacc ccaccgttca cctcctccgc gctgccgggt     660
attacccgtg atgccatcat caaactggca aaagagctgg gaattgaagt ccgtgagcag     720
gtgctgtcgc gcgaatccct gtacctggcg gatgaagtgt ttatgtccgg tactgcggca     780
gaaatcacgc cagtgcgcag cgtagatggt attcaggttg gtgaaggccg ttgcggcccg     840
gttaccaaac gcatccagca agccttcttc ggcctcttca ctggcgaaac cgaagataaa     900
tggggctggt tagatcaagt taatcaataa                                      930
```

```
<210> SEQ ID NO 12
<211> LENGTH: 309
<212> TYPE: PRT
<213> ORGANISM: Artificial Sequence
<220> FEATURE:
<223> OTHER INFORMATION: Synthetic construct

<400> SEQUENCE: 12

Val Thr Thr Lys Lys Ala Asp Tyr Ile Trp Phe Asn Gly Glu Met Val
1               5                   10                  15

Arg Trp Glu Asp Ala Lys Val His Val Met Ser His Ala Leu His Tyr
            20                  25                  30

Gly Thr Ser Val Phe Glu Gly Ile Arg Cys Tyr Asp Ser His Lys Gly
        35                  40                  45
```

-continued

```
Pro Val Val Phe Arg His Arg Glu His Met Gln Arg Leu His Asp Ser
    50              55              60

Ala Lys Ile Tyr Arg Phe Pro Val Ser Gln Ser Ile Asp Glu Leu Met
65              70              75              80

Glu Ala Cys Arg Asp Val Ile Arg Lys Asn Asn Leu Thr Ser Ala Tyr
                85              90              95

Ile Arg Pro Leu Ile Phe Val Gly Asp Val Gly Met Gly Val Asn Pro
            100             105             110

Pro Ala Gly Tyr Ser Thr Asp Val Ile Ile Ala Ala Phe Pro Trp Gly
            115             120             125

Ala Tyr Leu Gly Ala Glu Ala Leu Glu Gln Gly Ile Asp Ala Met Val
    130             135             140

Ser Ser Trp Asn Arg Ala Ala Pro Asn Thr Ile Pro Thr Ala Ala Lys
145             150             155             160

Ala Gly Gly Asn Tyr Leu Ser Ser Leu Leu Val Gly Ser Glu Ala Arg
                165             170             175

Arg His Gly Tyr Gln Glu Gly Ile Ala Leu Asp Val Asn Gly Tyr Ile
            180             185             190

Ser Glu Gly Ala Gly Glu Asn Leu Phe Glu Val Lys Asp Gly Val Leu
            195             200             205

Phe Thr Pro Pro Phe Thr Ser Ser Ala Leu Pro Gly Ile Thr Arg Asp
    210             215             220

Ala Ile Ile Lys Leu Ala Lys Glu Leu Gly Ile Glu Val Arg Glu Gln
225             230             235             240

Val Leu Ser Arg Glu Ser Leu Tyr Leu Ala Asp Glu Val Phe Met Ser
                245             250             255

Gly Thr Ala Ala Glu Ile Thr Pro Val Arg Ser Val Asp Gly Ile Gln
            260             265             270

Val Gly Glu Gly Arg Cys Gly Pro Val Thr Lys Arg Ile Gln Gln Ala
            275             280             285

Phe Phe Gly Leu Phe Thr Gly Glu Thr Glu Asp Lys Trp Gly Trp Leu
    290             295             300

Asp Gln Val Asn Gln
305
```

<210> SEQ ID NO 13
<211> LENGTH: 1002
<212> TYPE: DNA
<213> ORGANISM: Artificial Sequence
<220> FEATURE:
<223> OTHER INFORMATION: Synthetic construct

<400> SEQUENCE: 13

```
atgagccaga atggccgtcc ggtagtcctc atcgccgata agcttgcgca gtccactgtt        60
gacgcgcttg gagatgcagt agaagtccgt tgggttgacg gacctaaccg cccagaactg       120
cttgatgcag ttaaggaagc ggacgcactg ctcgtgcgtt ctgctaccac tgtcgatgct       180
gaagtcatcg ccgctgcccc taacttgaag atcgtcggtc gtgccggcgt gggcttggac       240
aacgttgaca tccctgctgc cactgaagct ggcgtcatgg ttgctaacgc accgacctct       300
aatattcact ccgcttgtga gcacgcaatt tctttgctgc tgtctactgc tcgccagatc       360
cctgctgctg atgcgacgct gcgtgagggc gagtggaagc ggtcttcttt caacggtgtg       420
gaaattttcg gaaaaactgt cggtatcgtc ggttttggcc acattggtca gttgtttgct       480
cagcgtcttg ctgcgtttga gaccaccatt gttgcttacg atccttacgc taaccctgct       540
```

-continued

```
cgtgcggctc agctgaacgt tgagttggtt gagttggatg agctgatgag ccgttctgac      600
tttgtcacca ttcaccttcc taagaccaag gaaactgctg gcatgtttga tgcgcagctc      660
cttgctaagt ccaagaaggg ccagatcatc atcaacgctg ctcgtggtgg ccttgttgat      720
gagcaggctt tggctgatgc gattgagtcc ggtcacattc gtggcgctgg tttcgatgtg      780
tactccaccg agccttgcac tgattctcct ttgttcaagt tgcctcaggt tgttgtgact      840
cctcacttgg gtgcttctac tgaagaggct caggatcgtg cgggtactga cgttgctgat      900
tctgtgctca aggcgctggc tggcgagttc gtggcggatg ctgtgaacgt ttccggtggt      960
cgcgtgggcg aagaggttgc tgtgtggatg gatctggctt aa                          1002
```

<210> SEQ ID NO 14
<211> LENGTH: 333
<212> TYPE: PRT
<213> ORGANISM: Artificial Sequence
<220> FEATURE:
<223> OTHER INFORMATION: Synthetic construct

<400> SEQUENCE: 14

```
Met Ser Gln Asn Gly Arg Pro Val Val Leu Ile Ala Asp Lys Leu Ala
1               5                   10                  15

Gln Ser Thr Val Asp Ala Leu Gly Asp Ala Val Glu Val Arg Trp Val
            20                  25                  30

Asp Gly Pro Asn Arg Pro Glu Leu Leu Asp Ala Val Lys Glu Ala Asp
        35                  40                  45

Ala Leu Leu Val Arg Ser Ala Thr Thr Val Asp Ala Glu Val Ile Ala
    50                  55                  60

Ala Ala Pro Asn Leu Lys Ile Val Gly Arg Ala Gly Val Gly Leu Asp
65                  70                  75                  80

Asn Val Asp Ile Pro Ala Ala Thr Glu Ala Gly Val Met Val Ala Asn
                85                  90                  95

Ala Pro Thr Ser Asn Ile His Ser Ala Cys Glu His Ala Ile Ser Leu
            100                 105                 110

Leu Leu Ser Thr Ala Arg Gln Ile Pro Ala Ala Asp Ala Thr Leu Arg
        115                 120                 125

Glu Gly Glu Trp Lys Arg Ser Ser Phe Asn Gly Val Glu Ile Phe Gly
    130                 135                 140

Lys Thr Val Gly Ile Val Gly Phe Gly His Ile Gly Gln Leu Phe Ala
145                 150                 155                 160

Gln Arg Leu Ala Ala Phe Glu Thr Thr Ile Val Ala Tyr Asp Pro Tyr
                165                 170                 175

Ala Asn Pro Ala Arg Ala Ala Gln Leu Asn Val Glu Leu Val Glu Leu
            180                 185                 190

Asp Glu Leu Met Ser Arg Ser Asp Phe Val Thr Ile His Leu Pro Lys
        195                 200                 205

Thr Lys Glu Thr Ala Gly Met Phe Asp Ala Gln Leu Leu Ala Lys Ser
    210                 215                 220

Lys Lys Gly Gln Ile Ile Ile Asn Ala Ala Arg Gly Gly Leu Val Asp
225                 230                 235                 240

Glu Gln Ala Leu Ala Asp Ala Ile Glu Ser Gly His Ile Arg Gly Ala
                245                 250                 255

Gly Phe Asp Val Tyr Ser Thr Glu Pro Cys Thr Asp Ser Pro Leu Phe
            260                 265                 270

Lys Leu Pro Gln Val Val Val Thr Pro His Leu Gly Ala Ser Thr Glu
        275                 280                 285
```

-continued

```
Glu Ala Gln Asp Arg Ala Gly Thr Asp Val Ala Asp Ser Val Leu Lys
    290                 295                 300

Ala Leu Ala Gly Glu Phe Val Ala Asp Ala Val Asn Val Ser Gly Gly
305                 310                 315                 320

Arg Val Gly Glu Glu Val Ala Val Trp Met Asp Leu Ala
                325                 330

<210> SEQ ID NO 15
<211> LENGTH: 2167
<212> TYPE: DNA
<213> ORGANISM: Artificial Sequence
<220> FEATURE:
<223> OTHER INFORMATION: Synthetic construct

<400> SEQUENCE: 15
ttatctctgg cggtgttgac aagagataac aacgttgata taattgagcc cgtattgtta     60
gcatgtacgt ttaaaccagg aaacagctat ggctcaaatc ttcaatttta gttctggtcc    120
ggcaatgcta ccggcagagg tgcttaaaca ggctcaacag gaactgcgcg actggaacgg    180
tcttggtacg tcggtgatgg aagtgagtca ccgtggcaaa gagttcattc aggttgcaga    240
ggaagccgag aaggattttc gcgatcttct taatgtcccc tccaactaca aggtattatt    300
ctgccatggc ggtggtcgcg gtcagtttgc tgcggtaccg ctgaatattc tcggtgataa    360
aaccaccgca gattatgttg atgccggtta ctgggcggca agtgccatta agaagcgaa    420 aaaatactgc acgcctaatg tctttgacgc caaagtgact gttgatggtc tgcgcgcggt    480
taagccaatg cgtgaatggc aactctctga taatgctgct tatatgcatt attgcccgaa    540
tgaaaccatc gatggtatcg ccatcgacga aacgccagac ttcggcgcag atgtggtggt    600
cgccgctgac ttctcttcaa ccattctttc ccgtccgatt gacgtcagcc gttatggtgt    660
aatttacgct ggcgcgcaga aaaatatcgg cccggctggc ctgacaatcg tcatcgttcg    720
tgaagatttg ctgggcaaag cgaatatcgc gtgtccgtcg attctggatt attccatcct    780
caacgataac ggctccatgt ttaacacgcc gccgacattt gcctggtatc tatctggtct    840
ggtctttaaa tggctgaaag cgaacggcgg tgtagctgaa atggataaaa tcaatcagca    900
aaaagcagaa ctgctatatg gggtgattga taacagcgat ttctaccgca atgacgtggc    960
gaaagctaac cgttcgcgga tgaacgtgcc gttccagttg gcggcagtg cgcttgacaa   1020 attgttcctt gaagagtctt ttgctgctgg ccttcatgca ctgaaaggtc accgtgtggt   1080
cggcggaatg cgcgcttcta tttataacgc catgccgctg gaaggcgtta aagcgctgac   1140
agacttcatg gttgagttcg aacgccgtca cggttaagtc gacaaaagga gaacaaacat   1200
gcctaacatt acctggtgcg acctgcctga agatgtctct ttatggccgg tctgcctct   1260 ttcattaagt ggtgatgaag tgatgccact ggattaccac gcaggtcgta gcggctggct   1320
gctgtatggt cgtgggctgg ataaacaacg tctgacccaa taccagagca aactgggtgc   1380
ggcgatggtg attgttgccg cctggtgcgt ggaagattat caggtgattc gtctggcagg   1440
ttcactcacc gcacgggcta cacgcctggc ccacgaagcg cagctggatg tcgccccgct   1500
ggggaaaatc ccgcacctgc gcacgccggg tttgctggtg atggatatgg actccaccgc   1560
catccagatt gaatgtattg atgaaattgc caaactggcc ggaacgggcg agatggtggc   1620
ggaagtaacc gaacgggcga tgcgcggcga actcgatttt accgccagcc tgcgcagccg   1680
tgtggcgacg ctgaaaggcg ctgacgccaa tattctgcaa caggtgcgtg aaaatctgcc   1740
gctgatgcca ggcttaacgc aactggtgct caagctggaa acgctgggct ggaaagtggc   1800
```

```
gattgcctcc ggcggcttta ctttctttgc tgaatacctg cgcgacaagc tgcgcctgac   1860
cgccgtggta gccaatgaac tggagatcat ggacggtaaa tttaccggca atgtgatcgg   1920
cgacatcgta gacgcgcagt acaaagcgaa aactctgact cgcctcgcgc aggagtatga   1980
aatcccgctg gcgcagaccg tggcgattgg cgatggagcc aatgacctgc cgatgatcaa   2040
agcggcaggg ctggggattg cctaccatgc caagccaaaa gtgaatgaaa aggcggaagt   2100
caccatccgt cacgctgacc tgatgggggt attctgcatc ctctcaggca gcctgaatca   2160
gaagtaa                                                             2167
```

```
<210> SEQ ID NO 16
<211> LENGTH: 362
<212> TYPE: PRT
<213> ORGANISM: Artificial Sequence
<220> FEATURE:
<223> OTHER INFORMATION: Synthetic construct

<400> SEQUENCE: 16

Met Ala Gln Ile Phe Asn Phe Ser Ser Gly Pro Ala Met Leu Pro Ala
1               5                   10                  15

Glu Val Leu Lys Gln Ala Gln Gln Glu Leu Arg Asp Trp Asn Gly Leu
            20                  25                  30

Gly Thr Ser Val Met Glu Val Ser His Arg Gly Lys Glu Phe Ile Gln
        35                  40                  45

Val Ala Glu Glu Ala Glu Lys Asp Phe Arg Asp Leu Leu Asn Val Pro
    50                  55                  60

Ser Asn Tyr Lys Val Leu Phe Cys His Gly Gly Gly Arg Gly Gln Phe
65                  70                  75                  80

Ala Ala Val Pro Leu Asn Ile Leu Gly Asp Lys Thr Thr Ala Asp Tyr
                85                  90                  95

Val Asp Ala Gly Tyr Trp Ala Ala Ser Ala Ile Lys Glu Ala Lys Lys
            100                 105                 110

Tyr Cys Thr Pro Asn Val Phe Asp Ala Lys Val Thr Val Asp Gly Leu
        115                 120                 125

Arg Ala Val Lys Pro Met Arg Glu Trp Gln Leu Ser Asp Asn Ala Ala
    130                 135                 140

Tyr Met His Tyr Cys Pro Asn Glu Thr Ile Asp Gly Ile Ala Ile Asp
145                 150                 155                 160

Glu Thr Pro Asp Phe Gly Ala Asp Val Val Val Ala Ala Asp Phe Ser
                165                 170                 175

Ser Thr Ile Leu Ser Arg Pro Ile Asp Val Ser Arg Tyr Gly Val Ile
            180                 185                 190

Tyr Ala Gly Ala Gln Lys Asn Ile Gly Pro Ala Gly Leu Thr Ile Val
        195                 200                 205

Ile Val Arg Glu Asp Leu Leu Gly Lys Ala Asn Ile Ala Cys Pro Ser
    210                 215                 220

Ile Leu Asp Tyr Ser Ile Leu Asn Asp Asn Gly Ser Met Phe Asn Thr
225                 230                 235                 240

Pro Pro Thr Phe Ala Trp Tyr Leu Ser Gly Leu Val Phe Lys Trp Leu
                245                 250                 255

Lys Ala Asn Gly Gly Val Ala Glu Met Asp Lys Ile Asn Gln Gln Lys
            260                 265                 270

Ala Glu Leu Leu Tyr Gly Val Ile Asp Asn Ser Asp Phe Tyr Arg Asn
        275                 280                 285
```

-continued

```
Asp Val Ala Lys Ala Asn Arg Ser Arg Met Asn Val Pro Phe Gln Leu
    290             295             300

Ala Asp Ser Ala Leu Asp Lys Leu Phe Leu Glu Glu Ser Phe Ala Ala
305             310             315             320

Gly Leu His Ala Leu Lys Gly His Arg Val Val Gly Gly Met Arg Ala
            325             330             335

Ser Ile Tyr Asn Ala Met Pro Leu Glu Gly Val Lys Ala Leu Thr Asp
            340             345             350

Phe Met Val Glu Phe Glu Arg Arg His Gly
        355             360

<210> SEQ ID NO 17
<211> LENGTH: 322
<212> TYPE: PRT
<213> ORGANISM: Artificial Sequence
<220> FEATURE:
<223> OTHER INFORMATION: Synthetic construct

<400> SEQUENCE: 17

Met Pro Asn Ile Thr Trp Cys Asp Leu Pro Glu Asp Val Ser Leu Trp
1               5               10              15

Pro Gly Leu Pro Leu Ser Leu Ser Gly Asp Glu Val Met Pro Leu Asp
            20              25              30

Tyr His Ala Gly Arg Ser Gly Trp Leu Leu Tyr Gly Arg Gly Leu Asp
        35              40              45

Lys Gln Arg Leu Thr Gln Tyr Gln Ser Lys Leu Gly Ala Ala Met Val
    50              55              60

Ile Val Ala Ala Trp Cys Val Glu Asp Tyr Gln Val Ile Arg Leu Ala
65              70              75              80

Gly Ser Leu Thr Ala Arg Ala Thr Arg Leu Ala His Glu Ala Gln Leu
            85              90              95

Asp Val Ala Pro Leu Gly Lys Ile Pro His Leu Arg Thr Pro Gly Leu
            100             105             110

Leu Val Met Asp Met Asp Ser Thr Ala Ile Gln Ile Glu Cys Ile Asp
        115             120             125

Glu Ile Ala Lys Leu Ala Gly Thr Gly Glu Met Val Ala Glu Val Thr
    130             135             140

Glu Arg Ala Met Arg Gly Glu Leu Asp Phe Thr Ala Ser Leu Arg Ser
145             150             155             160

Arg Val Ala Thr Leu Lys Gly Ala Asp Ala Asn Ile Leu Gln Gln Val
            165             170             175

Arg Glu Asn Leu Pro Leu Met Pro Gly Leu Thr Gln Leu Val Leu Lys
        180             185             190

Leu Glu Thr Leu Gly Trp Lys Val Ala Ile Ala Ser Gly Gly Phe Thr
        195             200             205

Phe Phe Ala Glu Tyr Leu Arg Asp Lys Leu Arg Leu Thr Ala Val Val
    210             215             220

Ala Asn Glu Leu Glu Ile Met Asp Gly Lys Phe Thr Gly Asn Val Ile
225             230             235             240

Gly Asp Ile Val Asp Ala Gln Tyr Lys Ala Lys Thr Leu Thr Arg Leu
            245             250             255

Ala Gln Glu Tyr Glu Ile Pro Leu Ala Gln Thr Val Ala Ile Gly Asp
            260             265             270

Gly Ala Asn Asp Leu Pro Met Ile Lys Ala Ala Gly Leu Gly Ile Ala
            275             280             285
```

```
Tyr His Ala Lys Pro Lys Val Asn Glu Lys Ala Glu Val Thr Ile Arg
    290             295             300

His Ala Asp Leu Met Gly Val Phe Cys Ile Leu Ser Gly Ser Leu Asn
305             310             315             320

Gln Lys

<210> SEQ ID NO 18
<211> LENGTH: 73
<212> TYPE: DNA
<213> ORGANISM: Artificial Sequence
<220> FEATURE:
<223> OTHER INFORMATION: Synthetic construct

<400> SEQUENCE: 18
ccgtgattgg tctgctgacc atcctgaaca tcgtatacaa actgttttaa tgtgacggaa      60
gatcacttcg cag                                                        73

<210> SEQ ID NO 19
<211> LENGTH: 75
<212> TYPE: DNA
<213> ORGANISM: Artificial Sequence
<220> FEATURE:
<223> OTHER INFORMATION: Synthetic construct

<400> SEQUENCE: 19
ataatgttct ttgctacagg aaaatcaaca atatgcgcac cagatgccac ttatttgtta      60
actgttaatt gtcct                                                      75

<210> SEQ ID NO 20
<211> LENGTH: 72
<212> TYPE: DNA
<213> ORGANISM: Artificial Sequence
<220> FEATURE:
<223> OTHER INFORMATION: Synthetic construct

<400> SEQUENCE: 20
ccgtgattgg tctgctgacc atcctgaaca tcgtatacaa actgttttaa atgttgacaa      60
aagcaacaaa ag                                                         72

<210> SEQ ID NO 21
<211> LENGTH: 82
<212> TYPE: DNA
<213> ORGANISM: Artificial Sequence
<220> FEATURE:
<223> OTHER INFORMATION: Synthetic construct

<400> SEQUENCE: 21
ataatgttct ttgctacagg aaaatcaaca atatgcgcac cagatgccac gcatgagctc      60
ctagagagct ttcgttttca tg                                              82

<210> SEQ ID NO 22
<211> LENGTH: 21
<212> TYPE: DNA
<213> ORGANISM: Artificial Sequence
<220> FEATURE:
<223> OTHER INFORMATION: Synthetic construct

<400> SEQUENCE: 22
tgatgagcta cctggtatgg c                                               21

<210> SEQ ID NO 23
<211> LENGTH: 24
```

```
<212> TYPE: DNA
<213> ORGANISM: Artificial Sequence
<220> FEATURE:
<223> OTHER INFORMATION: Synthetic construct

<400> SEQUENCE: 23
cgccgacaga gtaataggtt ttac                                          24

<210> SEQ ID NO 24
<211> LENGTH: 75
<212> TYPE: DNA
<213> ORGANISM: Artificial Sequence
<220> FEATURE:
<223> OTHER INFORMATION: Synthetic construct

<400> SEQUENCE: 24
cctctgtttt tcacaaggga tttttgttct tttgttgctt ttgtcaacat ttatttgtta    60
actgttaatt gtcct                                                     75

<210> SEQ ID NO 25
<211> LENGTH: 70
<212> TYPE: DNA
<213> ORGANISM: Artificial Sequence
<220> FEATURE:
<223> OTHER INFORMATION: Synthetic construct

<400> SEQUENCE: 25
ccgtgattgg tctgctgacc atcctgaaca tcgtatacaa actgttttaa ttatctctgg    60
cggtgttgac                                                           70

<210> SEQ ID NO 26
<211> LENGTH: 70
<212> TYPE: DNA
<213> ORGANISM: Artificial Sequence
<220> FEATURE:
<223> OTHER INFORMATION: Synthetic construct

<400> SEQUENCE: 26
cctctgtttt tcacaaggga tttttgttct tttgttgctt ttgtcaacat agctgtttcc    60
tggtttaaac                                                           70

<210> SEQ ID NO 27
<211> LENGTH: 20
<212> TYPE: DNA
<213> ORGANISM: Artificial Sequence
<220> FEATURE:
<223> OTHER INFORMATION: Synthetic construct

<400> SEQUENCE: 27
gcctgttgcc aagttagagg                                                20

<210> SEQ ID NO 28
<211> LENGTH: 72
<212> TYPE: DNA
<213> ORGANISM: Artificial Sequence
<220> FEATURE:
<223> OTHER INFORMATION: Synthetic construct

<400> SEQUENCE: 28
ctgacgaaac ctcgctccgg cggggttttt tgttatctgc aattcagtac tgtgacggaa    60
gatcacttcg ca                                                        72

<210> SEQ ID NO 29
```

-continued

```
<211> LENGTH: 75
<212> TYPE: DNA
<213> ORGANISM: Artificial Sequence
<220> FEATURE:
<223> OTHER INFORMATION: Synthetic construct

<400> SEQUENCE: 29
tctgcgccgg taaagcgctt acgcgtcgat gttgtgcccg aacttgccat ttatttgtta      60
actgttaatt gtcct                                                       75

<210> SEQ ID NO 30
<211> LENGTH: 70
<212> TYPE: DNA
<213> ORGANISM: Artificial Sequence
<220> FEATURE:
<223> OTHER INFORMATION: Synthetic construct

<400> SEQUENCE: 30
ctgacgaaac ctcgctccgg cggggttttt tgttatctgc aattcagtac ttatctctgg      60
cggtgttgac                                                             70

<210> SEQ ID NO 31
<211> LENGTH: 70
<212> TYPE: DNA
<213> ORGANISM: Artificial Sequence
<220> FEATURE:
<223> OTHER INFORMATION: Synthetic construct

<400> SEQUENCE: 31
tctgcgccgg taaagcgctt acgcgtcgat gttgtgcccg aacttgccat agctgtttcc      60
tggtttaaac                                                             70

<210> SEQ ID NO 32
<211> LENGTH: 22
<212> TYPE: DNA
<213> ORGANISM: Artificial Sequence
<220> FEATURE:
<223> OTHER INFORMATION: Synthetic construct

<400> SEQUENCE: 32
gttctgcgcg gaacacgtat ac                                               22

<210> SEQ ID NO 33
<211> LENGTH: 20
<212> TYPE: DNA
<213> ORGANISM: Artificial Sequence
<220> FEATURE:
<223> OTHER INFORMATION: Synthetic construct

<400> SEQUENCE: 33
ccgctacagg ccatacagac                                                  20

<210> SEQ ID NO 34
<211> LENGTH: 72
<212> TYPE: DNA
<213> ORGANISM: Artificial Sequence
<220> FEATURE:
<223> OTHER INFORMATION: Synthetic construct

<400> SEQUENCE: 34
tgaactaaga ggaagggaac aacattcaga ccgaaattga attttttttca tgtgacggaa      60 gatcacttcg ca                                                          72
```

-continued

```
<210> SEQ ID NO 35
<211> LENGTH: 75
<212> TYPE: DNA
<213> ORGANISM: Artificial Sequence
<220> FEATURE:
<223> OTHER INFORMATION: Synthetic construct

<400> SEQUENCE: 35
ttcacaccct gtgcccgcaa cgcatgtacc acccactgtg cgccattcat ttatttgtta     60
actgttaatt gtcct                                                      75

<210> SEQ ID NO 36
<211> LENGTH: 70
<212> TYPE: DNA
<213> ORGANISM: Artificial Sequence
<220> FEATURE:
<223> OTHER INFORMATION: Synthetic construct

<400> SEQUENCE: 36
tgaactaaga ggaagggaac aacattcaga ccgaaattga attttttttca ttatctctgg    60 cggtgttgac                                                            70

<210> SEQ ID NO 37
<211> LENGTH: 71
<212> TYPE: DNA
<213> ORGANISM: Artificial Sequence
<220> FEATURE:
<223> OTHER INFORMATION: Synthetic construct

<400> SEQUENCE: 37
ttcacaccct gtgcccgcaa cgcatgtacc acccactgtg cgccattcat agctgtttcc     60
tggtttaaac g                                                          71

<210> SEQ ID NO 38
<211> LENGTH: 22
<212> TYPE: DNA
<213> ORGANISM: Artificial Sequence
<220> FEATURE:
<223> OTHER INFORMATION: Synthetic construct

<400> SEQUENCE: 38
gcataagata tcgctgctgt ag                                              22

<210> SEQ ID NO 39
<211> LENGTH: 20
<212> TYPE: DNA
<213> ORGANISM: Artificial Sequence
<220> FEATURE:
<223> OTHER INFORMATION: Synthetic construct

<400> SEQUENCE: 39
gccagttttg ccagtagcac                                                 20

<210> SEQ ID NO 40
<211> LENGTH: 72
<212> TYPE: DNA
<213> ORGANISM: Artificial Sequence
<220> FEATURE:
<223> OTHER INFORMATION: Synthetic construct

<400> SEQUENCE: 40
agaacctgat tatgcgccgg atattatcag tcttactcga aaatgaatca tgtgacggaa     60
gatcacttcg ca                                                         72
```

-continued

```
<210> SEQ ID NO 41
<211> LENGTH: 75
<212> TYPE: DNA
<213> ORGANISM: Artificial Sequence
<220> FEATURE:
<223> OTHER INFORMATION: Synthetic construct

<400> SEQUENCE: 41
ttcatcgccc acggtctgga tggtcatacg cgataatgtc ggatcgtcgg ttatttgtta      60
actgttaatt gtcct                                                       75

<210> SEQ ID NO 42
<211> LENGTH: 74
<212> TYPE: DNA
<213> ORGANISM: Artificial Sequence
<220> FEATURE:
<223> OTHER INFORMATION: Synthetic construct

<400> SEQUENCE: 42
agaacctgat tatgcgccgg atattatcag tcttactcga aaatgaatca gacgcgttat      60
tccgcgtgat tggc                                                        74

<210> SEQ ID NO 43
<211> LENGTH: 21
<212> TYPE: DNA
<213> ORGANISM: Artificial Sequence
<220> FEATURE:
<223> OTHER INFORMATION: Synthetic construct

<400> SEQUENCE: 43
cacaccagag cgagcaacct c                                                21

<210> SEQ ID NO 44
<211> LENGTH: 23
<212> TYPE: DNA
<213> ORGANISM: Artificial Sequence
<220> FEATURE:
<223> OTHER INFORMATION: Synthetic construct

<400> SEQUENCE: 44
atgagctgga aagcaaactt agc                                              23

<210> SEQ ID NO 45
<211> LENGTH: 72
<212> TYPE: DNA
<213> ORGANISM: Artificial Sequence
<220> FEATURE:
<223> OTHER INFORMATION: Synthetic construct

<400> SEQUENCE: 45
ataactctaa tgtttaaact cttttagtaa atcacagtga gtgtgagcgc tgtgacggaa      60
gatcacttcg ca                                                          72

<210> SEQ ID NO 46
<211> LENGTH: 75
<212> TYPE: DNA
<213> ORGANISM: Artificial Sequence
<220> FEATURE:
<223> OTHER INFORMATION: Synthetic construct

<400> SEQUENCE: 46
ccgtttatgt tgccagacag cgctactgat taagcggatt ttttcgcttt ttatttgtta      60
actgttaatt gtcct                                                       75
```

-continued

```
<210> SEQ ID NO 47
<211> LENGTH: 70
<212> TYPE: DNA
<213> ORGANISM: Artificial Sequence
<220> FEATURE:
<223> OTHER INFORMATION: Synthetic construct

<400> SEQUENCE: 47
ataactctaa tgtttaaact cttttagtaa atcacagtga gtgtgagcgc atggctaact       60
acttcaatac                                                               70

<210> SEQ ID NO 48
<211> LENGTH: 71
<212> TYPE: DNA
<213> ORGANISM: Artificial Sequence
<220> FEATURE:
<223> OTHER INFORMATION: Synthetic construct

<400> SEQUENCE: 48
ccgtttatgt tgccagacag cgctactgat taagcggatt ttttcgcttt ttaacccgca       60
acagcaatac g                                                             71

<210> SEQ ID NO 49
<211> LENGTH: 21
<212> TYPE: DNA
<213> ORGANISM: Artificial Sequence
<220> FEATURE:
<223> OTHER INFORMATION: Synthetic construct

<400> SEQUENCE: 49
catgctaatg tagccaccaa a                                                  21

<210> SEQ ID NO 50
<211> LENGTH: 20
<212> TYPE: DNA
<213> ORGANISM: Artificial Sequence
<220> FEATURE:
<223> OTHER INFORMATION: Synthetic construct

<400> SEQUENCE: 50
ttgcaccacc atccagataa                                                    20

<210> SEQ ID NO 51
<211> LENGTH: 75
<212> TYPE: DNA
<213> ORGANISM: Artificial Sequence
<220> FEATURE:
<223> OTHER INFORMATION: Synthetic construct

<400> SEQUENCE: 51
agctgtgcca gctgctggcg cagattcagt gtattgaagt agttagccat ttatttgtta       60
actgttaatt gtcct                                                         75

<210> SEQ ID NO 52
<211> LENGTH: 70
<212> TYPE: DNA
<213> ORGANISM: Artificial Sequence
<220> FEATURE:
<223> OTHER INFORMATION: Synthetic construct

<400> SEQUENCE: 52
ataactctaa tgtttaaact cttttagtaa atcacagtga gtgtgagcgc ttatctctgg       60
```

-continued

```
cggtgttgac                                                              70

<210> SEQ ID NO 53
<211> LENGTH: 72
<212> TYPE: DNA
<213> ORGANISM: Artificial Sequence
<220> FEATURE:
<223> OTHER INFORMATION: Synthetic construct

<400> SEQUENCE: 53
agctgtgcca gctgctggcg cagattcagt gtattgaagt agttagccat agctgtttcc     60
tggtttaaac cg                                                          72

<210> SEQ ID NO 54
<211> LENGTH: 20
<212> TYPE: DNA
<213> ORGANISM: Artificial Sequence
<220> FEATURE:
<223> OTHER INFORMATION: Synthetic construct

<400> SEQUENCE: 54
cgcactacat cagagtgctg                                                  20

<210> SEQ ID NO 55
<211> LENGTH: 73
<212> TYPE: DNA
<213> ORGANISM: Artificial Sequence
<220> FEATURE:
<223> OTHER INFORMATION: Synthetic construct

<400> SEQUENCE: 55
aaacgaccac cattaatggt tgtcgaagta cgcagtaaat aaaaaatcca tgtgacggaa     60
gatcacttcg cag                                                         73

<210> SEQ ID NO 56
<211> LENGTH: 75
<212> TYPE: DNA
<213> ORGANISM: Artificial Sequence
<220> FEATURE:
<223> OTHER INFORMATION: Synthetic construct

<400> SEQUENCE: 56
cggtccgaac ggcgcgccag cacgacgacc gtctggggtg ttacccgttt ttatttgtta     60
actgttaatt gtcct                                                       75

<210> SEQ ID NO 57
<211> LENGTH: 70
<212> TYPE: DNA
<213> ORGANISM: Artificial Sequence
<220> FEATURE:
<223> OTHER INFORMATION: Synthetic construct

<400> SEQUENCE: 57
aaacgaccac cattaatggt tgtcgaagta cgcagtaaat aaaaaatcca atgcctaagt     60
accgttccgc                                                             70

<210> SEQ ID NO 58
<211> LENGTH: 74
<212> TYPE: DNA
<213> ORGANISM: Artificial Sequence
<220> FEATURE:
<223> OTHER INFORMATION: Synthetic construct

<400> SEQUENCE: 58
```

-continued

```
cggtccgaac ggcgcgccag cacgacgacc gtctggggtg ttacccgttt ttaacccccc      60
agtttcgatt tatc                                                        74

<210> SEQ ID NO 59
<211> LENGTH: 21
<212> TYPE: DNA
<213> ORGANISM: Artificial Sequence
<220> FEATURE:
<223> OTHER INFORMATION: Synthetic construct

<400> SEQUENCE: 59
ctgcggagcc gatctcttta c                                                21

<210> SEQ ID NO 60
<211> LENGTH: 22
<212> TYPE: DNA
<213> ORGANISM: Artificial Sequence
<220> FEATURE:
<223> OTHER INFORMATION: Synthetic construct

<400> SEQUENCE: 60
cgagtaataa cgtcctgctg ct                                               22

<210> SEQ ID NO 61
<211> LENGTH: 75
<212> TYPE: DNA
<213> ORGANISM: Artificial Sequence
<220> FEATURE:
<223> OTHER INFORMATION: Synthetic construct

<400> SEQUENCE: 61
cccgccatat tacgaccatg agtggtggtg gcggaacggt acttaggcat ttatttgtta      60
actgttaatt gtcct                                                       75

<210> SEQ ID NO 62
<211> LENGTH: 70
<212> TYPE: DNA
<213> ORGANISM: Artificial Sequence
<220> FEATURE:
<223> OTHER INFORMATION: Synthetic construct

<400> SEQUENCE: 62
aaacgaccac cattaatggt tgtcgaagta cgcagtaaat aaaaaatcca ttatctctgg      60
cggtgttgac                                                             70

<210> SEQ ID NO 63
<211> LENGTH: 78
<212> TYPE: DNA
<213> ORGANISM: Artificial Sequence
<220> FEATURE:
<223> OTHER INFORMATION: Synthetic construct

<400> SEQUENCE: 63
cccgccatat tacgaccatg agtggtggtg gcggaacggt acttaggcat tgctgacctc      60
ctggtttaaa cgtacatg                                                    78

<210> SEQ ID NO 64
<211> LENGTH: 20
<212> TYPE: DNA
<213> ORGANISM: Artificial Sequence
<220> FEATURE:
<223> OTHER INFORMATION: Synthetic construct
```

-continued

```
<400> SEQUENCE: 64
caaccagatc gagcttgatg                                              20

<210> SEQ ID NO 65
<211> LENGTH: 20
<212> TYPE: DNA
<213> ORGANISM: Artificial Sequence
<220> FEATURE:
<223> OTHER INFORMATION: Synthetic construct

<400> SEQUENCE: 65
tgcagaaaac catcgacaag                                              20

<210> SEQ ID NO 66
<211> LENGTH: 20
<212> TYPE: DNA
<213> ORGANISM: Artificial Sequence
<220> FEATURE:
<223> OTHER INFORMATION: Synthetic construct

<400> SEQUENCE: 66
caccaatcag cgtgacaact                                              20

<210> SEQ ID NO 67
<211> LENGTH: 72
<212> TYPE: DNA
<213> ORGANISM: Artificial Sequence
<220> FEATURE:
<223> OTHER INFORMATION: Synthetic construct

<400> SEQUENCE: 67
gaaggcgaat ggctgagatg aaaaacctga aaattgaggt ggtgcgctat tgtgacggaa    60
gatcacttcg ca                                                      72

<210> SEQ ID NO 68
<211> LENGTH: 75
<212> TYPE: DNA
<213> ORGANISM: Artificial Sequence
<220> FEATURE:
<223> OTHER INFORMATION: Synthetic construct

<400> SEQUENCE: 68
tctcaggctc cttaccagta cagggcaaca aacaggatta cgatggtggc ttatttgtta    60
actgttaatt gtcct                                                   75

<210> SEQ ID NO 69
<211> LENGTH: 70
<212> TYPE: DNA
<213> ORGANISM: Artificial Sequence
<220> FEATURE:
<223> OTHER INFORMATION: Synthetic construct

<400> SEQUENCE: 69
gaaggcgaat ggctgagatg aaaaacctga aaattgaggt ggtgcgctat atgaaaccga    60
ccaccatctc                                                         70

<210> SEQ ID NO 70
<211> LENGTH: 73
<212> TYPE: DNA
<213> ORGANISM: Artificial Sequence
<220> FEATURE:
<223> OTHER INFORMATION: Synthetic construct

<400> SEQUENCE: 70
```

-continued

```
tctcaggctc cttaccagta cagggcaaca aacaggatta cgatggtggc ttaatggaaa      60
ctgtgttctt cgc                                                         73

<210> SEQ ID NO 71
<211> LENGTH: 75
<212> TYPE: DNA
<213> ORGANISM: Artificial Sequence
<220> FEATURE:
<223> OTHER INFORMATION: Synthetic construct

<400> SEQUENCE: 71 ttttttttcct gtttgtactt ctgcagtaag gagatggtgg tcggtttcat ttatttgtta    60
actgttaatt gtcct                                                      75

<210> SEQ ID NO 72
<211> LENGTH: 70
<212> TYPE: DNA
<213> ORGANISM: Artificial Sequence
<220> FEATURE:
<223> OTHER INFORMATION: Synthetic construct

<400> SEQUENCE: 72
gaaggcgaat ggctgagatg aaaaacctga aaattgaggt ggtgcgctat ttatctctgg      60
cggtgttgac                                                            70

<210> SEQ ID NO 73
<211> LENGTH: 70
<212> TYPE: DNA
<213> ORGANISM: Artificial Sequence
<220> FEATURE:
<223> OTHER INFORMATION: Synthetic construct

<400> SEQUENCE: 73 ttttttttcct gtttgtactt ctgcagtaag gagatggtgg tcggtttcat agctgtttcc     60
tggtttaaac                                                            70

<210> SEQ ID NO 74
<211> LENGTH: 20
<212> TYPE: DNA
<213> ORGANISM: Artificial Sequence
<220> FEATURE:
<223> OTHER INFORMATION: Synthetic construct

<400> SEQUENCE: 74
ccaccagcat gacgttaagc                                                 20

<210> SEQ ID NO 75
<211> LENGTH: 73
<212> TYPE: DNA
<213> ORGANISM: Artificial Sequence
<220> FEATURE:
<223> OTHER INFORMATION: Synthetic construct

<400> SEQUENCE: 75
attatatttg aaattttgta aaatattttt agtagcttaa atgtgattca tgtgacggaa      60
gatcacttcg cag                                                        73

<210> SEQ ID NO 76
<211> LENGTH: 75
<212> TYPE: DNA
<213> ORGANISM: Artificial Sequence
<220> FEATURE:
```

-continued

```
<223> OTHER INFORMATION: Synthetic construct

<400> SEQUENCE: 76
aaccagttcg ttcgggcagg tttcgccttt ttccagagca tgagctccta ttatttgtta    60
actgttaatt gtcct                                                      75

<210> SEQ ID NO 77
<211> LENGTH: 70
<212> TYPE: DNA
<213> ORGANISM: Artificial Sequence
<220> FEATURE:
<223> OTHER INFORMATION: Synthetic construct

<400> SEQUENCE: 77
attatatttg aaattttgta aaatattttt agtagcttaa atgtgattca atgaaaatta    60
ccgtattggg                                                           70

<210> SEQ ID NO 78
<211> LENGTH: 70
<212> TYPE: DNA
<213> ORGANISM: Artificial Sequence
<220> FEATURE:
<223> OTHER INFORMATION: Synthetic construct

<400> SEQUENCE: 78
aaccagttcg ttcgggcagg tttcgccttt ttccagagca tgagctccta ctaccagggg    60
cgaggcaaac                                                           70

<210> SEQ ID NO 79
<211> LENGTH: 20
<212> TYPE: DNA
<213> ORGANISM: Artificial Sequence
<220> FEATURE:
<223> OTHER INFORMATION: Synthetic construct

<400> SEQUENCE: 79
gataacggag atcgggaatg                                                 20

<210> SEQ ID NO 80
<211> LENGTH: 20
<212> TYPE: DNA
<213> ORGANISM: Artificial Sequence
<220> FEATURE:
<223> OTHER INFORMATION: Synthetic construct

<400> SEQUENCE: 80
ctttggctgt cagttcacca                                                 20

<210> SEQ ID NO 81
<211> LENGTH: 75
<212> TYPE: DNA
<213> ORGANISM: Artificial Sequence
<220> FEATURE:
<223> OTHER INFORMATION: Synthetic construct

<400> SEQUENCE: 81
gtaagccata attgccctaa ggcaccgcat cccaatacgg taattttcat ttatttgtta    60
actgttaatt gtcct                                                      75

<210> SEQ ID NO 82
<211> LENGTH: 70
<212> TYPE: DNA
<213> ORGANISM: Artificial Sequence
```

<220> FEATURE:
<223> OTHER INFORMATION: Synthetic construct

<400> SEQUENCE: 82
attatatttg aaattttgta aaatattttt agtagcttaa atgtgattca ttatctctgg    60
cggtgttgac                                                          70

<210> SEQ ID NO 83
<211> LENGTH: 71
<212> TYPE: DNA
<213> ORGANISM: Artificial Sequence
<220> FEATURE:
<223> OTHER INFORMATION: Synthetic construct

<400> SEQUENCE: 83
gtaagccata attgccctaa ggcaccgcat cccaatacgg taattttcat tcgaaccctc    60
ctggtttaaa c                                                        71

<210> SEQ ID NO 84
<211> LENGTH: 20
<212> TYPE: DNA
<213> ORGANISM: Artificial Sequence
<220> FEATURE:
<223> OTHER INFORMATION: Synthetic construct

<400> SEQUENCE: 84
cttttgacgg catcggaaac                                               20

<210> SEQ ID NO 85
<211> LENGTH: 73
<212> TYPE: DNA
<213> ORGANISM: Artificial Sequence
<220> FEATURE:
<223> OTHER INFORMATION: Synthetic construct

<400> SEQUENCE: 85
gtaggaaagt taactacgga tgtacattat ggaactgacg actcgcactt tgtgacggaa    60
gatcacttcg cag                                                      73

<210> SEQ ID NO 86
<211> LENGTH: 75
<212> TYPE: DNA
<213> ORGANISM: Artificial Sequence
<220> FEATURE:
<223> OTHER INFORMATION: Synthetic construct

<400> SEQUENCE: 86
gcgtttgcca cctgtgcaat attacttcag acggtccgcg agataacgct ttatttgtta    60
actgttaatt gtcct                                                    75

<210> SEQ ID NO 87
<211> LENGTH: 20
<212> TYPE: DNA
<213> ORGANISM: Artificial Sequence
<220> FEATURE:
<223> OTHER INFORMATION: Synthetic construct

<400> SEQUENCE: 87
cagctcatca accaggtcaa                                               20

<210> SEQ ID NO 88
<211> LENGTH: 20
<212> TYPE: DNA

-continued

```
<213> ORGANISM: Artificial Sequence
<220> FEATURE:
<223> OTHER INFORMATION: Synthetic construct

<400> SEQUENCE: 88
aaaagccgtc acgttattgg                                               20

<210> SEQ ID NO 89
<211> LENGTH: 71
<212> TYPE: DNA
<213> ORGANISM: Artificial Sequence
<220> FEATURE:
<223> OTHER INFORMATION: Synthetic construct

<400> SEQUENCE: 89
gtaggaaagt taactacgga tgtacattat ggaactgacg actcgcactt atgttaaagc   60
gtgaaatgaa c                                                        71

<210> SEQ ID NO 90
<211> LENGTH: 70
<212> TYPE: DNA
<213> ORGANISM: Artificial Sequence
<220> FEATURE:
<223> OTHER INFORMATION: Synthetic construct

<400> SEQUENCE: 90
gcgtttgcca cctgtgcaat attacttcag acggtccgcg agataacgct ttatgcgtaa   60
accgggtaac                                                          70

<210> SEQ ID NO 91
<211> LENGTH: 75
<212> TYPE: DNA
<213> ORGANISM: Artificial Sequence
<220> FEATURE:
<223> OTHER INFORMATION: Synthetic construct

<400> SEQUENCE: 91
tgccacagtt cggcatcata atcggcaatg ttcatttcac gctttaacat ttatttgtta   60
actgttaatt gtcct                                                    75

<210> SEQ ID NO 92
<211> LENGTH: 70
<212> TYPE: DNA
<213> ORGANISM: Artificial Sequence
<220> FEATURE:
<223> OTHER INFORMATION: Synthetic construct

<400> SEQUENCE: 92
gtaggaaagt taactacgga tgtacattat ggaactgacg actcgcactt ttatctctgg   60
cggtgttgac                                                          70

<210> SEQ ID NO 93
<211> LENGTH: 70
<212> TYPE: DNA
<213> ORGANISM: Artificial Sequence
<220> FEATURE:
<223> OTHER INFORMATION: Synthetic construct

<400> SEQUENCE: 93
tgccacagtt cggcatcata atcggcaatg ttcatttcac gctttaacat agctgtttcc   60
tggtttaaac                                                          70
```

```
<210> SEQ ID NO 94
<211> LENGTH: 20
<212> TYPE: DNA
<213> ORGANISM: Artificial Sequence
<220> FEATURE:
<223> OTHER INFORMATION: Synthetic construct

<400> SEQUENCE: 94
ccaggttcat acccagaacg                                                      20

<210> SEQ ID NO 95
<211> LENGTH: 72
<212> TYPE: DNA
<213> ORGANISM: Artificial Sequence
<220> FEATURE:
<223> OTHER INFORMATION: Synthetic construct

<400> SEQUENCE: 95
ttgatttagt gtttttttgac attttttttag ctcttaatat tgtcttattc tgtgacggaa        60
gatcacttcg ca                                                              72

<210> SEQ ID NO 96
<211> LENGTH: 75
<212> TYPE: DNA
<213> ORGANISM: Artificial Sequence
<220> FEATURE:
<223> OTHER INFORMATION: Synthetic construct

<400> SEQUENCE: 96
cgagcgccgc aaagcgtgtg ttgttcgtac aaaggagtct gttgtgccat ttatttgtta         60
actgttaatt gtcct                                                           75

<210> SEQ ID NO 97
<211> LENGTH: 70
<212> TYPE: DNA
<213> ORGANISM: Artificial Sequence
<220> FEATURE:
<223> OTHER INFORMATION: Synthetic construct

<400> SEQUENCE: 97
ttgatttagt gtttttttgac attttttttag ctcttaatat tgtcttattc ttatctctgg        60
cggtgttgac                                                                 70

<210> SEQ ID NO 98
<211> LENGTH: 71
<212> TYPE: DNA
<213> ORGANISM: Artificial Sequence
<220> FEATURE:
<223> OTHER INFORMATION: Synthetic construct

<400> SEQUENCE: 98
cgagcgccgc aaagcgtgtg ttgttcgtac aaaggagtct gttgtgccat agctgtttcc         60
tggtttaaac g                                                               71

<210> SEQ ID NO 99
<211> LENGTH: 20
<212> TYPE: DNA
<213> ORGANISM: Artificial Sequence
<220> FEATURE:
<223> OTHER INFORMATION: Synthetic construct

<400> SEQUENCE: 99
ccaggcaatg ggattaaacg                                                      20
```

```
<210> SEQ ID NO 100
<211> LENGTH: 20
<212> TYPE: DNA
<213> ORGANISM: Artificial Sequence
<220> FEATURE:
<223> OTHER INFORMATION: Synthetic construct

<400> SEQUENCE: 100
gtggcggagt taacaacgag                                               20

<210> SEQ ID NO 101
<211> LENGTH: 72
<212> TYPE: DNA
<213> ORGANISM: Artificial Sequence
<220> FEATURE:
<223> OTHER INFORMATION: Synthetic construct

<400> SEQUENCE: 101
aatcactgct ggatgcgacc gcatacgaag cattgttaga agacgagtaa tgtgacggaa     60
gatcacttcg ca                                                       72

<210> SEQ ID NO 102
<211> LENGTH: 75
<212> TYPE: DNA
<213> ORGANISM: Artificial Sequence
<220> FEATURE:
<223> OTHER INFORMATION: Synthetic construct

<400> SEQUENCE: 102
cgttcaataa aagcgccgct gttttcaagc tggcttaacg tctgtgtcat ttatttgtta     60
actgttaatt gtcct                                                    75

<210> SEQ ID NO 103
<211> LENGTH: 70
<212> TYPE: DNA
<213> ORGANISM: Artificial Sequence
<220> FEATURE:
<223> OTHER INFORMATION: Synthetic construct

<400> SEQUENCE: 103
aatcactgct ggatgcgacc gcatacgaag cattgttaga agacgagtaa ttatctctgg     60
cggtgttgac                                                          70

<210> SEQ ID NO 104
<211> LENGTH: 71
<212> TYPE: DNA
<213> ORGANISM: Artificial Sequence
<220> FEATURE:
<223> OTHER INFORMATION: Synthetic construct

<400> SEQUENCE: 104
cgttcaataa aagcgccgct gttttcaagc tggcttaacg tctgtgtcat agctgtttcc     60
tggtttaaac g                                                        71

<210> SEQ ID NO 105
<211> LENGTH: 22
<212> TYPE: DNA
<213> ORGANISM: Artificial Sequence
<220> FEATURE:
<223> OTHER INFORMATION: Synthetic construct

<400> SEQUENCE: 105
atgagcaacg taccagcaga ac                                            22
```

-continued

```
<210> SEQ ID NO 106
<211> LENGTH: 21
<212> TYPE: DNA
<213> ORGANISM: Artificial Sequence
<220> FEATURE:
<223> OTHER INFORMATION: Synthetic construct

<400> SEQUENCE: 106
gaagttgagc agtgcttcaa g                                            21

<210> SEQ ID NO 107
<211> LENGTH: 73
<212> TYPE: DNA
<213> ORGANISM: Artificial Sequence
<220> FEATURE:
<223> OTHER INFORMATION: Synthetic construct

<400> SEQUENCE: 107
aggtacttcc atgtcgagta agttagtact ggttctgaac tgcggtagtt tgtgacggaa   60
gatcacttcg cag                                                     73

<210> SEQ ID NO 108
<211> LENGTH: 75
<212> TYPE: DNA
<213> ORGANISM: Artificial Sequence
<220> FEATURE:
<223> OTHER INFORMATION: Synthetic construct

<400> SEQUENCE: 108
ggtcggcaga acgctgtacc gctttgtagg tggtgttacc ggtgttcaga ttatttgtta   60
actgttaatt gtcct                                                   75

<210> SEQ ID NO 109
<211> LENGTH: 72
<212> TYPE: DNA
<213> ORGANISM: Artificial Sequence
<220> FEATURE:
<223> OTHER INFORMATION: Synthetic construct

<400> SEQUENCE: 109
aggtacttcc atgtcgagta agttagtact ggttctgaac tgcggtagtt atgcccatgt   60
caggcattga tg                                                      72

<210> SEQ ID NO 110
<211> LENGTH: 70
<212> TYPE: DNA
<213> ORGANISM: Artificial Sequence
<220> FEATURE:
<223> OTHER INFORMATION: Synthetic construct

<400> SEQUENCE: 110
ggtcggcaga acgctgtacc gctttgtagg tggtgttacc ggtgttcaga ttaaaaggac   60
tccgcttcgc                                                         70

<210> SEQ ID NO 111
<211> LENGTH: 20
<212> TYPE: DNA
<213> ORGANISM: Artificial Sequence
<220> FEATURE:
<223> OTHER INFORMATION: Synthetic construct

<400> SEQUENCE: 111
```

-continued cgggacaacg ttcaaaacat                                                      20

<210> SEQ ID NO 112
<211> LENGTH: 20
<212> TYPE: DNA
<213> ORGANISM: Artificial Sequence
<220> FEATURE:
<223> OTHER INFORMATION: Synthetic construct

<400> SEQUENCE: 112
attgcccatc ttcttgttgg                                                      20

<210> SEQ ID NO 113
<211> LENGTH: 70
<212> TYPE: DNA
<213> ORGANISM: Artificial Sequence
<220> FEATURE:
<223> OTHER INFORMATION: Synthetic construct

<400> SEQUENCE: 113
aggtacttcc atgtcgagta agttagtact ggttctgaac tgcggtagtt ttatctctgg         60
cggtgttgac                                                                 70

<210> SEQ ID NO 114
<211> LENGTH: 70
<212> TYPE: DNA
<213> ORGANISM: Artificial Sequence
<220> FEATURE:
<223> OTHER INFORMATION: Synthetic construct

<400> SEQUENCE: 114
cggaaatgac gggtgcggat tttctttgca tcaatgcctg acatgggcat agctgtttcc         60
tggtttaaac                                                                 70

<210> SEQ ID NO 115
<211> LENGTH: 75
<212> TYPE: DNA
<213> ORGANISM: Artificial Sequence
<220> FEATURE:
<223> OTHER INFORMATION: Synthetic construct

<400> SEQUENCE: 115
cggaaatgac gggtgcggat tttctttgca tcaatgcctg acatgggcat ttatttgtta         60
actgttaatt gtcct                                                           75

<210> SEQ ID NO 116
<211> LENGTH: 20
<212> TYPE: DNA
<213> ORGANISM: Artificial Sequence
<220> FEATURE:
<223> OTHER INFORMATION: Synthetic construct

<400> SEQUENCE: 116
accggaattc cagcatcaac                                                      20

<210> SEQ ID NO 117
<211> LENGTH: 72
<212> TYPE: DNA
<213> ORGANISM: Artificial Sequence
<220> FEATURE:
<223> OTHER INFORMATION: Synthetic construct

<400> SEQUENCE: 117
cacaaccaca tcacaacaaa tccgcgcctg agcgcaaaag gaatataaaa tgtgacggaa         60
gatcacttcg ca                                                                    72

<210> SEQ ID NO 118
<211> LENGTH: 75
<212> TYPE: DNA
<213> ORGANISM: Artificial Sequence
<220> FEATURE:
<223> OTHER INFORMATION: Synthetic construct

<400> SEQUENCE: 118
cgaaccatct ccccattgaa ccaaatgtaa tcagctttct tcgtggtcat ttatttgtta           60
actgttaatt gtcct                                                                 75

<210> SEQ ID NO 119
<211> LENGTH: 74
<212> TYPE: DNA
<213> ORGANISM: Artificial Sequence
<220> FEATURE:
<223> OTHER INFORMATION: Synthetic construct

<400> SEQUENCE: 119
cacaaccaca tcacaacaaa tccgcgcctg agcgcaaaag gaatataaaa gtgaccacga           60
agaaagctga ttac                                                                  74

<210> SEQ ID NO 120
<211> LENGTH: 27
<212> TYPE: DNA
<213> ORGANISM: Artificial Sequence
<220> FEATURE:
<223> OTHER INFORMATION: Synthetic construct

<400> SEQUENCE: 120
ttattgatta acttgatcta accagcc                                                    27

<210> SEQ ID NO 121
<211> LENGTH: 22
<212> TYPE: DNA
<213> ORGANISM: Artificial Sequence
<220> FEATURE:
<223> OTHER INFORMATION: Synthetic construct

<400> SEQUENCE: 121
atgatgcaac atcaggtcaa tg                                                         22

<210> SEQ ID NO 122
<211> LENGTH: 72
<212> TYPE: DNA
<213> ORGANISM: Artificial Sequence
<220> FEATURE:
<223> OTHER INFORMATION: Synthetic construct

<400> SEQUENCE: 122
gccgaaaacc cgaacgcgat gttcgtattg tggaaagacc acactgcggt tgtgacggaa           60
gatcacttcg ca                                                                    72

<210> SEQ ID NO 123
<211> LENGTH: 75
<212> TYPE: DNA
<213> ORGANISM: Artificial Sequence
<220> FEATURE:
<223> OTHER INFORMATION: Synthetic construct

<400> SEQUENCE: 123

-continued

```
tcacgcatgt tatcgccaaa acggcagact ttcagatgac gggtatcctg ttatttgtta      60
actgttaatt gtcct                                                        75

<210> SEQ ID NO 124
<211> LENGTH: 70
<212> TYPE: DNA
<213> ORGANISM: Artificial Sequence
<220> FEATURE:
<223> OTHER INFORMATION: Synthetic construct

<400> SEQUENCE: 124
gccgaaaacc cgaacgcgat gttcgtattg tggaaagacc acactgcggt atgagccaga      60
atggccgtcc                                                              70

<210> SEQ ID NO 125
<211> LENGTH: 71
<212> TYPE: DNA
<213> ORGANISM: Artificial Sequence
<220> FEATURE:
<223> OTHER INFORMATION: Synthetic construct

<400> SEQUENCE: 125
tcacgcatgt tatcgccaaa acggcagact ttcagatgac gggtatcctg ttaagccaga      60
tccatccaca c                                                            71

<210> SEQ ID NO 126
<211> LENGTH: 20
<212> TYPE: DNA
<213> ORGANISM: Artificial Sequence
<220> FEATURE:
<223> OTHER INFORMATION: Synthetic construct

<400> SEQUENCE: 126
caccagcgta gagtggtatc                                                   20

<210> SEQ ID NO 127
<211> LENGTH: 21
<212> TYPE: DNA
<213> ORGANISM: Artificial Sequence
<220> FEATURE:
<223> OTHER INFORMATION: Synthetic construct

<400> SEQUENCE: 127
ctgcagaccg gttgacatca c                                                 21

<210> SEQ ID NO 128
<211> LENGTH: 75
<212> TYPE: DNA
<213> ORGANISM: Artificial Sequence
<220> FEATURE:
<223> OTHER INFORMATION: Synthetic construct

<400> SEQUENCE: 128
tgcgcaagct tatcggcgat gaggactacc ggacggccat tctggctcat ttatttgtta      60
actgttaatt gtcct                                                        75

<210> SEQ ID NO 129
<211> LENGTH: 70
<212> TYPE: DNA
<213> ORGANISM: Artificial Sequence
<220> FEATURE:
<223> OTHER INFORMATION: Synthetic construct

<400> SEQUENCE: 129
```

-continued

```
gccgaaaacc cgaacgcgat gttcgtattg tggaaagacc acactgcggt ttatctctgg     60
cggtgttgac                                                            70

<210> SEQ ID NO 130
<211> LENGTH: 70
<212> TYPE: DNA
<213> ORGANISM: Artificial Sequence
<220> FEATURE:
<223> OTHER INFORMATION: Synthetic construct

<400> SEQUENCE: 130
tgcgcaagct tatcggcgat gaggactacc ggacggccat tctggctcat agctgtttcc     60
tggtttaaac                                                            70

<210> SEQ ID NO 131
<211> LENGTH: 20
<212> TYPE: DNA
<213> ORGANISM: Artificial Sequence
<220> FEATURE:
<223> OTHER INFORMATION: Synthetic construct

<400> SEQUENCE: 131
tctggcgagc agtagacagc                                                 20

<210> SEQ ID NO 132
<211> LENGTH: 72
<212> TYPE: DNA
<213> ORGANISM: Artificial Sequence
<220> FEATURE:
<223> OTHER INFORMATION: Synthetic construct

<400> SEQUENCE: 132
atgacattct ccctttttgg tgacaaattt acccgccact ccggcattac tgtgacggaa     60
gatcacttcg ca                                                         72

<210> SEQ ID NO 133
<211> LENGTH: 75
<212> TYPE: DNA
<213> ORGANISM: Artificial Sequence
<220> FEATURE:
<223> OTHER INFORMATION: Synthetic construct

<400> SEQUENCE: 133
ttagtgactt tcagcccagg ctctttctat ctcttccgcc agaatcttca ttatttgtta     60
actgttaatt gtcct                                                      75

<210> SEQ ID NO 134
<211> LENGTH: 64
<212> TYPE: DNA
<213> ORGANISM: Artificial Sequence
<220> FEATURE:
<223> OTHER INFORMATION: Synthetic construct

<400> SEQUENCE: 134
gcaccaggta atgttaggca tgtttgttct ccttttgtcg acttaaccgt gacggcgttc     60
gaac                                                                  64

<210> SEQ ID NO 135
<211> LENGTH: 64
<212> TYPE: DNA
<213> ORGANISM: Artificial Sequence
<220> FEATURE:
```

<223> OTHER INFORMATION: Synthetic construct

<400> SEQUENCE: 135
gttcgaacgc cgtcacggtt aagtcgacaa aaggagaaca aacatgccta acattacctg      60
gtgc      64

<210> SEQ ID NO 136
<211> LENGTH: 73
<212> TYPE: DNA
<213> ORGANISM: Artificial Sequence
<220> FEATURE:
<223> OTHER INFORMATION: Synthetic construct

<400> SEQUENCE: 136
gatatcccgc tatgacattc tccctttttg gtgacaaatt tacccgccac atggctcaaa      60
tcttcaattt tag      73

<210> SEQ ID NO 137
<211> LENGTH: 73
<212> TYPE: DNA
<213> ORGANISM: Artificial Sequence
<220> FEATURE:
<223> OTHER INFORMATION: Synthetic construct

<400> SEQUENCE: 137
ttagtgactt tcagcccagg ctctttctat ctcttccgcc agaatcttca ttacttctga      60
ttcaggctgc ctg      73

<210> SEQ ID NO 138
<211> LENGTH: 21
<212> TYPE: DNA
<213> ORGANISM: Artificial Sequence
<220> FEATURE:
<223> OTHER INFORMATION: Synthetic construct

<400> SEQUENCE: 138
gttcggatat gaactggcag g      21

<210> SEQ ID NO 139
<211> LENGTH: 20
<212> TYPE: DNA
<213> ORGANISM: Artificial Sequence
<220> FEATURE:
<223> OTHER INFORMATION: Synthetic construct

<400> SEQUENCE: 139
caaacacgtt gcattggctg      20

<210> SEQ ID NO 140
<211> LENGTH: 75
<212> TYPE: DNA
<213> ORGANISM: Artificial Sequence
<220> FEATURE:
<223> OTHER INFORMATION: Synthetic construct

<400> SEQUENCE: 140
tctgccggta gcattgccgg accagaacta aaattgaaga tttgagccat ttatttgtta      60
actgttaatt gtcct      75

<210> SEQ ID NO 141
<211> LENGTH: 20
<212> TYPE: DNA
<213> ORGANISM: Artificial Sequence
<220> FEATURE:
<223> OTHER INFORMATION: Synthetic construct

<400> SEQUENCE: 141
cagagagttg ccattcacgc                                                      20

<210> SEQ ID NO 142
<211> LENGTH: 70
<212> TYPE: DNA
<213> ORGANISM: Artificial Sequence
<220> FEATURE:
<223> OTHER INFORMATION: Synthetic construct

<400> SEQUENCE: 142
gatatcccgc tatgacattc tccctttttg gtgacaaatt tacccgccac ttatctctgg          60
cggtgttgac                                                                 70

<210> SEQ ID NO 143
<211> LENGTH: 70
<212> TYPE: DNA
<213> ORGANISM: Artificial Sequence
<220> FEATURE:
<223> OTHER INFORMATION: Synthetic construct

<400> SEQUENCE: 143
tctgccggta gcattgccgg accagaacta aaattgaaga tttgagccat agctgtttcc          60
tggtttaaac                                                                 70

<210> SEQ ID NO 144
<211> LENGTH: 72
<212> TYPE: DNA
<213> ORGANISM: Artificial Sequence
<220> FEATURE:
<223> OTHER INFORMATION: Synthetic construct

<400> SEQUENCE: 144
tgttattagt tcgttactgg aagtccagtc accttgtcag gagtattatc tgtgacggaa          60
gatcacttcg ca                                                              72

<210> SEQ ID NO 145
<211> LENGTH: 75
<212> TYPE: DNA
<213> ORGANISM: Artificial Sequence
<220> FEATURE:
<223> OTHER INFORMATION: Synthetic construct

<400> SEQUENCE: 145
aaagcgggta taaattcgcc catccgttgc agatgggcga gtaagaagta ttatttgtta          60
actgttaatt gtcct                                                           75

<210> SEQ ID NO 146
<211> LENGTH: 70
<212> TYPE: DNA
<213> ORGANISM: Artificial Sequence
<220> FEATURE:
<223> OTHER INFORMATION: Synthetic construct

<400> SEQUENCE: 146
aagcgggtat aaattcgccc atccgttgca gatgggcgag taagaagtag ataatactcc          60
tgacaaggtg                                                                 70

<210> SEQ ID NO 147

-continued

```
<211> LENGTH: 20
<212> TYPE: DNA
<213> ORGANISM: Artificial Sequence
<220> FEATURE:
<223> OTHER INFORMATION: Synthetic construct

<400> SEQUENCE: 147
ccagtgaaga tgaagtctcg                                                            20

<210> SEQ ID NO 148
<211> LENGTH: 20
<212> TYPE: DNA
<213> ORGANISM: Artificial Sequence
<220> FEATURE:
<223> OTHER INFORMATION: Synthetic construct

<400> SEQUENCE: 148
atggatcgca cagtttggag                                                            20
```

MICROORGANISM FOR PRODUCING PANTOIC ACID, AND CONSTRUCTION METHOD THEREFOR AND APPLICATION THEREOF

CROSS-REFERENCE TO RELATED APPLICATION

This application claims priority to and is a 35 U.S.C. § 371 national phase application of PCT/CN2021/105954 (WO2022/198846), filed on Jul. 13, 2021, entitled "MICROORGANISM FOR PRODUCING PANTOIC ACID, AND CONSTRUCTION METHOD THEREFOR AND APPLICATION THEREOF", which application claims priority to and the benefit of China Patent Application No. 202110391896.0, filed Mar. 23, 2021, the disclosures of which are incorporated herein by reference in their entirety.

TECHNICAL FIELD

The present invention relates to the field of biotechnology, in particular, to a pantoic acid-producing microorganism and construction method and use of the same.

BACKGROUND OF THE INVENTION

Calcium pantothenate, also known as vitamin B5, is one of the 13 essential vitamins for the human body. Calcium pantothenate can only be synthesized in microorganisms and plants, and is an important precursor for synthesis of coenzyme A and an essential vitamin for maintaining normal physiological functions of organisms. Also, calcium pantothenate has a wide range of applications as a food additive, an active pharmaceutical ingredient and the like. Presently, calcium pantothenate is mainly obtained by reacting β-alanine with high-purity D-pantoyl lactone which is produced by biological or chemical resolution of DL-pantoyl lactone.

As an important precursor substance for the synthesis of calcium pantothenate, pantoyl lactone is currently synthesized mainly by chemical process using petrochemical materials. The materials used for the synthesis of DL-pantoyl lactone are mainly petrochemical materials such as isobutyraldehyde and formaldehyde, and said synthesis is accomplished through a series of chemical reactions such as hydroxymethylation, acidification or aldol condensation. This process involves a large amount of highly toxic raw materials such as sodium cyanide or chemical reagents such as strong bases and acids, and generates a large amount of waste water and waste gas, which causes serious and irreparable damage to the environment. It is further noteworthy that L-Pantoyl lactone needs to be removed thoroughly from DL-Pantoyl lactone for synthesis of calcium pantothenate so as to obtain high purity calcium D-pantothenate, which has extremely high requirements for a resolution process of DL-Pantoyl lactone. Due to the limitations of calcium pantothenate synthesis methods, in recent years, calcium pantothenate production companies are often subjected to environmental supervision and under pressure, and the price of calcium pantothenate varies from tens to hundreds of thousands CNY per ton.

With the rapid development of synthetic biology and metabolic engineering, the production of chemicals by fermentation from renewable raw materials through the design and construction of microbial cell factories has become an important alternative to the production of chemicals by chemical reactions from non-renewable resources such as petrochemicals, and has achieved a great success. Wild-type

*Escherichia coli* naturally have pathway for synthesis of pantoic acid. However, the wild-type *Escherichia coli* have difficulty in accumulating detectable concentrations of pantoic acid due to their own complex metabolic network regulation. Therefore, the design and construction of engineered strains capable of efficiently producing pantoic acid based on the genome-scale metabolic engineering will play a great role in solving the problems of heavy pollution and expensive raw materials during the production of calcium pantothenate. In addition, the pantoic acid obtained by microbial fermentation is itself high-purity D-pantoic acid without subsequent resolution, which will greatly lower the cost and reduce the environmental pollution from producing calcium pantothenate.

Therefore, the research and provision of genetically stable microbial cell factory that can produce high-purity pantoic acid by biological fermentation using glucose and the like as raw materials without adding inducers and antibiotics will be of great significance for promoting the production of calcium pantothenate, lowering the production costs, and reducing the environmental pollution.

SUMMARY OF THE INVENTION

The technical problem to be solved by the present invention is how to produce pantoic acid.

To solve the above technical problem, the present invention first provides a method of constructing a recombinant *Escherichia coli*, comprising modifying a starting *Escherichia coli* as following steps of A1-A25 to obtain a recombinant *Escherichia coli*:

A1. introducing and expressing an alsS gene encoding acetolactate synthase;

A2. replacing the promoter of ilvB gene encoding the large subunit of acetolactate synthase I with M1-93 promoter, wherein the M1-93 promoter is any selected from the group consisting of the following DNA molecules:

a1) a DNA molecule, wherein the nucleotide sequence of one strand of the DNA molecule is set forth as SEQ ID NO: 3;

a2) a DNA molecule having at least 80% identity with the DNA molecule in a1) and having a promoter function;

A3. replacing the promoter of ilvG gene encoding the large subunit of acetolactate synthase II with the M1-93 promoter;

A4. mutating the ilvH gene encoding a regulatory subunit of acetolactate synthase III to an ilvH mutant gene, wherein the ilvH mutant gene encodes the protein of SEQ ID NO: 5;

A5. introducing and expressing an ilvC gene encoding acetohydroxyl-acid reductoisomerase;

A6. introducing and expressing an ilvD gene encoding dihydroxy-acid dehydratase;

A7. introducing and expressing a panB gene encoding 3-methyl-2-oxobutanoate hydroxymethyltransferase derived from *Escherichia coli*, which is designated as E-panB gene;

A8. introducing and expressing a panE gene encoding 2-dehydropantothenate-2-reductase;

A9. introducing and expressing a glyA gene encoding glycine hydroxymethyltransferase;

A10. replacing the promoter of gcvT gene encoding aminomethyltransferase with the M1-93 promoter;

A11. replacing the promoter of gcvP gene encoding glycine decarboxylase with the M1-93 promoter;

A12. introducing and expressing a panB gene encoding 3-methyl-2-oxobutanoate hydroxymethyltransferase derived from *Corynebacterium glutamicum*, which is designated as C-panB gene;

A13. mutating the ilvE gene encoding branched-chain amino acid aminotransferase to an ilvE mutant gene, wherein the ilvE mutant gene encodes the protein of SEQ ID NO: 12;

A14. introducing and expressing a serA gene encoding phosphoglycerate dehydrogenase;

A15. introducing and expressing a serC gene encoding phosphoserine/phosphohydroxythreonine aminotransferase and a serB gene encoding phosphoserine phosphatase;

A16. knocking out the sdaA gene encoding L-serine deaminase I;

A17. knocking out the tdcD gene encoding propionate kinase and the tdcE gene encoding formate acetyltransferase;

A18. knocking out the adhE gene encoding alcohol dehydrogenase;

A19. knocking out the pflB gene encoding pyruvate formate lyase;

A20. knocking out the frd gene encoding fumarate reductase;

A21. knocking out the IdhA gene encoding lactate dehydrogenase;

A22. knocking out the mgsA gene encoding methylglyoxal synthase;

A23. knocking out the pta gene and the ackA gene encoding acetate kinase;

A24. knocking out the ara gene encoding ribokinase;

A25. knocking out the avtA gene encoding valine-pyruvate transaminase.

In the above method, the alsS gene may be derived from *Bacillus subtilis*, such as *Bacillus subtilis* 168.

The ilvC gene may be derived from *Escherichia coli*, such as *Escherichia coli* ATCC 8739.

The ilvD gene may be derived from *Escherichia coli*, such as *Escherichia coli* MG1655.

The panE gene may be derived from *Escherichia coli*, such as *Escherichia coli* MG1655.

The glyA gene may be derived from *Escherichia coli*, such as *Escherichia coli* ATCC 8739.

The serA gene may be derived from *Corynebacterium glutamicum*, such as *Corynebacterium glutamicum* ATCC13032.

The serC gene and the serB gene may be derived from *Escherichia coli*, such as *Escherichia coli* MG1655.

The E-panB gene may be derived from *Escherichia coli* MG1655.

The C-panB gene may be derived from *Corynebacterium glutamicum* ATCC13032.

In the above method, the alsS gene may encode the AlsS protein of SEQ ID NO: 2.

The C-panB gene may encode the C-panB protein of SEQ ID NO: 10.

The serA gene may encode the SerA protein of SEQ ID NO: 14.

The serC gene may encode the SerC protein of SEQ ID NO: 16.

The serB gene may encode the SerB protein of SEQ ID NO: 17.

In the above method, the sequence of the alsS gene may be set forth as SEQ ID NO: 1.

The sequence of the ilvH mutant gene may be set forth as SEQ ID NO: 4.

The sequence of the C-panB gene may be set forth as SEQ ID NO: 9.

The sequence of the ilvE mutant gene may be set forth as SEQ ID NO: 11.

The sequence of the serA gene may be set forth as SEQ ID NO: 13.

The sequence of the serC gene may be from positions 89 to 1177 of SEQ ID NO: 15.

The sequence of the serB gene may be from positions 1199 to 2167 of SEQ ID NO: 15.

In the above method, A1 may be achieved by introducing an alsS gene expression cassette into the recipient *Escherichia coli*, wherein the alsS gene expression cassette contains a promoter and the alsS gene driven by the promoter.

A5 may be achieved by introducing an ilvC gene expression cassette into the recipient *Escherichia coli*, wherein the ilvC gene expression cassette contains a promoter and the ilvC gene driven by the promoter.

A6 may be achieved by introducing an ilvD gene expression cassette into the recipient *Escherichia coli*, wherein the ilvD gene expression cassette contains a promoter and the ilvD gene driven by the promoter.

A7 may be achieved by introducing an E-panB gene expression cassette into the recipient *Escherichia coli*, wherein the E-panB gene expression cassette contains a promoter and the E-panB gene driven by the promoter.

A8 may be achieved by introducing a panE gene expression cassette into the recipient *Escherichia coli*, wherein the panE gene expression cassette contains a promoter and the panE gene driven by the promoter.

A9 may be achieved by introducing a glyA gene expression cassette into the recipient *Escherichia coli*, wherein the glyA gene expression cassette contains a promoter and the glyA gene driven by the promoter.

A12 may be achieved by introducing a C-panB gene expression cassette into the recipient *Escherichia coli*, wherein the C-panB gene expression cassette contains a promoter and the C-panB gene driven by the promoter.

A14 may be achieved by introducing a serA gene expression cassette into the recipient *Escherichia coli*, wherein the serA gene expression cassette contains a promoter and the serA gene driven by the promoter.

A15 may be achieved by introducing a serCB gene expression cassette into the recipient *Escherichia coli*, wherein the serCB gene expression cassette contains a promoter and the serC gene and the serB gene driven by the promoter.

In the above method, the promoter in A1, A7, A12, A14 or A15 may be the M1-93 promoter.

The promoter in A5 or A9 may be M1-46 promoter, wherein the M1-46 promoter is any selected from the group consisting of the following DNA molecules:

1) a DNA molecule, wherein the nucleotide sequence of one strand of the DNA molecule is set forth as SEQ ID NO: 6;

2) a DNA molecule having at least 80% identity with the DNA molecule in 1) and having a promoter function.

The promoter in A6 may be RBSL1 promoter, wherein the RBSL1 promoter is any selected from the group consisting of the following DNA molecules:

a1) a DNA molecule, wherein the nucleotide sequence of one strand of the DNA molecule is set forth as SEQ ID NO: 7;

a2) a DNA molecule having at least 80% identity with the DNA molecule in a1) and having a promoter function.

The promoter in A8 may be RBSL2 promoter, wherein the RBSL2 promoter is any selected from the group consisting of the following DNA molecules:

c1) a DNA molecule, wherein the nucleotide sequence of one strand of the DNA molecule is set forth as SEQ ID NO: 8;

c2) a DNA molecule having at least 80% identity with the DNA molecule in c1) and having a promoter function.

The term "identity" used herein means sequence similarity to the natural nucleic acid sequences. The "identity" includes nucleotide sequences having 80% or higher, or 85% or higher, or 90% or higher, or 95% or higher identity with the nucleotide sequences of the present invention. The identity can be evaluated manually or by computer software. Using a computer software, the identity between two or more sequences can be expressed as a percentage (%), which can be used to evaluate the identity between related sequences.

The above-mentioned "at least 80% identity" may be more than 85%, 90% or 95% identity.

Said serCB gene expression cassette may be set forth in SEQ ID NO: 15.

In the above method, said starting *Escherichia coli* may be *Escherichia coli* ATCC 8739.

The recombinant *Escherichia coli* obtained using said method of constructing a recombinant *Escherichia coli* also falls within the protection scope of the present invention.

In one embodiment of the present invention, using *Escherichia coli* ATCC 8739 as the starting *Escherichia coli*, the recombinant *Escherichia coli* Span050 is obtained using said method of constructing a recombinant *Escherichia coli*, and the *Escherichia coli* Span050 was deposited in the China General Microbiological Culture Collection Center (CGMCC), with accession number of CGMCC No. 21699.

The present invention also provides a method of producing pantoic acid, comprising: culturing said recombinant *Escherichia coli* to obtain fermentation products; and obtaining pantoic acid from said fermentation products.

The culturing of said recombinant *Escherichia coli* may be carried out using a glucose-containing medium that can be used for culturing of *Escherichia coli*.

Said medium may be medium 1, medium 2 or medium 3. Said medium 1 consists of a solvent and solutes, wherein the solvent is water, and the solutes and the concentrations of said solutes in said medium 1 respectively are: glucose 20 g/L, $(NH_4)_2HPO_4$ 3.5 g/L, $KH_2PO_4$ 3.91 g/L, $K_2HPO_4$ 4.48 g/L, $MgSO_4 \cdot 7H_2O$ 0.18 g/L, betaine-HCl 0.15 g/L, $FeCl_3 \cdot 6H_2O$ 1.5 µg/L, $CoCl_2 \cdot 6H_2O$ 0.1 Kg/L, $CuCl_2 \cdot 2H_2O$ 1.1 g/L, $ZnCl_2$ 0.1 µg/L, $Na_2MoO_4 \cdot 2H_2O$ 0.1 µg/L, $MnCl_2 \cdot 4H_2O$ 0.2 µg/L and $H_3BO_3$ 0.05 µg/L.

Said medium 2 consists of a solvent and solutes, wherein the solvent is water, and the solutes and concentration of said solutes in said medium 2 respectively are: glucose 50 g/L, $(NH_4)_2HPO_4$ 3.5 g/L, $KH_2PO_4$ 3.91 g/L, $K_2HPO_4$ 4.48 g/L, $MgSO_4 \cdot 7H_2O$ 0.18 g/L, betaine-HCl 0.15 g/L, 5 g/L serine, $FeCl_3 \cdot 6H_2O$ 1.5 µg/L, $CoCl_2 \cdot 6H_2O$ 0.1 µg/L, $CuCl_2 \cdot 2H_2O$ 0.1 µg/L, $ZnCl_2$ 0.1 µg/L, $Na_2MoO_4 \cdot 2H_2O$ 0.1 µg/L, $MnCl_2 \cdot 4H_2O$ 0.2 µg/L and $H_3BO_3$ 0.05 µg/L.

Said medium 3 consists of a solvent and solutes, wherein the solvent is water, and the solutes and concentration of said solutes in said medium 3 respectively are: glucose 30 g/L, magnesium sulfate 5 g/L, potassium dihydrogen phosphate 10.5 g/L, yeast powder 20 g/L, diammonium hydrogen phosphate 6 g/L, citric acid monohydrate 1.84 g/L, $FeCl_3 \cdot 6H_2O$ 1.5 µg/L. $CoCl_2 \cdot 6H_2O$ 0.1 µg/L, $CuCl_2 \cdot 2H_2O$ 0.1 µg/L, $ZnCl_2$ 0.1 µg/L, $Na_2MoO_4 \cdot 2H_2O$ 0.1 µg/L, $MnCl_2 \cdot 4H_2O$ 0.2 µg/L and $H_3BO_3$ 0.05 µg/L.

During culturing, glucose may be added to the culture system according to the culture conditions.

Said culturing may be carried out at 37° C.

The present invention further provides use of:

X1. the method of constructing a recombinant *Escherichia coli* in production of pantoic acid;

X2. the method of constructing a recombinant *Escherichia coli* in production of calcium pantothenate;

X3. the recombinant *Escherichia coli* in production of pantoic acid;

X4. the recombinant *Escherichia coli* in preparation and production of pantoic acid products;

X5. the recombinant *Escherichia coli* in production of calcium pantothenate;

X6. the recombinant *Escherichia coli* in preparation and production of calcium pantothenate products; or X7. the method of producing pantoic acid in production of calcium pantothenate.

Description of Biological Material Deposit

Taxonomic designation: *Escherichia coli*

Strain ID: Span050

Name of depository institute: China General Microbiological Culture Collection Center Abbreviation of depository institute: CGMCC Address: No. 3, No. 1 West Beichen Road, Chaoyang District, Beijing, 100101, P.R. China Date of deposit: Jan. 22, 2021

Accession number: CGMCC No. 21699

BEST MODE TO CARRY OUT THE INVENTION

The present invention will be further described in detail below in combination with specific embodiments. The given examples are only intended to illustrate the present invention, rather than to limit the scope of the present invention. The examples provided below may serve as a guide for further improvements by those of ordinary skill in the art and do not constitute a restriction to the present invention in any way.

The experimental methods in the following examples, unless otherwise specified, are conventional and performed in accordance with the techniques or conditions described in the literature in the art or in accordance with the product specification. The materials, reagents, instruments, etc. used in the following examples, unless otherwise specified, are commercially available. For the quantitative tests in the following examples, three replicate experiments are set up and the results are averaged. In the following examples, unless otherwise specified, the first position of each nucleotide sequence in the sequence list is the 5' terminal nucleotide of the corresponding DNA/RNA, and the last position is the 3' terminal nucleotide of the corresponding DNA/RNA.

TABLE 1

Strains and plasmids used in the present invention

| Strain | Associated characteristics | Source |
|---|---|---|
| ATCC 8739 | Wild-type strain | Wild-type |
| M1-93 | ATCC 8739, FRT-Km-FRT::M1-93::lacZ | Lu, et al., Appl Microbiol Biotechnol, 2012, 93: 2455-2462 |
| M1-46 | ATCC 8739, FRT-Km-FRT::M1-46::lacZ | Lu, et al., Appl Microbiol Biotechnol, 2012, 93: 2455-2462 |
| Span001 | ATCC 8739, tdcDE::cat-sacB | Constructed by the present invention |
| Span002 | Span001, tdcDE::alsS | Constructed by the present invention |
| Span003 | Span002, tdcDE::cat-sacB::alsS | Constructed by the present invention |
| Span004 | Span002, tdcDE::M1-93::alsS | Constructed by the present invention |
| Span005 | Span004, cat-sacB::ilvB | Constructed by the present invention |
| Span006 | Span004, M1-93::ilvB | Constructed by the present invention |
| Span007 | Span006, cat-sacB::ilvG | Constructed by the present invention |
| Span008 | Span006, M1-93::ilvG | Constructed by the present invention |
| Span009 | Span008, ilvH::cat-sacB | Constructed by the present invention |
| Span010 | Span008, ilvH::ilvH* | Constructed by the present invention |
| Span011 | Span010, adhE::cat-sacB | Constructed by the present invention |
| Span012 | Span010, adhE::ilvC | Constructed by the present invention |
| Span013 | Span012, adhE::cat-sacB::ilvC | Constructed by the present invention |
| Span014 | Span012, adhE::M1-46::ilvC | Constructed by the present invention |
| Span015 | Span014, pflB::cat-sacB | Constructed by the present invention |
| Span016 | Span014, pflB::ilvD | Constructed by the present invention |
| Span017 | Span016, pflB::cat-sacB::ilvD | Constructed by the present invention |
| Span018 | Span016, pflB::RBSL1::ilvD | Constructed by the present invention |
| Span019 | Span018, frd::cat-sacB | Constructed by the present invention |
| Span020 | Span018, frd::panB | Constructed by the present invention |
| Span021 | Span020, frd::cat-sacB::panB | Constructed by the present invention |
| Span022 | Span020, frd::M1-93::panB | Constructed by the present invention |
| Span023 | Span022, ldhA::cat-sacB | Constructed by the present invention |
| Span024 | Span022, ldhA::panE | Constructed by the present invention |
| Span025 | Span024, ldhA::cat-sacB::panE | Constructed by the present invention |
| Span026 | Span024, ldhA::RBSL2::panE | Constructed by the present invention |
| Span027 | Span026, mgsA::cat-sacB | Constructed by the present invention |
| Span028 | Span026, mgsA::glyA | Constructed by the present invention |
| Span029 | Span028, mgsA::cat-sacB::glyA | Constructed by the present invention |
| Span030 | Span028, mgsA::M1-46::glyA | Constructed by the present invention |
| Span031 | Span030, gcvTH::cat-sacB | Constructed by the present invention |
| Span032 | Span030, M1-93::gcvTH | Constructed by the present invention |
| Span033 | Span032, gcvP::cat-sacB | Constructed by the present invention |
| Span034 | Span032, M1-93::gcvP | Constructed by the present invention |
| Span035 | Span034, ackA-pta::cat-sacB | Constructed by the present invention |
| Span036 | Span034, ackA-pta::panB-C.glu | Constructed by the present invention |
| Span037 | Span036, ackA-pta::cat-sacB::panB-C.glu | Constructed by the present invention |
| Span038 | Span036, ackA-pta::M1-93::panB-C.glu | Constructed by the present invention |
| Span039 | Span038, ilvE::cat-sacB | Constructed by the present invention |
| Span040 | Span038, ilvE::ilvE*-GTG | Constructed by the present invention |
| Span041 | Span040, ara::cat-sacB | Constructed by the present invention |
| Span042 | Span040, ara::serA197 | Constructed by the present invention |
| Span043 | Span042, ara::cat-sacB::serA197 | Constructed by the present invention |
| Span044 | Span042, ara::M1-93-serA197 | Constructed by the present invention |
| Span045 | Span044, avtA::cat-sacB | Constructed by the present invention |
| Span046 | Span044, avtA::serCB | Constructed by the present invention |
| Span047 | Span046, avtA::cat-sacB::serCB | Constructed by the present invention |
| Span048 | Span046, avtA::M1-93::serCB | Constructed by the present invention |
| Span049 | Span048, sdaA::cat-sacB | Constructed by the present invention |
| Span050 | Span048, ΔsdaA | Constructed by the present invention |

In Table 1, ATCC 8739, M1-93 and M1-46 are all *Escherichia coli*.

TABLE 2

Primers used in the present invention

| Name of primer | Sequence |
|---|---|
| tdcDE-incs-up | CcgtgattggtctgctgaccatcctgaacatcgtatacaaactgtttttaaTGTGACGGAAGATCACTTC GCAG (SEQ ID NO: 18) |
| tdcDE-incs-down | ataatgttctttgctacaggaaaatcaacaatatgcgcaccagatgccacTTATTTGTTAACTGTTAAT TGTCCT (SEQ ID NO: 19) |
| tdcDE-alsSin-up | ccgtgattggtctgctgaccatcctgaacatcgtatacaaactgtttttaaATGTTGACAAAAGCAACAA AAG (SEQ ID NO: 20) |

TABLE 2-continued

Primers used in the present invention

| Name of primer | Sequence |
| --- | --- |
| tdcDE-alsSin-down | ataatgttctttgctacaggaaaatcaacaatatgcgcaccagatgccacGCATGAGCTCCTAGAGAGC TTTCGTTTTCATG (SEQ ID NO: 21) |
| XZ-tdcDE-up | TGATGAGCTACCTGGTATGGC (SEQ ID NO: 22) |
| XZ-tdcDE-down | CGCCGACAGAGTAATAGGTTTTAC (SEQ ID NO: 23) |
| alsSPro-CS-down | CCTCTGTTTTTCACAAGGGATTTTTGTTCTTTTGTTGCTTTTGTCAACATTTATTTGTTAACTGTTAAT TGTCCT (SEQ ID NO: 24) |
| alsS-Pro-up | ccgtgattggtctgctgaccatcctgaacatcgtatacaaactgttttaaTTATCTCTGGCGGTGTTGA C (SEQ ID NO: 25) |
| alsS-Pro-down | CCTCTGTTTTTCACAAGGGATTTTTGTTCTTTTGTTGCTTTTGTCAACATAGCTGTTTCCTGGTTTAAA C (SEQ ID NO: 26) |
| tdcDE-YZ285-down | GCCTGTTGCCAAGTTAGAGG (SEQ ID NO: 27) |
| ilvB pro-catup | ctgacgaaacctcgctccggcggggtttttttgttatctgcaattcagtacTGTGACGGAAGATCACTTC GCA (SEQ ID NO: 28) |
| ilvB pro-catdown | tctgcgccggtaaagcgcttacgcgtcgatgttgtgcccgaacttgccatTTATTTGTTAACTGTTAAT TGTCCT (SEQ ID NO: 29) |
| ilvB pro-up | ctgacgaaacctcgctccggcggggtttttttgttatctgcaattcagtacTTATCTCTGGCGGTGTTGA C (SEQ ID NO: 30) |
| ilvB pro-down | tctgcgccggtaaagcgcttacgcgtcgatgttgtgcccgaacttgccatAGCTGTTTCCTGGTTTAAA C (SEQ ID NO: 31) |
| ilvB pro-YZup | gttctgcgcggaacacgtatac (SEQ ID NO: 32) |
| ilvB pro-YZdown | ccgctacaggccatacagac (SEQ ID NO: 33) |
| ilvG pro-catup | tgaactaagaggaagggaacaacattcagaccgaaattgaattttttttcaTGTGACGGAAGATCACTTC GCA (SEQ ID NO: 34) |
| ilvG pro-catdown | ttcacaccctgtgcccgcaacgcatgtaccacccactgtgcgccattcatTTATTTGTTAACTGTTAAT TGTCCT (SEQ ID NO: 35) |
| ilvG pro-up | tgaactaagaggaagggaacaacattcagaccgaaattgaattttttttcaTTATCTCTGGCGGTGTTGA C (SEQ ID NO: 36) |
| ilvG pro-down | ttcacaccctgtgcccgcaacgcatgtaccacccactgtgcgccattcatAGCTGTTTCCTGGTTTAAA CG (SEQ ID NO: 37) |
| ilvG pro-YZup | gcataagatatcgctgctgtag (SEQ ID NO: 38) |
| ilvG p-YZdown | gccagttttgccagtagcac (SEQ ID NO: 39) |
| ilvH*-cat-up | agaacctgattatgCGCCGGATATTATCAGTCTTACTCGAAAATGAATCATGTGACGGAAGATCACTTC GCA (SEQ ID NO: 40) |
| ilvH*-cat-down | TTCATCGCCCACGGTCTGGATGGTCATACGCGATAATGTCGGATCGTCGGTTATTTGTTAACTGTTAAT TGTCCT (SEQ ID NO: 41) |
| ilvH*-mut-up | agaacctgattatgCGCCGGATATTATCAGTCTTACTCGAAAATGAATCAGaCGCGTTATtCCGCGTGA TTGGC (SEQ ID NO: 42) |
| ilvH*-mut-down | CACACCAGAGCGAGCAACCTC (SEQ ID NO: 43) |
| ilvH*-mutYZ-up | atgagctggaaagcaaacttagc (SEQ ID NO: 44) |
| adhE-cs-up | ATAACTCTAATGTTTAAACTCTTTTAGTAAATCACAGTGAGTGTGAGCGCTGTGACGGAAGATCACTTC GCA (SEQ ID NO: 45) |
| adhE-cs-down | CCGTTTATGTTGCCAGACAGCGCTACTGATTAAGCGGATTTTTTCGCTTTTTATTTGTTAACTGTTAAT TGTCCT (SEQ ID NO: 46) |
| adhE-ilvC-up | ATAACTCTAATGTTTAAACTCTTTTAGTAAATCACAGTGAGTGTGAGCGCATGGCTAACTACTTCAATA C (SEQ ID NO: 47) |
| adhE-ilvC-down | CCGTTTATGTTGCCAGACAGCGCTACTGATTAAGCGGATTTTTTCGCTTTTTAACCCGCAACAGCAATA CG (SEQ ID NO: 48) |

TABLE 2-continued

Primers used in the present invention

| Name of primer | Sequence |
|---|---|
| XZ-adhE-up | CATGCTAATGTAGCCACCAAA (SEQ ID NO: 49) |
| XZ-adhE-down | TTGCACCACCATCCAGATAA (SEQ ID NO: 50) |
| ilvC-ProCS-down | agctgtgccagctgctggcgcagattcagtGTATTGAAGTAGTTAGCCATTTATTTGTTAACTGTTAAT<br>TGTCCT (SEQ ID NO: 51) |
| ilvC-Pro-up | ATAACTCTAATGTTTAAACTCTTTTAGTAAATCACAGTGAGTGTGAGCGCTTATCTCTGGCGGTGTTGA<br>C (SEQ ID NO: 52) |
| ilvC-Pro-down | agctgtgccagctgctggcgcagattcagtGTATTGAAGTAGTTAGCCATAGCTGTTTCCTGGTTTAAA<br>CCG (SEQ ID NO: 53) |
| ilvC-YZ347-down | cgcactacatcagagtgctg (SEQ ID NO: 54) |
| pflB-CS-up | aaacgaccaccattaatggttgtcgaagtacgcagtaaataaaaaatccaTGTGACGGAAGATCACTTC<br>GCAG (SEQ ID NO: 55) |
| pflB-CS-down | CGGTCCGAACGGCGCGCCAGCACGACGACCGTCTGGGGTGTTACCCGTTTTTATTTGTTAACTGTTAAT<br>TGTCCT (SEQ ID NO: 56) |
| pflB-ilvD-up | aaacgaccaccattaatggttgtcgaagtacgcagtaaataaaaaatccaatgcctaagtaccgttccg<br>c (SEQ ID NO: 57) |
| pflB-ilvD-down | CGGTCCGAACGGCGCGCCAGCACGACGACCGTCTGGGGTGTTACCCGTTTttaacccccccagtttcgat<br>ttatc (SEQ ID NO: 58) |
| XZ-pflB-up600 | CTGCGGAGCCGATCTCTTTAC (SEQ ID NO: 59) |
| XZ-pflB-down | CGAGTAATAACGTCCTGCTGCT (SEQ ID NO: 60) |
| pflB-Pcs-down | CCCGCCATATTACGACCATGAGTGGTGGTGGCGGAACGGTACTTAGGCATTTATTTGTTAACTGTTAAT<br>TGTCCT (SEQ ID NO: 61) |
| pflB-Pro-up | AAACGACCACCATTAATGGTTGTCGAAGTACGCAGTAAATAAAAAATCCATTATCTCTGGCGGTGTTGA<br>C (SEQ ID NO: 62) |
| ilvD-Pro-down | cccgccatattacgaccatgagtggtggtggcggaacggtacttaggcatTGCTGACCTCCTGGTTTAA<br>ACGTACATG (SEQ ID NO: 63) |
| ilvD-YZ496-down | caaccagatcgagcttgatg (SEQ ID NO: 64) |
| XZ-frd-up | TGCAGAAAACCATCGACAAG (SEQ ID NO: 65) |
| XZ-frd-down | CACCAATCAGCGTGACAACT (SEQ ID NO: 66) |
| frd-cs-up | GAAGGCGAATGGCTGAGATGAAAAACCTGAAAATTGAGGTGGTGCGCTATTGTGACGGAAGATCACTTC<br>GCA (SEQ ID NO: 67) |
| frd-cs-down | TCTCAGGCTCCTTACCAGTACAGGGCAACAAACAGGATTACGATGGTGGCTTATTTGTTAACTGTTAAT<br>TGTCCT (SEQ ID NO: 68) |
| Frd-panB-up | GAAGGCGAATGGCTGAGATGAAAAACCTGAAAATTGAGGTGGTGCGCTATatgAAACCGACCACCATCT<br>C (SEQ ID NO: 69) |
| Frd-panB-down | TCTCAGGCTCCTTACCAGTACAGGGCAACAAACAGGATTACGATGGTGGCttaATGGAAACTGTGTTCT<br>TCGC (SEQ ID NO: 70) |
| panB-Pcs-down | TTTTTTTCCTGTTTGTACTTCTGCAGTAAGGAGATGGTGGTCGGTTTcatTTATTTGTTAACTGTTAAT<br>TGTCCT (SEQ ID NO: 71) |
| panB-Pro-up | GAAGGCGAATGGCTGAGATGAAAAACCTGAAAATTGAGGTGGTGCGCTATTTATCTCTGGCGGTGTTGA<br>C (SEQ ID NO: 72) |
| panB-Pro-down | TTTTTTTCCTGTTTGTACTTCTGCAGTAAGGAGATGGTGGTCGGTTTcatAGCTGTTTCCTGGTTTAAA<br>C (SEQ ID NO: 73) |
| panB-YZ130-down | CCACCAGCATGACGTTAAGC (SEQ ID NO: 74) |
| ldhA-csin-up | attatatttgaaattttgtaaaatattttttagtagcttaaatgtgattcaTGTGACGGAAGATCACTTC<br>GCAG (SEQ ID NO: 75) |
| ldhA-csin-down | AACCAGTTCGTTCGGGCAGGTTTCGCCTTTTTCCAGAGCATGAGCTCCTaTTATTTGTTAACTGTTAAT<br>TGTCCT (SEQ ID NO: 76) |

TABLE 2-continued

Primers used in the present invention

| Name of primer | Sequence |
| --- | --- |
| ldhA-panE-up | attatatttgaaatttttgtaaaatattttttagtagcttaaatgtgattcaatgAAAATTACCGTATTGG<br>G (SEQ ID NO: 77) |
| ldhA-panE-down | AACCAGTTCGTTCGGGCAGGTTTCGCCTTTTTCCAGAGCATGAGCTCCTactaCCAGGGGCGAGGCAAA<br>C (SEQ ID NO: 78) |
| XZ-ldhA-up | GATAACGGAGATCGGGAATG (SEQ ID NO: 79) |
| XZ-ldhA-down | CTTTGGCTGTCAGTTCACCA (SEQ ID NO: 80) |
| panE-ProCS-down | GTAAGCCATAATTGCCCTAAGGCACCGCATCCCAATACGGTAATTTTcatTTATTTGTTAACTGTTAAT<br>TGTCCT (SEQ ID NO: 81) |
| panE-Pro-up | attatatttgaaatttttgtaaaatattttttagtagcttaaatgtgattcaTTATCTCTGGCGGTGTTGA<br>C (SEQ ID NO: 82) |
| panE-Pro-down | GTAAGCCATAATTGCCCTAAGGCACCGCATCCCAATACGGTAATTTTcatTCGAACCCTCCTGGTTTAA<br>AC (SEQ ID NO: 83) |
| panE-YZ245-down | CTTTTGACGGCATCGGAAAC (SEQ ID NO: 84) |
| mgsA-cs-up | gtaggaaagttaactacggatgtacattatggaactgacgactcgcacttTGTGACGGAAGATCACTTC<br>GCAG (SEQ ID NO: 85) |
| mgsA-cs-down | gcgtttgccacctgtgcaatattacttcagacggtccgcgagataacgctTTATTTGTTAACTGTTAAT<br>TGTCCT (SEQ ID NO: 86) |
| XZ-mgsA-up | cagctcatcaaccaggtcaa (SEQ ID NO: 87) |
| XZ-mgsA-down | aaaagccgtcacgttattgg (SEQ ID NO: 88) |
| mgsA-glyA-up | gtaggaaagttaactacggatgtacattatggaactgacgactcgcacttatgTTAAAGCGTGAAATGA<br>AC (SEQ ID NO: 89) |
| mgsA-glyA-down | gcgtttgccacctgtgcaatattacttcagacggtccgcgagataacgcttttaTGCGTAAACCGGGTAA<br>C (SEQ ID NO: 90) |
| glyA-ProCS-down | TGCCACAGTTCGGCATCATAATCGGCAATGTTCATTTCACGCTTTAAcatTTATTTGTTAACTGTTAAT<br>TGTCCT (SEQ ID NO: 91) |
| glyA-Pro-up | gtaggaaagttaactacggatgtacattatggaactgacgactcgcacttTTATCTCTGGCGGTGTTGA<br>C (SEQ ID NO: 92) |
| glyA-Pro-down | TGCCACAGTTCGGCATCATAATCGGCAATGTTCATTTCACGCTTTAAcatAGCTGTTTCCTGGTTTAAA<br>C (SEQ ID NO: 93) |
| glyA-YZ364-down | CCAGGTTCATACCCAGAACG (SEQ ID NO: 94) |
| gcvT-Pcat-up | ttgatttagtgttttttgacatttttttagctcttaatattgtcttattcTGTGACGGAAGATCACTTC<br>GCA (SEQ ID NO: 95) |
| gcvT-PsacB-down | cgagcgccgcaaagcgtgtgttgttcgtacaaaggagtctgttgtgccatTTATTTGTTAACTGTTAAT<br>TGTCCT (SEQ ID NO: 96) |
| gcvT-M93-up | ttgatttagtgttttttgacatttttttagctcttaatattgtcttattcTTATCTCTGGCGGTGTTGA<br>C (SEQ ID NO: 97) |
| gcvT-M93-down | cgagcgccgcaaagcgtgtgttgttcgtacaaaggagtctgttgtgccatAGCTGTTTCCTGGTTTAAA<br>CG (SEQ ID NO: 98) |
| gcvT-up-500 | ccaggcaatgggattaaacg (SEQ ID NO: 99) |
| gcvT-350-down | gtggcggagttaacaacgag (SEQ ID NO: 100) |
| gcvP-Pcat-up | aatcactgctggatgcgaccgcatacgaagcattgttagaagacgagtaaTGTGACGGAAGATCACTTC<br>GCA (SEQ ID NO: 101) |
| gcvP-PsacB-down | cgttcaataaaagcgccgctgttttcaagctggcttaacgtctgtgtcatTTATTTGTTAACTGTTAAT<br>TGTCCT (SEQ ID NO: 102) |
| gcvP-M93-up | aatcactgctggatgcgaccgcatacgaagcattgttagaagacgagtaaTTATCTCTGGCGGTGTTGA<br>C (SEQ ID NO: 103) |
| gcvP-M93-down | cgttcaataaaagcgccgctgttttcaagctggcttaacgtctgtgtcatAGCTGTTTCCTGGTTTAAA<br>CG (SEQ ID NO: 104) |

TABLE 2-continued

Primers used in the present invention

| Name of primer | Sequence |
|---|---|
| gcvH-up | atgagcaacgtaccagcagaac (SEQ ID NO: 105) |
| gcvP-390-down | gaagttgagcagtgcttcaag (SEQ ID NO: 106) |
| ackA-cs-up | aggtacttccatgtcgagtaagttagtactggttctgaactgcggtagttTGTGACGGAAGATCACTTCGCAG (SEQ ID NO: 107) |
| pta-cs-down | ggtcggcagaacgctgtaccgctttgtaggtggtgttaccggtgttcagaTTATTTGTTAACTGTTAATTGTCCT (SEQ ID NO: 108) |
| ackA-panBC-up | AGGTACTTCCATGTCGAGTAAGTTAGTACTGGTTCTGAACTGCGGTAGTTatgcccatgtcaggcattgatg (SEQ ID NO: 109) |
| ackA-panBC-down | GGTCGGCAGAACGCTGTACCGCTTTGTAGGTGGTGTTACCGGTGTTCAGAttaaaaggactccgcttcgc (SEQ ID NO: 110) |
| XZ-ackA-up | cgggacaacgttcaaaacat (SEQ ID NO: 111) |
| XZ-pta-down | attgcccatcttcttgttgg (SEQ ID NO: 112) |
| panBC-Pro-up | AGGTACTTCCATGTCGAGTAAGTTAGTACTGGTTCTGAACTGCGGTAGTTTTATCTCTGGCGGTGTTGAC (SEQ ID NO: 113) |
| panBC-Pro-down | cggaaatgacgggtgcggattttctttgcatcaatgcctgacatgggcatAGCTGTTTCCTGGTTTAAAC (SEQ ID NO: 114) |
| panBC-ProCS-down | cggaaatgacgggtgcggattttctttgcatcaatgcctgacatgggcatTTATTTGTTAACTGTTAATTGTCCT (SEQ ID NO: 115) |
| panBC-YZ425-down | accggaattccagcatcaac (SEQ ID NO: 116) |
| ilvE-cat-up | cacaaccacatcacaacaaatccgcgcctgagcgcaaaaggaatataaaaTGTGACGGAAGATCACTTCGCA (SEQ ID NO: 117) |
| ilvE-sacB-down | cgaaccatctccccattgaaccaaatgtaatcagctttcttcgtggtcatTTATTTGTTAACTGTTAATTGTCCT (SEQ ID NO: 118) |
| ilvEGTG-up | cacaaccacatcacaacaaatccgcgcctgagcgcaaaaggaatataaaaGtgaccacgaagaaagctgattac (SEQ ID NO: 119) |
| ilvE-down | ttattgattaacttgatctaaccagcc (SEQ ID NO: 120) |
| ilvM-up | atgatgcaacatcaggtcaatg (SEQ ID NO: 121) |
| araBCD-CS-up | GCCGAAAACCCGAACGCGATGTTCGTATTGTGGAAAGACCACACTGCGGTTGTGACGGAAGATCACTTCGCA (SEQ ID NO: 122) |
| araBCD-CS-down | TCACGCATGTTATCGCCAAAACGGCAGACTTTCAGATGACGGGTATCCTGTTATTTGTTAACTGTTAATTGTCCT (SEQ ID NO: 123) |
| araBCD-serA197-up | GCCGAAAACCCGAACGCGATGTTCGTATTGTGGAAAGACCACACTGCGGTATGAGCCAGAATGGCCGTCC (SEQ ID NO: 124) |
| araBCD-serA197-down | TCACGCATGTTATCGCCAAAACGGCAGACTTTCAGATGACGGGTATCCTGTTAAGCCAGATCCATCCACAC (SEQ ID NO: 125) |
| araBCD-YZ300-up | CACCAGCGTAGAGTGGTATC (SEQ ID NO: 126) |
| araBCD-YZ468-down | CTGCAGACCGGTTGACATCAC (SEQ ID NO: 127) |
| serA197-ProCS-down | TGCGCAAGCTTATCGGCGATGAGGACTACCGGACGGCCATTCTGGCTCATTTATTTGTTAACTGTTAATTGTCCT (SEQ ID NO: 128) |
| serA197-Pro-up | GCCGAAAACCCGAACGCGATGTTCGTATTGTGGAAAGACCACACTGCGGTTTATCTCTGGCGGTGTTGAC (SEQ ID NO: 129) |
| serA197-Pro-down | TGCGCAAGCTTATCGGCGATGAGGACTACCGGACGGCCATTCTGGCTCATAGCTGTTTCCTGGTTTAAAC (SEQ ID NO: 130) |
| SerA197-YZ358-down | TCTGGCGAGCAGTAGACAGC (SEQ ID NO: 131) |
| avtA-CS-up | atgacattctccctttttggtgacaaatttacccgccactccggcattacTGTGACGGAAGATCACTTCGCA (SEQ ID NO: 132) |

TABLE 2-continued

Primers used in the present invention

| Name of primer | Sequence |
|---|---|
| avtA-CS-down | ttagtgactttcagcccaggctctttctatctcttccgccagaatcttcaTTATTTGTTAACTGTTAAT TGTCCT (SEQ ID NO: 133) |
| serC-down | GCACCAGGTAATGTTAGGCATGTTTGTTCTCCTTTTGTCGACTTAACCGTGACGGCGTTCGAAC (SEQ ID NO: 134) |
| serB-up | GTTCGAACGCCGTCACGGTTAAGTCGACAAAAGGAGAACAAACATGCCTAACATTACCTGGTGC (SEQ ID NO: 135) |
| avtA-serCB-up | gatatcccgctatgacattctcccttttggtgacaaatttacccgccacATGGCTCAAATCTTCAATT TTAG (SEQ ID NO: 136) |
| avtA-serCB-down | ttagtgactttcagcccaggctctttctatctcttccgccagaatcttcaTTACTTCTGATTCAGGCTG CCTG (SEQ ID NO: 137) |
| avtA-YZ-up | gttcggatatgaactggcagg (SEQ ID NO: 138) |
| avtA-YZ-down | caaacacgttgcattggctg (SEQ ID NO: 139) |
| serCB-ProCS-down | TCTGCCGGTAGCATTGCCGGACCAGAACTAAAATTGAAGATTTGAGCCATTTATTTGTTAACTGTTAAT TGTCCT (SEQ ID NO: 140) |
| serCB-YZ317-down | CAGAGAGTTGCCATTCACGC (SEQ ID NO: 141) |
| serCB-Pro-up | gatatcccgctatgacattctcccttttggtgacaaatttacccgccacTTATCTCTGGCGGTGTTGA C (SEQ ID NO: 142) |
| serCB-Pro-down | TCTGCCGGTAGCATTGCCGGACCAGAACTAAAATTGAAGATTTGAGCCATAGCTGTTTCCTGGTTTAAA C (SEQ ID NO: 143) |
| sdaA-delcat-up | tgttattagttcgttactggaagtccagtcaccttgtcaggagtattatcTGTGACGGAAGATCACTTC GCA (SEQ ID NO: 144) |
| sdaA-delsacB-down | aaagcgggtataaattcgcccatccgttgcagatgggcgagtaagaagtaTTATTTGTTAACTGTTAAT TGTCCT (SEQ ID NO: 145) |
| SdaAdel-down | aagcgggtataaattcgcccatccgttgcagatgggcgagtaagaagtagataatactcctgacaaggt g (SEQ ID NO: 146) |
| sdaA-YZ-up | ccagtgaagatgaagtctcg (SEQ ID NO: 147) |
| sdaA-YZ-down | atggatcgcacagtttggag (SEQ ID NO: 148) |

Hereinafter two primers separated by "/" are used to form the corresponding primer pairs for amplification of the target fragments.

Example 1. Insertion of an AlsS Gene Encoding Acetolactate Synthase into the Loci of the tdcD Gene Encoding Propionate Kinase and the tdcE Gene Encoding Formate Acetyltransferase in ATCC 8739 Strain and Knockout of the tdcDE Operon Starting from *Escherichia coli* ATCC 8739, an alsS gene encoding acetolactate synthase from *Bacillus subtilis* 168 (from ATCC, No. 23857) was inserted into the loci of the tdcD gene encoding propionate kinase and the tdcE gene encoding formate acetyltransferase on chromosome using a two-step homologous recombination method, which comprises specific steps as follows:

in step one, using pXZ-CS (Tan, et al., *Appl Environ Microbiol,* 2013, 79:4838-4844) plasmid DNA as a template, a DNA fragment I of 2719 bp was amplified with the primers tdcDE-incs-up/tdcDE-incs-down, wherein the fragment contains 50 bp of the upstream homology arm of tdcDE gene, 2619 bp of the cat-sacB fragment of chloramphenicol gene (cat) and levansucrase gene (sacB) DNA, and 50 bp of the downstream homology arm of tdcDE gene, which was used for the first step of the homologous recombination.

The amplification system was as follows: Phusion 5× buffer (NewEngland Biolabs) 10 µl, dNTP (10 mM each) 1 µl, DNA template 20 ng, primers (10 µM) 2 µl each, Phusion High-Fidelity DNA polymerase (2.5 U/µl) 0.5 µl, distilled water 33.5 µl, with a total volume of 50 µl.

The amplification conditions were as follows: initial denaturation at 98° C. for 2 min (1 cycle); denaturation at 98° C. for 10 sec, annealing at 56° C. for 10 sec, extension at 72° C. for 2 min (30 cycles); and extension at 72° C. for 10 min (1 cycle).

The above DNA fragment I was used for the first homologous recombination: the pKD46 plasmid (*Escherichia coli* Genetic Stock Center, CGSC at Yale University, US, CGSC #7739) was firstly transforminged into *Escherichia coli* ATCC 8739 by electrotransformation, and then the DNA fragment I was electrotransformed to the *Escherichia coli* ATCC 8739 with pKD46.

The electrotransformation conditions were as follows: firstly preparing electroporation-competent cells of the *Escherichia coli* ATCC 8739 with pKD46 plasmid (prepared according to Dower et al., 1988, Nucleic Acids Res, 16:6127-6145); placing 50 µl of the competent cells on ice, adding 50 ng of the DNA fragment I, leaving the mixture on ice for 2 min, and transferring the mixture to a Bio-Rad's 0.2 cm-gap electroporation cuvette. A MicroPulser Electroporator (Bio-Rad) was used with electroporation parameter as 2.5 kV. Immediately after the electroporation, 1 ml of LB medium was transferred to the electroporation cuvette, and pipetted up and down 5 times, then transferred into a test tube, and incubated at 75 rpm and 30° C. for 2 h. A 200 μl bacterial suspension was taken and coated on a LB plate containing ampicillin (final concentration of 100 μg/ml) and chloramphenicol (final concentration of 34 μg/ml), and was incubated at 30° C. overnight. Single colonies were selected for PCR validation using the primers XZ-tdcDE-up/XZ-tdcDE-down, and the correct colony amplification product was a 3615-bp fragment containing 845 Bp of the tdcDE upstream homology arm, 2619 bp of the cat-sacB fragment and 151 bp of the tdcDE downstream homology arm. One correct single colony was selected and named as Span001.

In step two, using the wild-type *Bacillus subtilis* 168 genomic DNA as a template, a DNA fragment II of 1826 bp was amplified with the primers tdcDE-alsSin-up/tdcDE-alsSin-down, wherein the fragment comprises 50 bp of the tdcDE upstream homology arm, 1716 bp of the alsS gene, a total of 10 bp of the restriction enzyme cutting site and protective bases of sacI, and 50 bp of the tdcDE downstream homology arm. The DNA fragment II was used for the second homologous recombination. The amplification conditions and system were consistent with those described in step one. The DNA fragment II was electrotransformed to strain Span001.

The electrotransformation conditions were as follows: firstly preparing electrotransform-competent cells of the Span001 with pKD46 plasmid; placing 50 μl of the competent cells on ice, adding 50 ng of the DNA fragment II, placing the mixture on ice for 2 min, and transferring the mixture to a Bio-Rad's 0.2 cm-gap electroporation cuvette. A MicroPulser electroporator (Bio-Rad) was used with electroporation parameter as 2.5 kV. Immediately after electrotroporation, 1 ml of LB medium was transferred to the electroporation cuvette, and pipetted up and down 5 times, transferred into a test tube and then incubated at 75 rpm and 30° C. for 4 h. The bacterial suspension was transferred to LB liquid medium containing 10% of sucrose without sodium chloride (50 ml of medium in a 250 ml flask) and incubated for 24 hours, before streak culture on LB solid medium containing 6% of sucrose without sodium chloride. After PCR verification, the primers used were XZ-tdcDE-up/XZ-tdcDE-down, and the correct colony amplification product was a 2722 bp fragment, comprising 845 bp of the tdcDE upstream homology arm, a total of 1726 bp of the alsS gene and the restriction enzyme cutting site of sacI, and 151 bp of the tdcDE downstream homology arm. One correct single colony was selected and named Span002.

Span002 is a recombinant bacterium obtained by integrating the acetolactate synthase gene (alsS gene, the nucleotide sequence of said alsS gene is set forth as SEQ ID NO: 1, encoding the AlsS protein of SEQ ID NO: 2) into the loci of the tdcD gene encoding propionate kinase and the tdcE gene encoding formate acetyltransferase of *Escherichia coli* ATCC 8739, wherein the tdcD gene encoding propionate kinase (the encoded protein sequence is NCBI ACA76259.1, coded_by=CP000946.1:626900 . . . 628108) and the tdcE gene encoding formate acetyltransferase (the encoded protein sequence is NCBI ACA76260.1, coded_by=

CP000946.1:628142 . . . 630436) are simultaneously knocked out from the recombinant bacterium.

Example 2. Regulation of the alsS Gene Encoding Acetolactate Synthase

Starting from Span002, the expression of the alsS gene encoding acetolactate synthase, integrated at the tdcDE loci was regulated using an artificial regulatory element, which comprises specific steps as follows:

in step one, using the pXZ-CS plasmid DNA as a template, a DNA fragment I of 2719 bp was amplified using the primers tdcDE-incs-up/alsSPro-CS-down, wherein the fragment comprises 50 bp of the tdcDE upstream homology arm, 2619 bp of the cat-sacB fragment and 50 bp of the downstream homology arm of the alsS gene, which was used for the first step of the homologous recombination. The amplification system and amplification conditions were consistent with those described in Example 1. The DNA fragment I was electrotransformed to Span002.

The DNA fragment I was used for the first homologous recombination: firstly transforming the pKD46 plasmid to the *Escherichia coli* Span002 by electrotransformation, and then electrotransforming the DNA fragment I to the *Escherichia coli* Span002 with pKD46.

The electrotransformation conditions and steps were consistent with those for the step one of alsS integration at the tdcDE loci described in Example 1. A 200 μl bacterial suspension was taken and coated on a LB plate containing ampicillin (final concentration of 100 μg/ml) and chloramphenicol (final concentration of 34 μg/ml), and was incubated at 30° C. overnight. Single colonies were selected for PCR validation using the primers XZ-tdcDE-up/tdcDE-YZ285-down. The correct PCR product should be 3749 bp, comprising 845 bp of the tdcDE upstream homology arm, 2619 bp of the cat-sacB fragment and 285 bp of the alsS downstream homology arm. One correct single colony was selected and named Span003.

In step two, using the genomic DNA of M1-93 (Lu, et al., *Appl Microbiol Biotechnol*, 2012, 93:2455-2462) as a template, a DNA fragment II of 188 bp was amplified with the primers alsS-Pro-up/alsS-Pro-down, wherein the fragment comprises 50 bp of the tdcDE upstream homology arm, 88 bp of the M1-93 promoter, and 50 bp of the alsS downstream homology arm. The DNA fragment II was used for the second homologous recombination. The DNA fragment II was electrotransformed to strain Span003.

The electrotransformation conditions and steps were consistent with those for the step two of alsS integration at the tdcDE loci described in Example 1. The clone was validated by colony PCR with primers XZ-tdcDE-up/tdcDE-YZ285-down. The correct colony amplification product was a 1218 bp fragment comprising 8454 bp of the upstream homology arm of tdcDE, 88 bp of the M1-93 promoter sequence and 285 bp of the downstream homology arm of alsS. One correct single colony was selected and named Span004.

Span004 is a recombinant bacterium obtained by integrating the M1-93 promoter (the nucleotide sequence of said M1-93 promoter is set forth as SEQ ID NO: 3) to the upstream of the alsS gene in the *Escherichia coli* Span002, wherein the M1-93 promoter drives the expression of the alsS gene in this recombinant bacterium.

Example 3. Regulation of the ilvB Gene Encoding Acetolactate Synthase

The expression of the ilvB gene encoding the large subunit of acetolactate synthase I was regulated by a two-step homologous recombination method using the artificial regulatory element M1-93, which comprises specific steps as follows:

in step one, using the pXZ-CS plasmid DNA as a template, a DNA fragment I of 2719 bp was amplified using the primers ilvB pro-catup/ilvB pro-catdown, which was used for the first step of the homologous recombination. The DNA fragment I comprises 50 bp of the upstream homology arm of ilvB, 2619 bp of the cat-sacB fragment and 50 bp of the downstream homology arm of ilvB. The amplification system and amplification conditions were consistent with those described in Example 1.

The DNA fragment I was used for the first homologous recombination: firstly transforming the pKD46 plasmid to the *Escherichia coli* Span004 by electrotransformation, and then electrotransforming the DNA fragment I to the *Escherichia coli* Span004 with pKD46.

The electrotransformation conditions and steps were consistent with those for the step one of alsS integration at the tdcDE loci described in Example 1. A 200 µl bacterial suspension was taken and coated on a LB plate containing ampicillin (final concentration of 100 µg/ml) and chloramphenicol (final concentration of 34 µg/ml), and was incubated at 30° C. overnight. Single colonies were selected for PCR validation using the primers ilvB pro-YZup/ilvB pro-YZdown. The correct PCR product should be 2996 bp, containing 123 bp of ilvB upstream homology arm, 2619 bp of the cat-sacB fragment and 254 bp of ilvB downstream homology arm. One correct single colony was selected and named Span005.

In step two, using the genomic DNA of M1-93 (Lu, et al., *Appl Microbiol Biotechnol,* 2012, 93:2455-2462) as a template, a 188 bp DNA fragment II was amplified with primers ilvB pro-up/ilvB pro-down. The DNA fragment II comprises 50 bp of the ilvB upstream homology arm, 88 bp of the M1-93 promoter and 50 bp of the ilvB downstream homology arm. The DNA fragment II was used for the second homologous recombination. The DNA fragment II was electrotransformed to strain Span005.

The electrotransformation conditions and steps were consistent with those for the step two of alsS integration at the tdcDE loci described in Example 1. The clone was validated by colony PCR using the primers ilvB pro-YZup/ilvB pro-YZdown and the correct colony amplification product was a 465 bp fragment comprising 123 bp of the upstream homology arm of ilvB, 88 bp of the M1-93 promoter and 254 bp of the downstream homology arm of ilvB. One correct single colony was selected and named Span006.

Span006 is a recombinant bacterium obtained by integrating the M1-93 promoter (the nucleotide sequence of said M1-93 promoter is set forth as SEQ ID NO: 3) to the upstream of the ilvB gene encoding acetolactate synthase (the encoded protein sequence is NCBI ACA75715.1, coded_by=CP000946.1:28583 . . . 30271) of the *Escherichia coli* Span004, wherein the M1-93 promoter can drive the expression of the ilvB gene in this recombinant bacterium.

Example 4. Regulation of the ilvG Gene Encoding Acetolactate Synthase

The expression of the ilvG gene encoding the large subunit of acetolactate synthase II was regulated by a two-step homologous recombination method using the artificial regulatory element M1-93, which comprises specific steps as follows:

in step one, using the pXZ-CS plasmid DNA as a template, a 2719 bp DNA fragment I was amplified using the primers ilvG pro-catup/ilvG pro-catdown, which was used for the first step of the homologous recombination. The DNA fragment I comprises 50 bp of the ilvG upstream homology arm, 2619 bp of the cat-sacB fragment and 50 bp of the ilvG downstream homology arm. The amplification system and amplification conditions were consistent with those described in Example 1.

The DNA fragment I was used for the first homologous recombination: firstly transforming the pKD46 plasmid to the *Escherichia coli* Span006 by electrotransformation, and then electrotransforming the DNA fragment I to the *Escherichia coli* Span006 with pKD46.

The electrotransformation conditions and steps were consistent with those for the step one of alsS integration at the tdcDE loci described in Example 1. A 200 µl bacterial suspension was taken and coated on a LB plate containing ampicillin (final concentration of 100 µg/ml) and chloramphenicol (final concentration of 34 µg/ml), and was incubated at 30° C. overnight. Single colonies were selected for PCR validation using the primers ilvG pro-YZup/ilvG p-YZdown. The correct PCR product should be 2993 bp, comprising 179 bp of the ilvG upstream homology arm, 2619 bp of the cat-sacB fragment and 195 bp of the ilvG downstream homology arm. One correct single colony was selected and named Span007.

In step two, using the genomic DNA of M1-93 (Lu, et al., *Appl Microbiol Biotechnol,* 2012, 93:2455-2462) as a template, a 188 bp DNA fragment II was amplified with the primers ilvG pro-up/ilvG pro-down. The DNA fragment II comprises bp of the upstream homology arm of ilvG, 88 bp of the M1-93 promoter and 50 bp of the downstream homology arm of ilvG. The DNA fragment II was used for the second homologous recombination. The DNA fragment II was electrotransformed to strain Span007.

The electrotransformation conditions and steps were consistent with those for the step two of alsS integration at the tdcDE loci described in Example 1. The clone was verified by colony PCR using the primers ilvG pro-YZup/ilvG p-YZdown, and the correct colony amplification product was a 462 bp fragment comprising 179 bp of the upstream homology arm of ilvG, 88 bp of the M1-93 fragment and 195 bp of the downstream homology arm of ilvG. One correct single colony was selected and named Span008.

Span008 is a recombinant bacterium obtained by integrating the M1-93 promoter (the nucleotide sequence of said M1-93 promoter is set forth as SEQ ID NO: 3) to the upstream of the ilvG gene encoding acetolactate synthase (the encoded protein sequence is NCBI ACA79830.1, coded_by=CP000946.1:4677780 . . . 4679426) of the *Escherichia coli* Span006 bacterium, wherein the M1-93 promoter can drive the expression of the ilvG gene in this recombinant bacterium.

Example 5. Mutation of the ilvH Gene Encoding Acetolactate Synthase

Feedback inhibition by L-valine was relieved by introducing a mutation into the ilvH gene encoding a regulatory subunit of acetolactate synthase III through a two-step homologous recombination method, which comprises specific steps as follows:

in step one, using the pXZ-CS plasmid DNA as a template, a 2719 bp DNA fragment I was amplified using the primers ilvH*-cat-up/ilvH*-cat-down, which was used for the first step of the homologous recombination. The DNA fragment I comprises 50 bp of the upstream homology arm of ilvH, 2619 bp of the cat-sacB fragment and 50 bp of the downstream homology arm of ilvH. The amplification system and amplification conditions were consistent with those described in Example 1.

The DNA fragment I was used for the first homologous recombination: firstly transforming the pKD46 plasmid to the *Escherichia coli* Span008 by electrotransformation, and then electrotransforming the DNA fragment I to the *Escherichia coli* Span008 with pKD46.

The electrotransformation conditions and steps were consistent with those for the step one of alsS integration at the tdcDE loci described in Example 1. A 200 μl bacterial suspension was taken and coated on a LB plate containing ampicillin (final concentration of 100 μg/ml) and chloramphenicol (final concentration of 34 μg/ml), and was incubated at 30° C. overnight. Single colonies were selected for PCR validation using the primers ilvH*-mutYZ-up/ilvH*-mut-down. The correct PCR product should be 3165 bp, comprising 202 bp of the ilvH upstream homology arm, 2619 bp of the cat-sacB fragment and 344 bp of the ilvH downstream homology arm. One correct single colony was selected and named Span009.

In step two, using the DNA of wild-type *Escherichia coli* ATCC 8739 as a template, a DNA fragment II of 467 bp was amplified with primers ilvH*-mut-up/ilvH*-mut-down. The DNA fragment II was a mutated ilvH gene. The DNA fragment II was used for the second homologous recombination. The DNA fragment II was electrotransformed to strain Span009.

The electrotransformation conditions and steps were consistent with those for the step two of alsS integration at the tdcDE loci described in Example 1. The clone was validated by colony PCR with primers ilvH*-mutYZ-up/ilvH*-mut-down, and the correct colony amplification product was a 619 bp fragment comprising 163 bp of the upstream of the ilvH gene and 456 bp of the ilvH gene. One correct single colony was selected and named Span010.

Span010 is a recombinant bacterium obtained by mutating the ilvH gene encoding acetolactate synthase of *Escherichia coli* Span008 to the ilvH* gene (i.e., mutated ilvH gene). In this recombinant bacterium, the sequence of the ilvH* gene is set forth as SEQ ID NO: 4, encoding the IlvH* protein of SEQ ID NO: 5.

Example 6. Integration of an ilvC Gene Encoding Acetohydroxy-Acid Reductoisomerase at the Locus of adhE Gene Encoding Alcohol Dehydrogenase and Knockout of the adhE Gene Starting from Span010, an ilvC gene encoding acetohydroxy-acid reductoisomerase from *Escherichia coli*, was integrated to the locus of the adhE gene encoding alcohol dehydrogenase by a two-step homologous recombination method, which comprises specific steps as follows:

in step one, using the pXZ-CS plasmid DNA as a template, a DNA fragment I of a 2719 was amplified using the primers adhE-CS-up/adhE-CS-down, which was used for the first step of the homologous recombination. The DNA fragment I comprises 50 bp of the upstream homology arm of adhE, 2619 bp of the cat-sacB fragment and 50 bp of the downstream homology arm of adhE. The amplification system and amplification conditions were consistent with those described in Example 1. The DNA fragment I was electrotransformed to Span010.

The DNA fragment I was used for the first homologous recombination: firstly transforming the pKD46 plasmid (Datsenko and Wanner 2000, *Proc Natl Acad Sci USA*, 97:6640-6645; the plasmid purchased from *Escherichia coli* Genetic Stock Center, CGSC at Yale University, US, CGSC #7739) to the *Escherichia coli* Span010 by electrotransformation, and then the DNA fragment I was electrotransformed to the *Escherichia coli* Span010 with pKD46.

The electrotransformation conditions and steps were consistent with those for the step one of alsS integration at the tdcDE loci described in Example 1. A 200 μl bacterial suspension was taken and coated on a LB plate containing ampicillin (final concentration of 100 μg/ml) and chloramphenicol (final concentration of 34 μg/ml), and was incubated at 30° C. overnight. Single colonies were selected for PCR validation using the primers XZ-adhE-up/XZ-adhE-down. The correct PCR product should be 3167 bp, comprising 221 bp of the upstream homology arm of adhE, 2619 bp of the cat-sacB fragment and 327 bp of the downstream homology arm of adhE. One correct single colony was selected and named Span011.

In step two, using the genomic DNA of wild-type *Escherichia coli* ATCC 8739 as a template, a DNA fragment II of 1576 bp was amplified with the primers adhE-ilvC-up/adhE-ilvC-down. The DNA fragment II comprises 50 bp of the upstream homology arm of adhE, 1476 bp of the ilvC gene and 50 bp of the downstream homology arm of adhE. The DNA fragment II was used for the second homologous recombination. The DNA fragment II was electrotransformed to strain Span011.

The electrotransformation conditions and steps were consistent with those for the step two of alsS integration at the tdcDE loci described in Example 1. The clone was verified by colony PCR using the primers XZ-adhE-up/XZ-adhE-down, and the correct colony amplification product was a 2024 bp fragment comprising 221 bp of the upstream homology arm of adhE, 1476 bp of the ilvC gene and 327 bp of the downstream homology arm of adhE. One correct single colony was selected and named Span012.

Span012 is a recombinant bacterium obtained by integrating the ilvC gene encoding acetohydroxyl-acid reductoisomerase (the encoded protein sequence is NCBI ACA79824.1, coded_by=CP000946.1:4670539 . . . 4672014) into the adhE locus of the *Escherichia coli* Span010, wherein the adhE gene encoding alcohol dehydrogenase (encoding protein sequence is NCBI ACA78022.1, coded_by=CP000946.1:2627307 . . . 2629982) is simultaneously knocked out from this recombinant bacterium.

Example 7. Regulation of the ilvC Gene Encoding Acetohydroxy-Acid Reductoisomerase Starting from Span012, the expression of the ilvC gene encoding acetohydroxy-acid reductoisomerase integrated at the locus of the adhE gene encoding alcohol dehydrogenase was regulated using an artificial regulatory element, which comprises specific steps as follows:

in step one, using the pXZ-CS plasmid (Tan, et al., *Appl Environ Microbiol*, 2013, 79:4838-4844) DNA as a template, a DNA fragment I of 2719 bp was amplified using the primers adhE-cs-up/ilvC-ProCS-down which was used for the first step of homologous recombination. The DNA fragment I comprises 50 bp of the upstream homology arm of adhE, 2619 bp of the cat-sacB fragment and 50 bp of the downstream homology arm of ilvC. The amplification system and amplification conditions were consistent with those described in Example 1. The DNA fragment I was electrotransformed to Span012.

The DNA fragment I was used for the first homologous recombination: firstly transforming the pKD46 plasmid (Datsenko and Wanner 2000, *Proc Natl Acad Sci USA* 97:6640-6645; the plasmid purchased from *Escherichia coli* Genetic Stock Center, CGSC at Yale University, US, CGSC #7739) into the *Escherichia coli* Span012 by electrotransformation, and then the DNA fragment I was electrotransformed to the *Escherichia coli* Span012 with pKD46.

The electrotransformation conditions and steps were consistent with those for the step one of alsS integration at the tdcDE loci described in Example 1. A 200 μl bacterial suspension was taken and coated on a LB plate containing ampicillin (final concentration of 100 μg/ml) and chloramphenicol (final concentration of 34 μg/ml), and was incubated at 30° C. overnight. Single colonies were selected for PCR validation using the primers XZ-adhE-up/ilvC-YZ347-down. The correct PCR product should be 3187 bp, comprising 221 bp of the upstream homology arm of adhE, 2619 bp of the cat-sacB fragment and 347 bp of the downstream homology arm of ilvC. Once correct single colony was selected and named Span013.

In step two, using the genomic DNA of M1-46 (Lu, et al., *Appl Microbiol Biotechnol*, 2012, 93:2455-2462) as a template, a DNA fragment II of 188 bp was amplified with the primers ilvC-Pro-up/ilvC-Pro-down. The DNA fragment II comprises 50 bp of the upstream homology arm of adhE, 88 bp of the M1-46 promoter sequence and 50 bp of the downstream homology arm of ilvC. The DNA fragment II was used for the second homologous recombination. The DNA fragment II was electrotransformed to strain Span013.

The electrotransformation conditions and steps were consistent with those for the step two of alsS integration at the tdcDE loci described in Example 1. The clone was validated by colony PCR with the primers XZ-adhE-up/ilvC-YZ347-down, and the correct colony amplification product was a 656 bp fragment comprising 221 bp of the upstream homology arm of adhE, 88 bp of the M1-46 promoter and 347 bp of the downstream homology arm of ilvC. One correct single colony was selected and named Span014.

Span014 is a recombinant bacterium obtained by integrating the M1-46 promoter (nucleotide sequence is SEQ ID NO: 6 in the sequence list) to the upstream of the ilvC gene of *Escherichia coli* Span012, wherein the M1-46 promoter drives the expression of the ilvC gene in this recombinant bacterium.

Example 8. Integration of an ilvD Gene Encoding Dihydroxy-Acid Dehydratase at the Locus of pflB Gene Encoding Pyruvate Formate Lyase and Knockout of the pflB Gene Starting from Span014, an ilvD gene encoding dihydroxy-acid dehydratase from *Escherichia coli* was integrated to the locus of the pflB gene encoding pyruvate formate lyase and the pflB gene was knocked out by a two-step homologous recombination method, which comprises specific steps as follows:

in step one, using the pXZ-CS plasmid DNA as a template, a DNA fragment I of a 2719 bp was amplified using the primers pflB-CS-up/pflB-CS-down, which was used for the first step of homologous recombination. The DNA fragment I comprises 50 bp of the upstream homology arm of pflB, 2619 bp of the cat-sacB fragment and 50 bp of the downstream homology arm of pflB. The amplification system and amplification conditions were consistent with those described in Example 1. The DNA fragment I was electrotransformed to Span014.

The DNA fragment I was used for the first homologous recombination: firstly transforming the pKD46 plasmid to the *Escherichia coli* Span014 by electrotransformation, and then electrotransforming the DNA fragment I to the *Escherichia coli* Span014 with pKD46.

The electrotransformation conditions and steps were consistent with those for the step one of alsS integration at the tdcDE loci described in Example 1. A 200 μl bacterial suspension was taken and coated on a LB plate containing ampicillin (final concentration of 100 μg/ml) and chloramphenicol (final concentration of 34 μg/ml), and was incubated at 30° C. overnight. Single colonies were selected for PCR validation using the primers XZ-pflB-up600/XZ-pflB-down. The correct PCR product should be 3675 bp, comprising 641 bp of the pflB upstream homology arm, 2619 bp of the cat-sacB fragment and 415 bp of the pflB downstream homology arm. One correct single colony was selected and named Span015.

In step two, using the gene of *Escherichia coli* MG1655 (from ATCC, NO. 700926) as a template, a DNA fragment II of 1951 bp was amplified with the primers pflB-ilvD-up/pflB-ilvD-down. The DNA fragment II comprises 50 bp of the upstream homology arm of pflB, 1851 bp of the ilvD gene and 50 bp of the downstream homology arm of pflB. The DNA fragment II was used for the second homologous recombination. The DNA fragment II was electrotransformed to strain Span015.

The electrotransformation conditions and steps were consistent with those for the step two of alsS integration at the tdcDE loci described in Example 1. The clone was verified by colony PCR with the primers XZ-pflB-up600/XZ-pflB-down, and the correct colony amplification product was a 2996 bp fragment, comprising 641 bp of the upstream homology arm of pflB, 1851 bp of the ilvD gene and 415 bp of the downstream homology arm of pflB. One correct single colony was selected and named Span016.

Span016 is a recombinant bacterium obtained by integrating the ilvD gene encoding dihydroxy-acid dehydratase (the encoded protein sequence is NCBI QPA17447.1, coded_by=CP032679.1:3943375 . . . 3945225) to the pflB locus of *Escherichia coli* Span014, wherein the pflB gene encoding pyruvate formate lyase (the encoding protein sequence is NCBI ACA78322.1, coded_by=CP000946.1: 2956804 . . . 2959086) is simultaneously knocked out from the recombinant bacterium.

Example 9. Regulation of Expression of the ilvD Gene Encoding Dihydroxy-Acid Dehydratase Starting from Span016, the expression of the ilvD gene encoding dihydroxy-acid dehydratase integrated at the locus of the pflB gene encoding pyruvate formate lyase was regulated using an artificial regulatory element, which comprises specific steps as follows:

in step one, using the pXZ-CS plasmid DNA as a template, a DNA fragment I of a 2719 bp was amplified using the primers pflB-CS-up/pflB-Pcs-down, which was used for the first step of homologous recombination. The DNA fragment I comprises 50 bp of the upstream homology arm of pflB, 2619 bp of the cat-sacB fragment and 50 bp of the downstream homology arm of ilvD. The amplification system and amplification conditions were consistent with those described in Example 1. The DNA fragment I was electrotransformed to Span016.

The DNA fragment 1 was used for the first homologous recombination: firstly transforming the pKD46 plasmid into the *Escherichia coli* Span016 by electrotransformation, and then electrotransforming the DNA fragment I into the *Escherichia coli* Span016 with pKD46.

The electrotransformation conditions and steps were consistent with those for the step one of alsS integration at the tdcDE loci described in Example 1. A 200 μl bacterial suspension was taken and coated on a LB plate containing ampicillin (final concentration of 100 μg/ml) and chloramphenicol (final concentration of 34 μg/ml), and was incubated at 30° C. overnight. Single colonies were selected for PCR validation using the primers XZ-pflB-up600/ilvD-YZ496-down. The correct PCR product should be 3756 bp, comprising 641 bp of the pflB upstream homology arm, 2619 bp of the cat-sacB fragment and 496 bp of the ilvD downstream homology arm. One correct single colony was selected and named Span017.

In step two, using the genomic DNA of M1-93 (Lu, et al., *Appl Microbiol Biotechnol,* 2012, 93:2455-2462) as a template, a DNA fragment II of 189 bp to amplified with the primers pflB-Pro-up/ilvD-Pro-down. The DNA fragment II comprises 50 bp of the upstream homology arm of pflB, 89 bp of the artificial regulatory element RBSL1 sequence and 50 bp of the downstream homology arm of ilvD. The DNA fragment II was used for the second homologous recombination. The DNA fragment II was electrotransformed to strain Span017.

The electrotransformation conditions and steps were consistent with those for the step two of alsS integration at the tdcDE loci described in Example 1. The clone was validated by colony PCR with the primers XZ-pflB-up600/ilvD-YZ496-down, and the correct colony amplification product was a 1226 bp fragment comprising 641 bp of the upstream homology arm of pflB, 89 bp of the RBSL1 sequence and 496 bp of the downstream homology arm of ilvD. One correct single colony was selected and named Span018.

Span018 is a recombinant bacterium obtained by integrating the RBSL1 promoter (the nucleotide sequence of said RBSL1 promoter is set forth as SEQ ID NO: 7) to the upstream of the ilvD gene of *Escherichia coli* Span016, wherein the RBSL1 promoter drives the expression of the ilvD gene in this recombinant bacterium.

Example 10. Integration of a panB Gene Encoding 3-Methyl-2-Oxobutanoate Hydroxymethyltransferase at the Locus of Frd Gene Encoding Fumarate Reductase and Knockout of the Frd Locus Starting from Span018, a panB gene encoding 3-methyl-2-oxobutanoate hydroxymethyltransferase was integrated to the locus of the frd gene encoding fumarate reductase, which comprises specific steps as follows:

in step one, using the pXZ-CS plasmid DNA as a template, a DNA fragment I of a 2719 bp was amplified using the primers frd-cs-up/frd-cs-down, which was used for the first step of homologous recombination. The DNA fragment I comprises 50 bp of the upstream homology arm of frd, 2619 bp of the cat-sacB fragment and 50 bp of the downstream homology arm of frd. The amplification system and amplification conditions were consistent with those described in Example 1. The DNA fragment I was electrotransformed to Span018.

The DNA fragment I was used for the first homologous recombination: firstly transforming the pKD46 plasmid into the *Escherichia coli* Span018 by electrotransformation, and then electrotransforming the DNA fragment I into the *Escherichia coli* Span018 with pKD46.

The electrotransformation conditions and steps were consistent with those for the step one of alsS integration at the tdcDE loci described in Example 1. A 200 μl bacterial suspension was taken and coated on a LB plate containing ampicillin (final concentration of 100 μg/ml) and chloramphenicol (final concentration of 34 ng/ml), and was incubated at 30° C. overnight. Single colonies were selected for PCR validation using the primers XZ-frd-up/XZ-frd-down. The correct PCR product should be 3440 bp, comprising 426 bp of the frd upstream homology arm, 2619 bp of the cat-sacB fragment and 395 bp of the frd downstream homology arm. One correct single colony was selected and named Span019.

In step two, using the genomic DNA of *Escherichia coli* MG1655 (from ATCC, NO. 700926) as a template, a DNA fragment II of 895 bp was amplified using the primers frd-panB-up/frd-panB-down. The DNA fragment 11 comprises 50 bp of the frd upstream homology arm, 795 bp of the panB gene and 50 bp of the frd downstream homology arm. The DNA fragment II was used for the second homologous recombination. The DNA fragment II was electrotransformed to strain Span019.

The electrotransformation conditions and steps were consistent with those for the step two of alsS integration at the tdcDE loci described in Example 1. The clone was validated by colony PCR with the primers XZ-frd-up/XZ-frd-down, and the correct colony amplification product was a 1661 bp fragment comprising 426 bp of the upstream homology arm of frd, 795 bp of the panB gene and 395 bp of the downstream homology arm of frd. One correct single colony was selected and named Span020.

Span020 is a recombinant bacterium obtained by integrating the panB gene encoding 3-methyl-2-oxobutanoate hydroxymethyltransferase (the encoded protein sequence is NCBI QPA14045.1, coded_by=CP032679.1:148806 . . . 149600) to the frd locus of *Escherichia coli* Span018, wherein the frd gene encoding fumarate reductase (the encoded protein sequence is NCBI ACA79462.1, coded_by=CP000946.1:4217304 . . . 4217699) is simultaneously knocked out from this recombinant bacterium.

Example 11. Regulation of Expression of the panB Gene Encoding 3-methyl-2-oxobutanoate hydroxymethyltransferase Starting from Span020, the expression of the panB gene encoding the 3-methyl-2-oxobutanoate hydroxymethyltransferase integrated at the locus of the frd gene encoding fumarate reductase, was regulated using an artificial regulatory element, which comprises specific steps as follows:

in step one, using the pXZ-CS plasmid DNA as a template, a 2719 bp DNA fragment I was amplified using the primers frd-cs-up/panB-Pcs-down, which was used for the first step of homologous recombination. The DNA fragment I comprises 50 bp of the upstream homology arm of frd, 2619 bp of the cat-sacB fragment and 50 bp of the downstream homology arm of panB. The amplification system and amplification conditions were consistent with those described in Example 1. The DNA fragment I was electrotransformed to Span020.

The DNA fragment I was used for the first homologous recombination: firstly transforming the pKD46 plasmid into the *Escherichia coli* Span020 by electrotransformation, and then electrotransforming the DNA fragment I into the *Escherichia coli* Span020 with pKD46.

The electrotransformation conditions and steps were consistent with those for the step one of alsS integration at the tdcDE loci described in Example 1. A 200 µl bacterial suspension was taken and coated on a LB plate containing ampicillin (final concentration of 100 µg/ml) and chloramphenicol (final concentration of 34 µg/ml), and was incubated at 30° C. overnight. Single colonies were selected for PCR validation using the primers XZ-frd-up/panB-YZ130-down. The correct PCR product should be 3175 bp, comprising 426 bp of the frd upstream homology arm, 2619 bp of the cat-sacB fragment and 130 bp of the panB downstream homology arm. One correct single colony was selected and named Span021.

In step two, using the genomic DNA of M1-93 (Lu, et al., *Appl Microbiol Biotechnol*, 2012, 93:2455-2462) as a template, a DNA fragment II was amplified with the primers panB-Pro-up/panB-Pro-down. The DNA fragment II comprises 50 bp of the frd upstream homology arm, 88 bp of the M1-93 promoter sequence and 50 bp of the downstream homology arm of panB. The DNA fragment II was used for the second homologous recombination. The DNA fragment II was electrotransformed to strain Span021.

The electrotransformation conditions and steps were consistent with those for the step two of alsS integration at the tdcDE loci described in Example 1. The clone was verified by colony PCR using the primers XZ-frd-up/panB-YZ130-down and the correct colony amplification product was a 644 bp fragment comprising 426 bp of the upstream homology arm of frd. 88 bp of the M1-93 promoter sequence and 130 bp of the downstream homology arm of panB. One correct single colony was selected and named Span022.

Span022 is a recombinant bacterium obtained by integrating the M1-93 promoter (the nucleotide sequence of said M1-93 promoter is set forth as SEQ ID NO: 3) to the upstream of the panB gene of *Escherichia coli* Span020, wherein the M1-93 promoter drives the expression of the panB gene in this recombinant bacterium.

Example 12. Integration of a panE Gene Encoding 2-dehydropantothenate-2-reductase at the Locus of IdhA Gene Encoding Lactate Dehydrogenase and Knockout of the ldhA Locus Starting from Span022, a panE gene encoding 2-dehydropantothenate-2-reductase was integrated to the locus of the ldhA gene encoding lactate dehydrogenase, which comprises specific steps as follows:

in step one, using the pXZ-CS plasmid DNA as a template, a 2719 bp DNA fragment I was amplified using the primers IdhA-csin-up/ldhA-csin-down, which was used for the first step of homologous recombination. The amplification system and amplification conditions were consistent with those described in Example 1. The DNA fragment I was electrotransformed to Span022.

The DNA fragment I was used for the first homologous recombination: firstly transforming the pKD46 plasmid into the *Escherichia coli* Span022 by electrotransformation, and then electrotransforming the DNA fragment I into the *Escherichia coli* Span022 with pKD46.

The electrotransformation conditions and steps were consistent with those for the step one of alsS integration at the tdcDE loci described in Example 1. A 200 µl bacterial suspension was taken and coated on a LB plate containing ampicillin (final concentration of 100 µg/ml) and chloramphenicol (final concentration of 34 µg/ml), and was incubated at 30° C. overnight. Single colonies were selected for PCR validation using the primers XZ-ldhA-up/XZ-IdhA-down. The correct PCR product should be 3415 bp, comprising 380 bp of the IdhA upstream homology arm, 2619 bp of the cat-sacB fragment and 416 bp of the ldhA downstream homology arm. One correct single colony was selected and named Span023.

In step two, using the genomic DNA of *Escherichia coli* MG1655 (from ATCC, no. 700926) as a template, a 1012 bp DNA fragment II was amplified with the primers IdhA-panE-up/IdhA-panE-down. The DNA fragment II comprises 50 bp of the upstream homology arm of IdhA, 912 bp of the panE gene and 50 bp of the IdhA downstream homology arm. The DNA fragment II was used for the second homologous recombination. The DNA fragment II was electrotransformed to strain Span023.

The electrotransformation conditions and steps were consistent with those for the step two of alsS integration at the tdcDE loci described in Example 1. The clone was validated by colony PCR using the primers XZ-IdhA-up/XZ-ldhA-down and the correct colony amplification product was a 1708 bp fragment comprising 380 bp of the upstream homology arm of IdhA, 912 bp of the panE gene and 416 bp of the downstream homology arm of IdhA. One correct single colony was selected and named Span024.

Span024 is a recombinant bacterium obtained by integrating the panE gene encoding 2-dehydropantothenate-2-reductase (the encoded protein sequence is NCBI QPA14304.1, coded_by=CP032679.1:443607 . . . 444518) to the IdhA locus of *Escherichia coli* Span022, wherein the lactate dehydrogenase gene IdhA (the encoded protein sequence is NCBI ACA77911.1, coded_by=CP000946.1: 2508048 . . . 2509037) is simultaneously knocked out from recombinant bacterium.

Example 13. Regulation of Expression of the panE Gene Encoding 2-dehydropantothenate-2-reductase Starting from Span024, the expression of the panE gene encoding 2-dehydropantothenate-2-reductase integrated at the locus of the IdhA gene encoding lactate dehydrogenase was regulated using an artificial regulatory element, which comprises specific steps as follows:

in step one, using the pXZ-CS plasmid DNA as a template, a 2719 bp DNA fragment I was amplified using the primers IdhA-csin-up/panE-ProCS-down, which was used for the first step of homologous recombination. The DNA fragment I comprises 50 bp of the upstream homology arm of IdhA, 2619 bp of the cat-sacB fragment and 50 bp of the downstream homology arm of panE. The amplification system and amplification conditions were consistent with those described in Example 1. The DNA fragment I was electrotransformed to Span024.

The DNA fragment I was used for the first homologous recombination: firstly transforming the pKD46 plasmid into the *Escherichia coli* Span024 by electrotransformation, and then electrotransforming the DNA fragment I into the *Escherichia coli* Span024 with pKD46.

The electrotransformation conditions and steps were consistent with those for the step one of alsS integration at the tdcDE loci described in Example 1. A 200 µl bacterial suspension was taken and coated on a LB plate containing ampicillin (final concentration of 100 µg/ml) and chloramphenicol (final concentration of 34 μg/ml), and was incubated at 30° C. overnight. Single colonies were selected for PCR validation using the primers XZ-ldhA-up/panE-YZ245-down. The correct PCR product should be 3244 bp, comprising 380 bp of the IdhA upstream homology arm, 2619 bp of the cat-sacB fragment and 245 bp of the panE downstream homology arm. One correct single colony was selected and named Span025.

In step two, using the genomic DNA of M1-93 (Lu, et al., *Appl Microbiol Biotechnol,* 2012, 93:2455-2462) as a template, a 189 bp DNA fragment II was amplified with the primers panE-Pro-up/panE-Pro-down. The DNA fragment II comprises 50 bp of the ldhA upstream homology arm, 89 bp of the artificial promoter RBSL2 sequence and 50 bp of panE downstream homology arm. The DNA fragment II was used for the second homologous recombination. The DNA fragment II was electrotransformed to strain Span025.

The electrotransformation conditions and steps were consistent with those for the step two of alsS integration at the tdcDE loci described in Example 1. The clone was verified by colony PCR using the primers XZ-IdhA-up/panE-YZ245-down, and the correct colony amplification product was a 714 bp fragment comprising 380 bp of the upstream homology arm of IdhA, 89 bp of the artificial promoter RBSL2 sequence and 245 bp of the downstream homology arm of panE. One correct single colony was selected and named Span026.

Span026 is a recombinant bacterium obtained by integrating the RBSL2 promoter (the nucleotide sequence of said RBSL2 promoter is set forth as SEQ ID NO: 8) to the upstream of the panE gene of *Escherichia coli* Span024, wherein the RBSL2 promoter drives the expression of the panE gene in this recombinant bacterium.

Example 14. Integration of a glyA Gene Encoding Glycine Hydroxymethyltransferase at the Locus of mgsA Gene Encoding Methylglyoxal Synthase and Knockout of the mgsA Locus Starting from Span026, a glyA gene encoding glycine hydroxymethyltransferase was integrated at the locus of the mgsA gene encoding methylglyoxal synthase, which comprises specific steps as follows:

In step one, using the pXZ-CS plasmid DNA as a template, a 2719 bp DNA fragment I was amplified using the primers mgsA-cs-up/mgsA-cs-down, which was used for the first step of homologous recombination. The DNA fragment I comprises bp of the upstream homology arm of mgsA, 2619 bp of the cat-sacB fragment and bp of the downstream homology arm of mgsA. The amplification system and amplification conditions were consistent with those described in Example 1. The DNA fragment I was electrotransformed to Span026.

The DNA fragment I was used for the first homologous recombination: firstly transforming the pKD46 plasmid into the *Escherichia coli* Span026 by electrotransformation, and then electrotransforming the DNA fragment I into the *Escherichia coli* Span026 with pKD46.

The electrotransformation conditions and steps were consistent with those for the step one of alsS integration at the tdcDE loci described in Example 1. A 200 μl bacterial suspension was taken and coated on a LB plate containing ampicillin (final concentration of 100 μg/ml) and chloramphenicol (final concentration of 34 μg/ml), and was incubated at 30° C. overnight. Single colonies were selected for PCR validation using the primers XZ-mgsA-up/XZ-mgsAdown. The correct PCR product should be 3646 bp, comprising 516 bp of the mgsA upstream homology arm, 2619 bp of the cat-sacB fragment and 511 bp of the mgsA downstream homology arm. One correct single colony was selected and named Span027.

In step two, using the genomic DNA of wild-type *Escherichia coli* ATCC8739 as a template, a DNA fragment II of 1354 bp was amplified with the primers mgsA-glyA-up/mgsA-glyA-down. The DNA fragment II comprises 50 bp of the mgsA upstream homology arm, 1254 bp of the glyA fragment and 50 bp of the mgsA downstream homology arm. The DNA fragment II was used for the second homologous recombination. The DNA fragment II was electrotransformed to strain Span027.

The electrotransformation conditions and steps were consistent with those for the step two of alsS integration at the tdcDE loci described in Example 1. The clone was verified by colony PCR using the primers XZ-mgsA-up/XZ-mgsA-down, and the correct colony amplification product was a 2281 bp fragment comprising 516 bp of the upstream homology arm of mgsA, 1254 bp of the glyA fragment and 511 bp of the downstream homology arm of mgsA. One correct single colony was selected and named Span028.

Span028 is a recombinant bacterium obtained by integrating the glyA gene encoding glycine hydroxymethyltransferase (the encoded protein sequence is NCBI ACA76793.1, coded_by=CP000946.1:1227416 . . . 1228669) to the mgsA locus of *Escherichia coli* Span026, wherein the mgsA gene (the encoded protein sequence is NCBIACA78263.1, coded_by=CP000946.1:2883345 . . . 2883803) is simultaneously knocked out from this recombinant bacterium.

Example 15. Regulation of the glyA Gene Encoding Glycine Hydroxymethyltransferase Starting from Span028, the expression of the glyA gene encoding glycine hydroxymethyltransferase integrated at the mgsA locus was regulated using an artificial regulatory element, which comprises specific steps as follows:

in step one, using the pXZ-CS plasmid DNA as a template, a 2719 bp DNA fragment I was amplified using the primers mgsA-cs-up/glyA-ProCS-down, which was used for the first step of homologous recombination. The DNA fragment I comprises bp of the upstream homology arm of mgsA, 2619 bp of the cat-sacB fragment and bp of the downstream homology arm of glyA. The amplification system and amplification conditions were consistent with those described in Example 1. The DNA fragment I was electrotransformed to Span028.

The DNA fragment I was used for the first homologous recombination: firstly transforming the pKD46 plasmid to the *Escherichia coli* Span028 by electrotransformation, and then electrotransforming the DNA fragment I to the *Escherichia coli* Span028 with pKD46.

The electrotransformation conditions and steps were consistent with those for the step one of alsS integration at the tdcDE loci described in Example 1. A 200 μl bacterial suspension was taken and coated on a LB plate containing ampicillin (final concentration of 100 μg/ml) and chloramphenicol (final concentration of 34 μg/ml), and was incubated at 30° C. overnight. Single colonies were selected for PCR validation using the primers XZ-mgsA-up/glyA-YZ364-down. The correct PCR product should be 3499 bp, comprising 516 bp of the mgsA upstream homology arm, 2619 bp of cat-sacB fragment and 364 bp of the glyA downstream homology arm. One correct single colony was selected and named Span029.

In step two, using the genomic DNA of M1-46 (Lu, et al., *Appl Microbiol Biotechnol*, 2012, 93:2455-2462) as a template, a 188 bp DNA fragment II was amplified with the primers glyA-Pro-up/glyA-Pro-down. The DNA fragment II comprises 50 bp of the mgsA upstream homology arm, 88 bp of the M1-46 promoter and 50 bp of the glyA downstream homology arm. The DNA fragment II was used for the second homologous recombination. The DNA fragment II was electrotransformed to strain Span029.

The electrotransformation conditions and steps were consistent with those for the step two of alsS integration at the tdcDE loci described in Example 1. The clone was validated by colony PCR with the primers XZ-mgsA-up/glyA-YZ364-down, and the correct colony amplification product was a 968 bp fragment comprising 516 bp of the upstream homology arm of mgsA, 88 bp of the M1-46 promoter and 364 bp of the downstream homology arm of glyA. One correct single colony was selected and named Span030.

Span030 is a recombinant bacterium obtained by integrating the M1-46 promoter (the nucleotide sequence is set forth as SEQ ID NO: 6) to the upstream of the glyA gene in Span028, wherein the M1-46 promoter drives the expression of the glyA gene in this recombinant bacterium.

Example 16. Regulation of the gcvT Gene Encoding Aminomethyltransferase of Wild-Type *Escherichia coli*

Starting from Span030, the expression of the gcvT gene encoding aminomethyltransferase of wild-type *Escherichia coli* was regulated using an artificial regulatory element, which comprises specific steps as follows:

in step one, using the pXZ-CS plasmid DNA as a template, a 2719 bp DNA fragment I was amplified using the primers gcvT-Pcat-up/gcvT-PsacB-down, which was used for the first step of homologous recombination. The DNA fragment I comprises 50 bp of the upstream homology arm of the gcvT gene, 2619 bp of the cat-sacB fragment and 50 bp of the downstream homology arm of gcvT. The amplification system and amplification conditions were consistent with those described in Example 1. The DNA fragment I was electrotransformed to Span030.

The DNA fragment I was used for the first homologous recombination: firstly transforming the pKD46 plasmid into the *Escherichia coli* Span030 by electrotransformation, and then electrotransforming the DNA fragment I into the *Escherichia coli* Span030 with pKD46.

The electrotransformation conditions and steps were consistent with those for the step one of alsS integration at the tdcDE loci described in Example 1. A 200 μl bacterial suspension was taken and coated on a LB plate containing ampicillin (final concentration of 100 μg/ml) and chloramphenicol (final concentration of 34 μg/ml), and was incubated at 30° C. overnight. Single colonies were selected for PCR validation using the primers gcvT-up-500/gcvT-350-down. The correct PCR product should be 3197 bp, comprising 228 bp of the upstream homology arm of the gcvT gene, 2619 bp of the cat-sacB fragment and 350 bp of the downstream homology arm of gcvT. One correct single colony was selected and named Span031.

In step two, using the genomic DNA of M1-93 (Lu, et al., *Appl Microbiol Biotechnol*, 2012, 93:2455-2462) as a template, a 188 bp DNA fragment II was amplified with the primers gcvT-M93-up/gcvT-M93-down. The DNA fragment II comprises 50 bp of the gcvT gene upstream homology arm, 88 bp of the M1-93 promoter and 50 bp of the gcvT downstream homology arm. The DNA fragment II was used for the second homologous recombination. The DNA fragment II was electrotransformed to strain Span031.

The electrotransformation conditions and steps were consistent with those for the step two of alsS integration at the tdcDE loci described in Example 1. The clone was verified by colony PCR using the primers gcvT-up-500/gcvT-350-down, and the correct colony amplification product was a 666 bp fragment comprising 228 bp of the upstream homology arm of the gcvT gene, 88 bp of the M1-93 promoter and 350 bp of the downstream homology arm of gcvT. One correct single colony was selected and named Span032.

Span032 is a recombinant bacterium obtained by integrating the M1-93 promoter (the nucleotide sequence of M1-93 promoter is set forth as SEQ ID NO: 3) to the upstream of the gcvT gene encoding aminomethyltransferase (the encoded protein sequence is NCBI ACA76476.1, coded_by=CP000946.1:862077 . . . 863171) of *Escherichia coli* Span030, wherein the M1-93 promoter can drive the expression of the gcvT gene in this recombinant bacterium.

Example 17. Regulation of the gcvP Gene Encoding Glycine Decarboxylase of Wild-Type *Escherichia coli*

Starting from Span032, the expression of the gcvP gene encoding glycine decarboxylase of wild-type *Escherichia coli* was regulated using an artificial regulatory element, which comprises specific steps as follows:

in step one, using the pXZ-CS plasmid DNA as a template, a 2719 bp DNA fragment I was amplified using the primers gcvP-Pcat-up/gcvP-PsacB-down, which was used for the first step of homologous recombination. The DNA fragment I comprises 50 bp of the upstream homology arm of the gcvP gene, 2619 bp of the cat-sacB fragment and 50 bp of the downstream homology arm of gcvP. The amplification system and amplification conditions were consistent with those described in Example 1. The DNA fragment I was electrotransformed to Span032.

The DNA fragment I was used for the first homologous recombination: firstly transforming the pKD46 plasmid into the *Escherichia coli* Span032 by electrotransformation, and then electrotransforming the DNA fragment I into the *Escherichia coli* Span032 with pKD46.

The electrotransformation conditions and steps were consistent with those for the step one of alsS integration at the tdcDE loci described in Example 1. A 200 μl bacterial suspension was taken and coated on a LB plate containing ampicillin (final concentration of 100 μg/ml) and chloramphenicol (final concentration of 34 μg/ml), and was incubated at 30° C. overnight. Single colonies were selected for PCR validation using the primers gcvH-up gcvP-390-down. The correct PCR product should be 3399 bp, comprising 390 bp of the gcvP gene upstream homology arm, 2619 bp of the cat-sacB fragment and 390 bp of gcvP downstream homology arm. One correct single colony was selected and named Span033.

In step two, using the genomic DNA of M1-93 (Lu, et al., *Appl Microbiol Biotechnol*, 2012, 93:2455-2462) as a template, a 188 bp DNA fragment II was amplified with the primers gcvP-M93-up/gcvP-M93-down. The DNA fragment II comprises 50 bp of the gcvP gene upstream homology arm, 88 bp of M1-93 promoter and 50 bp of the gcvP downstream homology arm. The DNA fragment II was used for the second homologous recombination. The DNA fragment II was electrotransformed to strain Span033.

The electrotransformation conditions and steps were consistent with those for the step two of alsS integration at the tdcDE loci described in Example 1. The clone was validated by colony PCR with the primers gcvH-up/gcvP-390-down and the correct colony amplification product was an 868 bp fragment comprising 390 bp of the upstream homology arm of the gcvP gene, 88 bp of the M1-93 promoter and 390 bp of the downstream homology arm of gcvP. One correct single colony was selected and named Span034.

Span034 is a recombinant bacterium obtained by integrating the M1-93 promoter (the nucleotide sequence of said M1-93 promoter is set forth as SEQ ID NO: 3) to the upstream of the glycine decarboxylase gene gcvP (the encoded protein sequence is NCBI ACA76478.1, coded_by=CP000946.1:863703 . . . 866576) of *Escherichia coli* Span032, wherein the M1-93 promoter can drive the expression of the gcvP gene in this recombinant bacterium.

Example 18. Integration of a panB Gene Encoding 3-Methyl-2-Oxobutanoate Hydroxymethyltransferase from *Corynebacterium glutamicum* at the Loci of the Pta Gene Encoding Phosphate Acetyltransferase and the ackA Gene Encoding Acetate Kinase and Knockout of the ackA-Pta Loci Starting from Span034, a panB gene encoding 3-methyl-2-oxobutanoate hydroxymethyltransferase from *Corynebacterium glutamicum* was integrated at the loci of the pta gene encoding phosphate acetyltransferase and the ackA gene encoding acetate kinase, which comprises specific steps as follows:

in step one, using the pXZ-CS plasmid DNA as a template, a 2719 bp DNA fragment I was amplified using the primers ackA-cs-up/pta-cs-down, which was used for the first step of homologous recombination. The DNA fragment I comprises 50 bp of the upstream homology arm of the ackA-pta gene, 2619 bp of the cat-sacB fragment, 50 bp of the downstream homology arm of the ackA-pta gene. The amplification system and amplification conditions were consistent with those described in Example 1. The DNA fragment I was electrotransformed to Span034.

The DNA fragment I was used for the first homologous recombination: firstly transforming the pKD46 plasmid into the *Escherichia coli* Span034 by electrotransformation, and then electrotransforming the DNA fragment I into the *Escherichia coli* Span034 with pKD46.

The electrotransformation conditions and steps were consistent with those for the step one of alsS integration at the tdcDE loci described in Example 1. A 200 µl bacterial suspension was taken and coated on a LB plate containing ampicillin (final concentration of 100 µg/ml) and chloramphenicol (final concentration of 34 Kg/ml), and was incubated at 30° C. overnight. Single colonies were selected for PCR validation using the primers XZ-ackA-up/XZ-pta-down. The correct PCR product should be 3350 bp, comprising 320 bp of the ackA-pta gene upstream homology arm, 2619 bp of the cat-sacB fragment and 411 bp of the ackA-pta downstream homology arm. One correct single colony was selected and named Span035.

In step two, using the genomic DNA of *Corynebacterium glutamicum* ATCC13032 (ATCC product) as a template, a 916 bp DNA fragment II was amplified using the primers ackA-panBC-up/ackA-panBC-down. The DNA fragment II comprises 50 bp of the upstream homology arm of the ackA-pta gene, 816 bp of the panB gene from *Corynebacterium glutamicum* and 50 bp of the downstream homology arm of the ackA-pta gene, which was used for the second homologous recombination. The DNA fragment II was electrotransformed to strain Span035.

The electrotransformation conditions and steps were consistent with those for the step two of alsS integration at the tdcDE loci described in Example 1. The clone was validated by colony PCR with primers XZ-ackA-up/XZ-pta-down. The correct colony amplification product was a fragment of 1547 bp, comprising 320 bp of the upstream homology arm of the ackA-pta gene, 816 bp of the panB gene from *Corynebacterium glutamicum* and 411 bp of the downstream homology arm of ackA-pta. One correct single colony was selected and named Span036.

Span036 is a recombinant bacterium obtained by integrating the panB gene encoding 3-methyl-2-oxobutanoate hydroxymethyltransferase of *Corynebacterium glutamicum* (panB gene, whose nucleotide sequence is set forth as SEQ ID NO: 9, encoding the PanB protein of SEQ ID NO: 10) to the loci of the pta gene encoding phosphate acetyltransferase and the ackA gene encoding acetate kinase of *Escherichia coli* Span034, wherein the pta gene (the encoded protein sequence is NCBI ACA77021.1, coded_by=CP000946.1: 1484032 . . . 1486176) and ackA gene (encoding protein sequence NCBI ACA77022.1, coded_by=CP000946.1: 1486251 . . . 1487453) are simultaneously knocked out from this recombinant bacterium.

Example 19 Regulation of the panB Gene Encoding 3-methyl-2-oxobutanoate hydroxymethyltransferase of *Corynebacterium glutamicum* Origin Starting from Span 036, the expression of the panB gene encoding 3-methyl-2-oxobutanoate hydroxymethyltransferase integrated at the ackA-pta loci was regulated using an artificial regulatory element, which comprises specific steps as follows:

in step one, using the pXZ-CS plasmid DNA as a template, a 2719 bp DNA fragment I was amplified using the primers ackA-cs-up/panBC-ProCS-down, which was used for the first step of homologous recombination. The DNA fragment I comprises 50 bp of the upstream homology arm of the ackA-pta gene, 2619 bp of the cat-sacB fragment and 50 bp of the downstream homology arm of the ackA-pta gene from *Corynebacterium glutamicum*. The amplification system and amplification conditions were consistent with those described in Example 1. The DNA fragment I was electrotransformed to Span036.

The DNA fragment I was used for the first homologous recombination: firstly transforming the pKD46 plasmid to the *Escherichia coli* Span036 by electrotransformation, and then electrotransforming the DNA fragment I to the *Escherichia coli* Span036 with pKD46.

The electrotransformation conditions and steps were consistent with those for the step one of alsS integration at the tdcDE loci described in Example 1. A 200 µl bacterial suspension was taken and coated on a LB plate containing ampicillin (final concentration of 100 µg/ml) and chloramphenicol (final concentration of 34 µg/ml), and was incubated at 30° C. overnight. Single colonies were selected for PCR validation using the primers XZ-ackA-up/panBC-YZ425-down. The correct PCR product should be 3364 bp, comprising 320 bp of the upstream homology arm of the ackA-pta gene, 2619 bp for the cat-sacB fragment and 425 bp for the downstream homology arm of panB. One correct single colony was selected and named Span037.

In step two, using the genomic DNA of M1-93 (Lu, et al., *Appl Microbiol Biotechnol,* 2012, 93:2455-2462) as a template, a 188 by DNA fragment II was amplified with primers panBC-Pro-up/panBC-Pro-down. The DNA fragment II comprises 50 bp of the ackA-pta gene upstream homology arm, 88 bp of the M1-93 promoter and 50 bp of the panB downstream homology arm. The DNA fragment II was used for the second homologous recombination. The DNA fragment II was electrotransformed to strain Span037.

The electrotransformation conditions and steps were consistent with those for the step two of alsS integration at the tdcDE loci described in Example 1. The clone was validated by colony PCR with the primers XZ-ackA-up/panBC-YZ425-down, and the correct colony amplification product was an 833 bp fragment comprising 320 bp of the upstream homology arm of the ackA-pta gene, 88 bp of the M1-93 promoter and 425 bp of the downstream homology arm of panB. One correct single colony was selected and named Span038.

Span038 is a recombinant bacterium obtained by integrating the M1-93 promoter (the nucleotide sequence of M1-93 promoter is set forth as SEQ ID NO: 3) to the upstream of the panB gene of *Escherichia coli* Span036, wherein the M1-93 promoter drives the expression of the panB gene.

Example 20. Expression Attenuation of the ilvE Gene Encoding Branched-Chain Amino Acid Aminotransferase Starting from Span038, the expression of the ilvE gene encoding branched-chain amino acid aminotransferase was attenuated, which comprises specific steps as follows:

In step one, using the pXZ-CS plasmid DNA as a template, a 2719 bp DNA fragment I was amplified using the primers ilvE-cat-up/ilvE-sacB-down, which was used for the first step of homologous recombination. The DNA fragment I comprises bp of the upstream homology arm of the ilvE gene, 2619 bp of the cat-sacB fragment and 50 bp of the downstream homology arm of the ilvE gene. The amplification system and amplification conditions were consistent with those described in Example 1. The DNA fragment I was electrotransformed to Span038.

The DNA fragment I was used for the first homologous recombination: firstly transforming the pKD46 plasmid into the *Escherichia coli* Span038 by electrotransformation, and then electrotransforming the DNA fragment I into the *Escherichia coli* Span038 with pKD46.

The electrotransformation conditions and steps were consistent with those for the step one of alsS integration at the tdcDE loci described in Example 1. A 200 μl bacterial suspension was taken and coated on a LB plate containing ampicillin (final concentration of 100 μg/ml) and chloramphenicol (final concentration of 34 μg/ml), and was incubated at 30° C. overnight. Single colonies were selected for PCR validation using the primers ilvM-up/ilvE-down. The correct PCR product should be 3832 bp, comprising 283 bp of the ilvE gene upstream homology arm, 2619 bp of the cat-sacB fragment and 930 bp of the ilvE gene downstream homology arm. One correct single colony was selected and named Span039.

In step two, using the genomic DNA of wild-type *Escherichia coli* ATCC 8739 as a template, a 980 bp DNA fragment II was amplified using the primers ilvEGTG-up/ilvE-down.

The DNA fragment II comprises an ilvE gene with the start codon ATG changed to GTG. The DNA fragment II was used for the second homologous recombination. The DNA fragment II was electrotransformed to strain Span039.

The electrotransformation conditions and steps were consistent with those for the step two of alsS integration at the tdcDE loci described in Example 1. The clone was validated by colony PCR with the primers ilvM-up/ilvE-down. The correct colony amplification product was a fragment of 1213 bp, comprising 283 bp of the upstream homology arm of the ilvE gene and a total of 930 bp of the ilvE with the start codon ATG replaced by GTG. One correct single colony was selected and named Span040.

Span040 is a recombinant bacterium obtained by mutating the start codon ATG of ilvE of Span038 to GTG, and the mutated gene is designated as ilvE* gene (the sequence of said ilvE* gene is set forth as SEQ ID NO: 11), which encodes IlvE* protein (the sequence of said IlvE* protein is set forth as SEQ ID NO:12).

Example 21. Integration of a serA Gene Encoding Phosphoglycerate Dehydrogenase from *Corynebacterium glutamicum* at the Locus of Ara Gene Encoding Ribokinase and Knockout of the Ara Locus Starting from Span040, a serA gene encoding phosphoglycerate dehydrogenase from *Corynebacterium glutamicum* was integrated at the locus of the ara gene encoding ribokinase, which comprises specific steps as follows:

in step one, using the pXZ-CS plasmid DNA as a template, a 2719 bp DNA fragment I was amplified using the primers araBCD-CS-up/araBCD-CS-down, which was used for the first step of homologous recombination. The DNA fragment I comprises a 50 bp upstream homology arm of the ara locus, a 2619 bp cat-sacB fragment and a 50 bp downstream homology arm of the ara locus. The amplification system and amplification conditions were consistent with those described in Example 1. The DNA fragment I was electrotransformed to Span041.

The DNA fragment I was used for the first homologous recombination: firstly transforming the pKD46 plasmid into the *Escherichia coli* Span041 by electrotransformation, and then electrotransforming the DNA fragment I into the *Escherichia coli* Span041 with pKD46.

The electrotransformation conditions and steps were consistent with those for the step one of alsS integration at the tdcDE loci described in Example 1. A 200 μl bacterial suspension was taken and coated on a LB plate containing ampicillin (final concentration of 100 μg/ml) and chloramphenicol (final concentration of 34 μg/ml), and was incubated at 30° C. overnight. Single colonies were selected for PCR validation using the primers araBCD-YZ300-up/araBCD-YZ468-down, and the correct PCR product should be 3378 bp, comprising 291 bp of the upstream homology arm of the ara locus, 2619 bp of the cat-sacB fragment and 468 bp for the downstream homology arm of the ara locus. One correct single colony was selected and named Span041.

In step two, using the genomic DNA of *Corynebacterium glutamicum* ATCC13032 (ATCC product) as a template, a DNA fragment 11 of 1102 bp was amplified using the primers araBCD-serA197-up/araBCD-serA197-down. The DNA fragment II comprises 50 bp of the upstream homology arm of the ara locus, 1002 bp of the serA gene, and 50 bp of the downstream homology arm of the ara locus. The DNA fragment II was used for the second homologous recombination. The DNA fragment II was electrotransformed to strain Span041.

The electrotransformation conditions and steps were consistent with those for the step two of alsS integration at the tdcDE loci described in Example 1. The clone was validated by colony PCR using the primers araBCD-YZ300-up/araBCD-YZ468-down, and the correct colony amplification product was a 1761 bp fragment comprising 291 bp of the upstream homology arm of the ara locus, 1002 bp of the serA gene and 468 bp of the downstream homology arm of the ara locus. One correct single colony was selected and named Span042.

Span042 is a recombinant bacterium obtained by integrating the serA gene encoding phosphoglycerate dehydrogenase from *Corynebacterium glutamicum* (serA gene, whose nucleotide sequence is set forth as SEQ ID NO: 13, encoding the SerA protein of SEQ ID NO: 14) to the ara locus of *Escherichia coli* Span040, wherein the ara gene (the encoded protein sequence is NCBI ACA79208.1. coded_by=CP000946.1:3929533 . . . 3931233; the coded protein sequence is NCBI ACA79209.1, coded_by=CP000946.1:3931244 . . . 3932746) is simultaneously knocked out from this recombinant bacterium.

Example 22. Regulation of the serA Gene Encoding Phosphoglycerate Dehydrogenase from *Corynebacterium glutamicum*

Starting from Span042, the expression of the gene serA encoding phosphoglycerate dehydrogenase integrated at the ara locus was regulated using an artificial regulatory element, which comprises specific steps as follows:

in step one, using the pXZ-CS plasmid DNA as a template, a 2719 bp DNA fragment I was amplified using the primers araBCD-CS-up/serA197-ProCS-down, which was used for the first step of homologous recombination. The DNA fragment I comprises 50 bp of the upstream homology arm of the ara locus, 2619 bp of the cat-sacB fragment and 50 bp of the downstream homology arm of the serA locus. The amplification system and amplification conditions were consistent with those described in Example 1. The DNA fragment I was electrotransformed to Span042.

The DNA fragment I was used for the first homologous recombination: firstly transforming the pKD46 plasmid into the *Escherichia coli* Span042 by electrotransformation, and then electrotransforming the DNA fragment I into the *Escherichia coli* Span042 with pKD46.

The electrotransformation conditions and steps were consistent with those for the step one of alsS integration at the tdcDE loci described in Example 1. A 200 μl bacterial suspension was taken and coated on a LB plate containing ampicillin (final concentration of 100 μg/ml) and chloramphenicol (final concentration of 34 μg/ml), and was incubated at 30° C. overnight. Single colonies were selected for PCR validation using the primers araBCD-YZ300-up/SerA197-YZ358-down, and the correct PCR product should be 3268 bp, comprising 291 bp of the upstream homology arm of the ara locus, 2619 bp of the cat-sacB fragment and 358 bp of the downstream homology arm of the serA locus. One correct single colony was selected and named Span043.

In step two, using the genomic DNA of M1-93 (Lu, et al., *Appl Microbiol Biotechnol,* 2012, 93:2455-2462) as a template, a 188 bp DNA fragment II was amplified with primers serA197-Pro-up/serA197-Pro-down. The DNA fragment II comprises 50 bp of the upstream homology arm of the ara locus, 88 bp of the M1-93 promoter and 50 bp of the downstream homology arm of the serA gene. The DNA fragment H was electrotransformed to strain Span043.

The electrotransformation conditions and steps were consistent with those for the step two of alsS integration at the tdcDE loci described in Example 1. The clone was verified by colony PCR using the primers araBCD-YZ300-up/SerA197-YZ358-down, and the correct colony amplification product was a 737 bp fragment comprising 291 bp of the upstream homology arm of the ara locus, 88 bp of the M1-93 promoter and 358 bp of the downstream homology arm of the serA locus. One correct single colony was selected and named Span044.

Span044 is a recombinant bacterium obtained by integrating the M1-93 promoter (the nucleotide sequence of said M1-93 promoter is set forth as SEQ ID NO: 3) to the upstream of the serA gene of *Escherichia coli* Span042, wherein the M1-93 promoter drives the expression of the serA gene in this recombinant bacterium.

Example 23. Integration of a serC Gene Encoding Phosphoserine/Phosphohydroxythreonine Aminotransferase and a serB Gene Encoding Phosphoserine Phosphatase from *Escherichia coli* at the Locus of avtA Gene Encoding Valine-Pyruvate Transaminase and Knockout of the avtA Locus Starting from Span044, a serC gene encoding phosphoserine/phosphohydroxythreonine aminotransferase and a serB gene encoding phosphoserine phosphatase from *Escherichia coli* were integrated to the locus of the avtA gene encoding valine-pyruvate transaminase, which comprises specific steps as follows:

in step one, using the pXZ-CS plasmid DNA as a template, a 2719 bp DNA fragment I was amplified using the primers avtA-CS-up/avtA-CS-down, which was used for the first step of homologous recombination. The DNA fragment I comprises 50 bp of the upstream homology arm of the avtA locus, 2619 bp of the cat-sacB fragment and 50 bp of the downstream homology arm of the avtA locus. The amplification system and amplification conditions were consistent with those described in Example 1. The DNA fragment I was electrotransformed to Span044.

The DNA fragment I was used for the first homologous recombination: firstly transforming the pKD46 plasmid into the *Escherichia coli* Span044 by electrotransformation, and then electrotransforming the DNA fragment I into the *Escherichia coli* Span044 with pKD46.

The electrotransformation conditions and steps were consistent with those for the step one of alsS integration at the tdcDE loci described in Example 1. A 200 μl bacterial suspension was taken and coated on a LB plate containing ampicillin (final concentration of 100 μg/ml) and chloramphenicol (final concentration of 34 μg/ml), and was incubated at 30° C. overnight. Single colonies were selected for PCR validation using the primers avtA-YZ-up/avtA-YZ-down. The correct PCR product should be 3454 bp, comprising 416 bp of the upstream homology arm of the avtA locus, 2619 bp of the cat-sacB fragment and 419 bp of the downstream homology arm of the avtA locus. One correct single colony was selected and named Span045.

In step two, using the genomic DNA of *Escherichia coli* MG1655 (from ATCC, NO. 700926) as a template, a fragment II of 1181 was amplified using the primers avtA-serCB-up/serC-down. Using the genomic DNA of *Escheri-*

*chia coli* MG1655 (from ATCC, NO. 700926) as a template, a fragment III of 1062 was amplified using the primers serB-up/avtA-serCB-down. Using the primers avtA-serCB-up/avtA-serCB-down for PCR amplification, fusion PCR was performed to obtain fragment IV using equimolar fragments II and III as templates with the amplification system and conditions consistent with those described in Example 1. The fragment IV was a 2179 bp DNA fragment, which was used for the second homologous recombination. The fragment IV comprises 50 bp of the upstream homology arm of avtA, 1089 bp of the serC gene, 21 bp of the RBS sequence used for translation initiation of the serB gene and 969 bp of the serB gene, as well as 50 bp of the downstream homology arm of avtA. The DNA fragment IV was electrotransformed into the Span 045 strain.

The electrotransformation conditions and steps were consistent with those for the step two of alsS integration at the tdcDE loci described in Example 1. The clone was validated by colony PCR with the primers avtA-YZ-up/avtA-YZ-down and the correct colony amplification product was a 2914 bp fragment comprising 416 bp of the upstream homology arm of the avtA locus, 1089 bp of the serC gene, 21 bp of the RBS sequence used for translation initiation of the serB gene and 969 bp of the serB gene. One correct single colony was selected and named Span046.

Span046 is a recombinant bacterium obtained by integrating the serC gene encoding phosphoserine/phosphohydroxythreonine aminotransferase and the serB gene encoding phosphoserine phosphatase (serCB gene cluster, whose nucleotide sequence is set forth as SEQ ID NO: 15, which encodes the SerC protein of SEQ ID NO: 16 and the SerB protein of SEQ ID NO: 17) of *Escherichia coli* to the avtA locus of *Escherichia coli* Span044, wherein the avtA gene (the encoded protein sequence is NCBI ACA75824.1, coded_by=C P000946.1:153868 . . . 155121) is simultaneously knocked out from this recombinant bacterium.

In SEQ ID NO: 15, positions 1 to 88 are the M1-93 promoter sequence; positions 89 to 1177 are the serC gene sequence; positions 1178 to 1198 are the RBS sequence used for the translation initiation of the serB gene; and positions 1199 to 2167 are the sequence of the serB gene.

Example 24. Regulation of Expression of the serCB Gene Cluster Integrated at the avtA Locus Starting from Span046, the expression of the gene clusters of the serC gene encoding phosphoserine/phosphohydroxythreonine aminotransferase and the serB gene encoding phosphoserine phosphatase from *Escherichia coli* integrated at the avtA locus was regulated using an artificial regulatory element, which comprises specific steps as follows:

in step one, using the pXZ-CS plasmid DNA as a template, a 2719 bp DNA fragment I was amplified using the primers avtA-CS-up/serCB-ProCS-down, which was used for the first step of homologous recombination. The DNA fragment I comprises 50 bp of the upstream homology arm of the avtA locus, 2619 bp of the cat-sacB fragment and 50 bp of the downstream homology arm of the serC gene. The amplification system and amplification conditions were consistent with those described in Example 1. The DNA fragment I was electrotransformed to Span046.

The DNA fragment I was used for the first homologous recombination: firstly transforming the pKD46 plasmid into the *Escherichia coli* Span046 by electrotransformation, and then electrotransforming the DNA fragment I into the *Escherichia coli* Span046 with pKD46.

The electrotransformation conditions and steps were consistent with those for the step one of alsS integration at the tdcDE loci described in Example 1. A 200 μl bacterial suspension was taken and coated on a LB plate containing ampicillin (final concentration of 100 μg/ml) and chloramphenicol (final concentration of 34 μgimp, and was incubated at 30° C. overnight. Single colonies were selected for PCR validation using the primers avtA-YZ-up/serCB-YZ317-down. The correct PCR product should be 3456 bp, comprising 416 bp of the upstream homology arm of the avtA locus, 2619 bp of the cat-sacB fragment and 421 bp of the downstream homology arm of the serC gene. One correct single colony was selected and named Span047.

In step two, using the genomic DNA of M1-93 (Lu, et al., *Appl Microbiol Biotechnol*, 2012, 93:2455-2462) as a template, a 188 bp DNA fragment II was amplified with primers serCB-Pro-up/serCB-Pro-down. The DNA fragment II comprises 50 bp of the upstream homology arm of the avtA locus, 88 bp of the M1-93 promoter sequence and 50 bp of the downstream homology arm of the serC gene. The DNA fragment II was electrotransformed to strain Span047.

The electrotransformation conditions and steps were consistent with those for the step two of alsS integration at the tdcDE loci described in Example 1. The clone was validated by colony PCR using the primers avtA-YZ-up/serCB-YZ317-down and the correct colony amplification product was a 925 bp fragment comprising 416 bp of the upstream homology arm of the avtA locus, 88 bp of the M1-93 promoter sequence and 421 bp of the downstream homology arm of the serC gene. One correct single colony was selected and named Span048.

Span048 is a recombinant bacterium obtained by integrating the M1-93 promoter to the upstream of the serCB gene cluster of *Escherichia coli* Span046, containing an expression cassette of the serCB gene cluster of SEQ ID NO: 15, wherein the M1-93 promoter (the nucleotide sequence of said M1-93 promoter is from positions 1 to 88 of SEQ ID NO: 15) drives the expression of the serC and serB genes in the serCB gene cluster.

Example 25. Knockout of the sdaA Gene Encoding L-Serine Deaminase I

Starting from Span048, the sdaA gene encoding L-serine deaminase I was knocked out, which comprises specific steps as follows:

in step one, using the pXZ-CS plasmid DNA as a template, a 2719 bp DNA fragment I was amplified using the primers sdaA-delcat-up/sdaA-delsacB-down, which was used for the first step of homologous recombination. The DNA fragment I comprises 50 bp of the upstream homology arm of the sdaA locus, 2619 bp of the cat-sacB fragment and 50 bp of the downstream homology arm of the sdaA gene. The amplification system and amplification conditions were consistent with those described in Example 1. The DNA fragment I was electrotransformed to Span048.

The DNA fragment I was used for the first homologous recombination: firstly transforming the pKD46 plasmid to the *Escherichia coli* Span048 by electrotransformation, and then electrotransforming the DNA fragment I to the *Escherichia coli* Span048 with pKD46.

The electrotransformation conditions and steps were consistent with those for the step one of alsS integration at the tdcDE loci described in Example 1. A 200 μl bacterial suspension was taken and coated on a LB plate containing ampicillin (final concentration of 100 µg/ml) and chloramphenicol (final concentration of 34 µg/ml), and was incubated at 30° C. overnight. Single colonies were selected for PCR validation using the primers sdaA-YZ-up/sdaA-YZ-down. The correct PCR product should be 3428 bp, comprising 383 bp of the upstream homology arm of the sdaA locus, 2619 bp of the cat-sacB fragment and 426 bp of the downstream homology arm of the sdaA gene. One correct single colony was selected and named Span049.

In step two, using the genomic DNA of Escherichia coli ATCC 8739 as a template, a 433 bp DNA fragment II was amplified using the primers sdaA-YZ-up/SdaAdel-down. The DNA fragment II comprises 383 bp of the upstream homology arm of sdaA and 50 bp of the downstream homology arm. The DNA fragment II was used for the second homologous recombination. The DNA fragment II was electrotransformed to strain Span049.

The electrotransformation conditions and steps were consistent with those for the step two of alsS integration at the tdcDE loci described in Example 1. The clone was validated by colony PCR with primers sdaA-YZ-up/sdaA-YZ-down and the correct colony amplification product was a 809 bp fragment comprising 383 bp of the upstream homology arm of the sdaA locus and 426 bp in the downstream homology arm of the sdaA gene. One correct single colony was selected and named Span050.

Span050 is a recombinant bacterium obtained by knocking out the sdaA gene encoding L-serine deaminase I (the encoded protein sequence is NCBI ACA77468.1, coded_by=CP000946.1:2018393 . . . 2019757) of Escherichia coli Span048, wherein the sdaA gene is not contained in this recombinant bacterium.

Span050 was deposited in the China General Microbiological Culture Collection Center on Jan. 22, 2021 under the accession number CGMCC No. 21699.

Example 26. Production of Pantoic Acid Using Span050

The seed medium comprises the following components (solvent was water):

Major elements: glucose 20 g/L, $(NH_4)_2HPO_4$ 3.5 g/L, $KH_2PO_4$ 3.91 g/L, $K_2HPO_4$ 4.48 g/L, $MgSO_4·7H_2O$ 0.18 g/L, betaine-HCl 0.15 g/L.

Trace elements: $FeCl_3·6H_2O$ 1.5 µg/L, $CoCl_2·6H_2O$ 0.1 µg/L, $CuCl_2·2H_2O$ 0.1 µg/L, $ZnCl_2$ 0.1 µg/L, $Na_2MoO_4·2H_2O$ 0.1 µg/L, $MnCl_2·4H_2O$ 0.2 µg/L, $H_3BO_3$ 0.05 µg/L.

The fermentation medium was mostly the same as the seed medium, with the difference that the glucose concentration was 50 g/L and the fermentation medium further contains 5 g/L serine.

The fermentation of Span050 comprises the following steps.

(1) Seed culture: a fresh clone on LB plate was inoculated into a tube containing 4 ml of seed medium and incubated at 37° C. with 250 rpm shaking overnight. Then, the culture was transferred to a 250 ml triangular flask containing 30 ml of seed medium at 2% (V/V) of inoculum level and incubated at 37° C. with 250 rpm shaking for 12 hours to obtain the seed culture solution for fermentation medium inoculation.

(2) Fermentation culture: The volume of the fermentation medium in the 250 ml triangular flask was 25 ml, and the seed culture solution was inoculated into the fermentation medium according to the inoculum level of a final concentration of OD550=0.1, and incubated at 37° C. and 250 rpm for 60 hours to obtain the fermentation broth.

Analytical methods: The components in the fermentation broth after fermentation for 3 days were determined using Agilent (Agilent-1260) high-performance liquid chromatography instrument. The concentration of glucose and pantoic acid in the fermentation broth was determined using an Aminex HPX-87H organic acid analytical column from Biorad.

The results shows that 1.2 g/L of pantoic acid can be produce with fermentation of the Span050 strain for 3 days, which indicates that the pantoic acid synthesis pathway in the Span050 strain has been opened and the accumulation of pantoic acid can be achieved during the fermentation.

Example 27. Fermentation of Span050 in a 5 L Tank

The composition and preparation of the seed medium and the analytical methods were the same as those described in Example 26.

Fermentation medium: glucose 30 g/L, magnesium sulfate 5 g/L, potassium dihydrogen phosphate 10.5 g/L, yeast powder 20 g/L, diammonium hydrogen phosphate 6 g/L, citric acid monohydrate 1.84 g/L and trace elements as in the fermentation medium of Example 26 in water.

Supplementary medium: 600 g/L of glucose in water.

Fermentation was carried out in a 5 L fermenter (Shanghai Baoxing, BIOTECH-5BG), comprising the following steps.

(1) Seed culture: 50 mL of seed medium in a 500 mL triangular flask was sterilized at 115° C. for 15 min. After cooling, the recombinant Escherichia coli Span050 was inoculated in the seed medium at an inoculum level of 1% (V/V) and incubated at 37° C. and 250 rpm for 12 h to obtain seed solution for fermentation medium inoculation.

(2) Fermentation culture: The volume of the fermentation medium in the 5 L fermenter was 3 L, sterilized at 115° C. for 25 min. The seed solution was inoculated in the fermentation medium according to the inoculum level of a final concentration of OD550=0.2. The dissolved oxygen was maintained at 30%, and ammonia was used as a neutralizing agent to maintain the pH at 7.0. The glucose concentration in the tank was controlled below 5 g/L by replenishing the medium, and the fermentation broth was obtained by culture at 37° C. for 3 days. The fermentation broth was all substances in the fermenter.

The results shows that the yield of pantoic acid reaches 22 g/L after Span050 fermentation for 3 days, which has a good potential for industrial application.

INDUSTRIAL APPLICATION

A strain capable of producing panthoic acid was obtained successfully by using the construction method of a recombinant Escherichia coli of the present invention. The pantoic acid synthesis route of said strain has been established and the accumulation of pantoic acid can be achieved during the fermentation. The construction method of a recombinant Escherichia coli and the obtained recombinant Escherichia coli have good potential in industrial application.

The invention claimed is:

1. A method of constructing a recombinant *Escherichia coli*, comprising modifying a starting *Escherichia coli* per the following steps of A1-A25 to obtain the recombinant *Escherichia coli*:

A1. introducing and expressing an alsS gene encoding acetolactate synthase;

A2. replacing the promoter of ilvB gene encoding the large subunit of acetolactate synthase I with M1-93 promoter, wherein the M1-93 promoter is a DNA molecule, wherein the nucleotide sequence of one strand of the DNA molecule is set forth as SEQ ID NO: 3;

A3. replacing the promoter of ilvG gene encoding the large subunit of acetolactate synthase II with the M1-93 promoter;

A4. mutating the ilvH gene encoding a regulatory subunit of acetolactate synthase III to an ilvH mutant gene, wherein the ilvH mutant gene encodes the protein of SEQ ID NO: 5;

A5. introducing and expressing an ilvC gene encoding acetohydroxyl-acid reductoisomerase;

A6. introducing and expressing an ilvD gene encoding dihydroxy-acid dehydratase;

A7. introducing and expressing a panB gene encoding 3-methyl-2-oxobutanoate hydroxymethyltransferase derived from *Escherichia coli*, which is designated as E-panB gene;

A8. introducing and expressing a panE gene encoding 2-dehydropantothenate-2-reductase;

A9. introducing and expressing a glyA gene encoding glycine hydroxymethyltransferase;

A10. replacing the promoter of gcvT gene encoding aminomethyltransferase with the M1-93 promoter;

A11. replacing the promoter of gcvP gene encoding glycine decarboxylase with the M1-93 promoter;

A12. introducing and expressing a panB gene encoding 3-methyl-2-oxobutanoate hydroxymethyltransferase derived from *Corynebacterium glutamicum*, which is designated as C-panB gene;

A13. mutating the ilvE gene encoding branched-chain amino acid aminotransferase to an ilvE mutant gene, wherein the ilvE mutant gene encodes the protein of SEQ ID NO: 12;

A14. introducing and expressing a serA gene encoding phosphoglycerate dehydrogenase;

A15. introducing and expressing a serC gene encoding phosphoserine/phosphohydroxythreonine aminotransferase and a serB gene encoding phosphoserine phosphatase;

A16. knocking out the sdaA gene encoding L-serine deaminase I;

A17. knocking out the tdcD gene encoding propionate kinase and the tdcE gene encoding formate acetyltransferase;

A18. knocking out the adhE gene encoding alcohol dehydrogenase;

A19. knocking out the pflB gene encoding pyruvate formate lyase;

A20. knocking out the frd gene encoding fumarate reductase;

A21. knocking out the ldhA gene encoding lactate dehydrogenase;

A22. knocking out the mgsA gene encoding methylglyoxal synthase;

A23. knocking out the pta gene encoding the phosphate acetyltransferase and the ackA gene encoding acetate kinase;

A24. knocking out the ara gene encoding ribokinase and

A25. knocking out the avtA gene encoding valine-pyruvate transaminase.

2. The method according to claim 1, characterized in that:

the alsS gene is derived from *Bacillus subtilis;* and/or, the ilvC gene is derived from *Escherichia coli;* and/or, the ilvD gene is derived from *Escherichia coli;* and/or, the panE gene is derived from *Escherichia coli;* and/or, the glyA gene is derived from *Escherichia coli;* and/or, the serA gene is derived from *Corynebacterium glutamicum;* and/or, the serC gene and the serB gene are derived from *Escherichia coli.*

3. The method according to claim 2, characterized in that:

the alsS gene encodes the AlsS protein of SEQ ID NO: 2;

and/or, the C-panB gene encodes the C-panB protein of SEQ ID NO: 10;

and/or, the serA gene encodes the SerA protein of SEQ ID NO: 14;

and/or, the serC gene encodes the SerC protein of SEQ ID NO: 16;

and/or, the serB gene encodes the SerB protein of SEQ ID NO: 17.

4. The method according to claim 1, characterized in that:
the sequence of the alsS gene is set forth as SEQ ID NO: 1;
and/or, the sequence of the ilvH mutant gene is set forth as SEQ ID NO: 4;
and/or, the sequence of the C-panB gene is set forth as SEQ ID NO: 9;
and/or, the sequence of the ilvE mutant gene is set forth as SEQ ID NO: 11;
and/or, the sequence of the serA gene is set forth as SEQ ID NO: 13;
and/or, the sequence of the serC gene is from positions 89 to 1177 of SEQ ID NO: 15;
and/or, the sequence of the serB gene is from positions 1199 to 2167 of SEQ ID NO: 15.

5. The method according to claim 1, characterized in that:
A1 is achieved by introducing an alsS gene expression cassette into the recipient *Escherichia coli*, wherein the alsS gene expression cassette contains a promoter and the alsS gene driven by the promoter;
and/or, A5 is achieved by introducing an ilvC gene expression cassette into the recipient *Escherichia coli*, wherein the ilvC gene expression cassette contains a promoter and the ilvC gene driven by the promoter;
and/or, A6 is achieved by introducing an ilvD gene expression cassette into the recipient *Escherichia coli*, wherein the ilvD gene expression cassette contains a promoter and the ilvD gene driven by the promoter;
and/or, A7 is achieved by introducing an E-panB gene expression cassette into the recipient *Escherichia coli*, wherein the E-panB gene expression cassette contains a promoter and the E-panB gene driven by the promoter;
and/or, A8 is achieved by introducing a panE gene expression cassette into the recipient *Escherichia coli*, wherein the panE gene expression cassette contains a promoter and the panE gene driven by the promoter;
and/or, A9 is achieved by introducing a glyA gene expression cassette into the recipient *Escherichia coli*, wherein the glyA gene expression cassette contains a promoter and the glyA gene driven by the promoter;
and/or, A12 is achieved by introducing a C-panB gene expression cassette into the recipient *Escherichia coli*, wherein the C-panB gene expression cassette contains a promoter and the C-panB gene driven by the promoter;
and/or, A14 is achieved by introducing a serA gene expression cassette into the recipient *Escherichia coli*, wherein the serA gene expression cassette contains a promoter and the serA gene driven by the promoter;
and/or, A15 is achieved by introducing a serCB gene expression cassette into the recipient *Escherichia coli*, wherein the serCB gene expression cassette contains a promoter and the serC gene and the serB gene driven by the promoter.

6. The method according to claim 5, characterized in that:
the promoter in A1, A7, A12, A14 or A15 is the M1-93 promoter;
the promoter in A5 or A9 is M1-46 promoter, wherein the M1-46 promoter is any selected from the group consisting of the following DNA molecules:
1) A DNA molecule, wherein the nucleotide sequence of one strand of the DNA molecule is set forth as SEQ ID NO: 6;
2) A DNA molecule having at least 80% identity with the DNA molecule in 1) and having a promoter function;
the promoter in A6 is RBSL1 promoter, wherein the RBSL1 promoter is any selected from the group consisting of the following DNA molecules:
a1) a DNA molecule, wherein the nucleotide sequence of one strand of the DNA molecule is set forth as SEQ ID NO: 7;
a2) a DNA molecule having at least 80% identity with the DNA molecule in a1) and having a promoter function;
the promoter in A8 is RBSL2 promoter, wherein the RBSL2 promoter is any selected from the group consisting of the following DNA molecules:
c1) a DNA molecule, wherein the nucleotide sequence of one strand of the DNA molecule is set forth as SEQ ID NO: 8;
c2) a DNA molecule having at least 80% identity with the DNA molecule in c1) and having a promoter function;
and/or, the starting *Escherichia coli* is *Escherichia coli* ATCC 8739.

7. A recombinant *Escherichia coli* obtained using the method according to claim 1.

8. The recombinant *Escherichia coli* according to claim 7, characterized in that: the recombinant *Escherichia coli* is the strain deposited in the China General Microbiological Culture Collection Center with the accession number of CGMCC No. 21699.

9. A method of producing pantoic acid, comprising: culturing the recombinant *Escherichia coli* according to claim 7 to obtain fermentation products; and obtaining pantoic acid from the fermentation products.

10. A method of producing pantoic acid, comprising: culturing the recombinant *Escherichia coli* according to claim 8 to obtain fermentation products; and obtaining pantoic acid from the fermentation products.

11. The method of claim 10, further comprising converting the pantoic acid obtained from the fermentation products to calcium pantothenate.

12. The method of claim 9, further comprising converting the pantoic acid obtained from the fermentation products to calcium pantothenate.

* * * * *